US012593768B2

(12) United States Patent
Puglisi et al.

(10) Patent No.: US 12,593,768 B2
(45) Date of Patent: Apr. 7, 2026

(54) WATERMELON GENE CONFERRING A HIGH NUMBER OF MALE FLOWERS

(71) Applicant: NUNHEMS B.V., Nunhem (NL)

(72) Inventors: Daniel Puglisi, Sant Agata Bolognese (IT); Alberto Sirizzotti, Sant Agata Bolognese (IT); Courtney Hu, Sacramento, CA (US); Mona Mazaheri, Davis, CA (US); Giulia Pagliarani, Sant Agata Bolognese (IT)

(73) Assignee: NUNHEMS B.V., Nunhem (NL)

( * ) Notice: Subject to any disclaimer, the term of this patent is extended or adjusted under 35 U.S.C. 154(b) by 200 days.

(21) Appl. No.: 18/283,618

(22) PCT Filed: Mar. 16, 2022

(86) PCT No.: PCT/EP2022/056848
§ 371 (c)(1),
(2) Date: Sep. 22, 2023

(87) PCT Pub. No.: WO2022/200149
PCT Pub. Date: Sep. 29, 2022

(65) Prior Publication Data
US 2024/0164270 A1 May 23, 2024

Related U.S. Application Data

(60) Provisional application No. 63/166,040, filed on Mar. 25, 2021.

(30) Foreign Application Priority Data

May 3, 2021 (EP) ..................................... 21171772

(51) Int. Cl.
*A01H 6/34* (2018.01)
*A01H 5/08* (2018.01)

(52) U.S. Cl.
CPC ............... *A01H 6/342* (2018.05); *A01H 5/08* (2013.01)

(58) Field of Classification Search
None
See application file for complete search history.

(56) References Cited

U.S. PATENT DOCUMENTS 7,314,979 B2   1/2008   Lanini et al.
10,188,055 B1*   1/2019   Guner ...................... A01H 5/10
(Continued)

FOREIGN PATENT DOCUMENTS

WO   2013/107632 A1   7/2013
WO   2019/106638 A1   6/2019
(Continued)

OTHER PUBLICATIONS

Damayanti, Farida, et al. "Functional disruption of the tomato putative ortholog of Hawaiian Skirt results in facultative parthenocarpy, reduced fertility and leaf morphological defects." Frontiers in Plant Science 10 (2019): 1234. (Year: 2019).*
(Continued)

*Primary Examiner* — Weihua Fan
(74) *Attorney, Agent, or Firm* — ArentFox Schiff LLP

(57) ABSTRACT

The present invention is directed to a gene which, when mutated, results in presence of many male flowers and absence of female flowers in watermelon. Plants comprising mutant alleles of this gene are useful as pollenizers in the production of triploid, seedless watermelon fruits.

Figure 5:
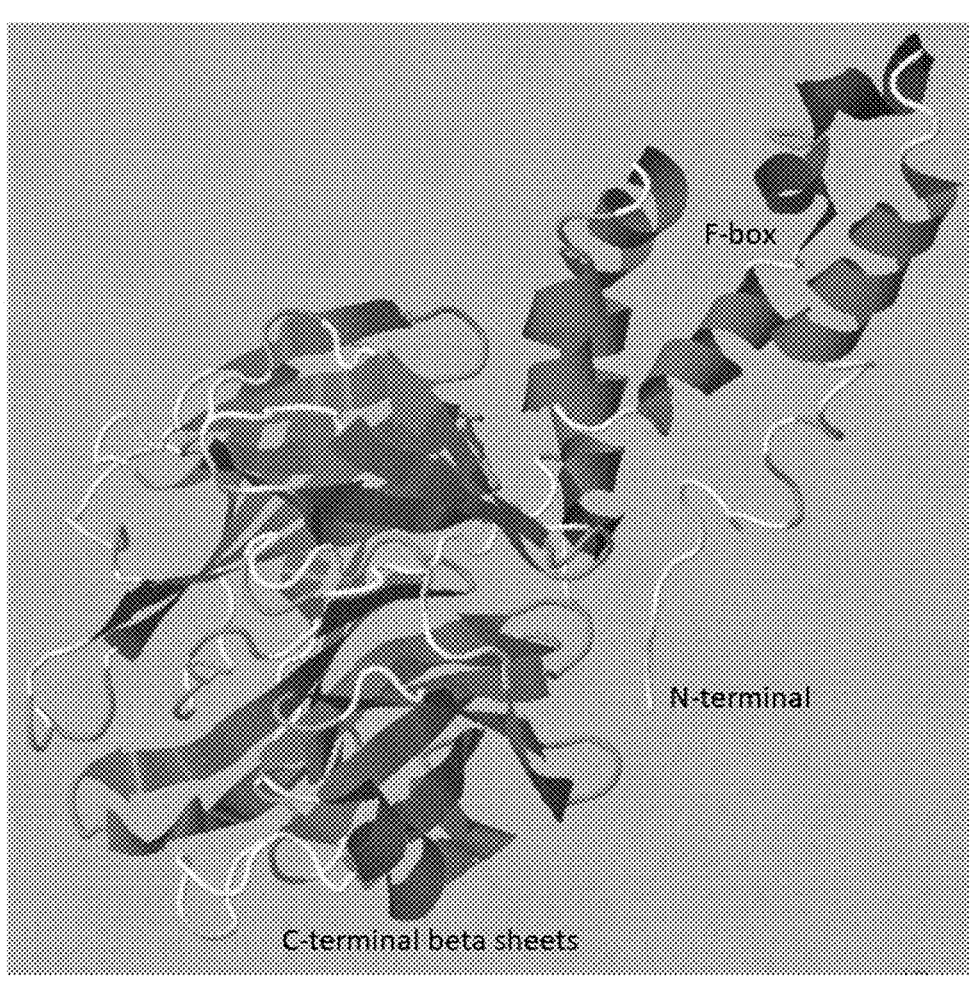

19 Claims, 6 Drawing Sheets
Specification includes a Sequence Listing.

(56) References Cited

U.S. PATENT DOCUMENTS

| | | | |
|---|---|---|---|
| 2015/0101072 A1* | 4/2015 | Lanini | A01H 6/342 |
| | | | 435/430 |
| 2020/0093086 A1 | 3/2020 | De Groot et al. | |

FOREIGN PATENT DOCUMENTS

| | | |
|---|---|---|
| WO | 2019/106639 A1 | 6/2019 |
| WO | 2019/106641 A2 | 6/2019 |
| WO | 2020/025133 A1 | 2/2020 |

OTHER PUBLICATIONS

Nagata, Toshifumi, Fabien Lombardo, and Hiroshi Ezura. "Complementation of the tomato HWS gene with its *Arabidopsis* counterpart demonstrates conservation of the gene function between both species." Plant Biotechnology 38.3 (2021): 387-390. (Year: 2021).*

Lang, Patricia LM, et al. "A role for the F-box protein Hawaiian Skirt in plant microRNA function." Plant physiology 176.1 (2018): 730-741. (Year: 2018).*

"Sidekick: Pollenizer for triploid watermelons, New super pollenizer for triploid watermelons", Harris Moran Seed Company. 2014. URL—https://hmclause.com/wp-content/uploads/2021/11/USACANADA_Watermelon_Sidekick_Techsheet_2014_ENG.pdf.

"Watermelon (Charleston Gray) Genome", CuGenDB. 2019. URL—http://www.cucurbitgenomics.org/organism/4.

Aguado, et al., "Mapping a Partial Andromonoecy Locus in Citrullus lanatus Using BSA-Seq and GWAS Approaches", Frontiers in plant science, vol. 11, Article No. 1243, Aug. 19, 2020, pp. 1-16.

Allen, et al., "Transcript-specific, single-nucleotide polymorphism discovery and linkage analysis in hexaploid bread wheat (*Triticum aestivum* L.)", Plant biotechnology journal, vol. 9, Issue 9, Jun. 1, 2011, pp. 1086-1099.

Alluvada, et al., Unpublished EP Patent Application No. 21194565.4, filed on Sep. 2, 2021, titled "Methods for selecting watermelon plants and plant parts comprising a modified DWARF14 gene", 74 pages.

Alluvada, et al., Unpublished U.S. Appl. No. 63/217,071, filed Jun. 30, 2021, titled "Methods for selecting watermelon plants and plant parts comprising a modified DWARF14 gene", 65 pages.

European Search Report for EP Patent Application No. 21171772.3, Issued on Oct. 22, 2021, 4 pages.

Garcia, et al., "Two androecious mutations reveal the crucial role of ethylene receptors in the initiation of female flower development in Cucurbita pepo", The Plant Journal, vol. 103, Issue 4, May 21, 2020, pp. 1548-1560.

González-Carranza, et al., "Hawaiian Skirt: an F-box gene that regulates organ fusion and growth in *Arabidopsis*", Plant physiology, vol. 144, Issue 3, May 11, 2007, pp. 1370-1382.

Henikoff, et al., "Amino acid substitution matrices from protein blocks", Proceedings of the National Academy of Sciences, vol. 89, Issue 22, Nov. 15, 1992, pp. 10915-10919.

International Search Report for PCT Patent Application No. PCT/EP2022/056848, Issued on Jun. 15, 2022, 5 pages.

Ji, et al., "Inheritance of sex forms in watermelon (*Citrullus lanatus*)", Scientia Horticulture, vol. 193, Sep. 22, 2015, pp. 367-373.

Jiang, et al., "Discovery of watermelon gynoecious gene gy", Acta Horticulturae Sinica, vol. 34, Issue 1, 2007, pp. 141-142.

Li, et al., "Gene Interactions Regulating Sex Determination in Cucurbits", Frontiers in plant science, vol. 10, Article No. 1231, Oct. 10, 2019, pp. 1-12.

McGregor, et al., "Flowering Patterns of Pollenizer and Triploid Watermelon Cultivars", HortScience-American Society of Horticulture Science, vol. 49, Issue 6, Jun. 2014, pp. 714-721.

Xu, et al., "Evolution of F-box genes in plants: different modes of sequence divergence and their relationships with functional diversification", Proceedings of the National Academy of Sciences, vol. 106, Issue 3, Jan. 20, 2009, pp. 835-840.

Zhang, et al., "Tissue culture-induced heritable genomic variation in rice, and their phenotypic implications", PloS one, vol. 9, Issue 5, May 7, 2014, pp. 1-10.

* cited by examiner

Figure 1

```
WT        1 MEGQTSWIRHCYNDMSRDLEDLDSYLDFTNEGGKEAVAVSVESILPDDLL      50
            |||||||||||||||||||||||||||||||||||||||||||||||||
Mutant    1 MEGQTSWIRHCYNDMSRDLEDLDSYLDFTNEGGKEAVAVSVESILPDDLL      50

WT       51 ERILSYLPIASIFRAGSVCKRWHDIVSSRRFLWNVSHILSQKPWYFMFTS     100
            |||||||||||||||||||||||||||||||||||||||||||||||||
Mutant   51 ERILSYLPIASIFRAGSVCKRWHDIVSSRRFLWNVSHILSQKPWYFMFTS     100

WT      101 SDEPIGYAYDPVLRKWYAINLPCIDKSNCFIASSCGLVCFMDNDSRSELH     150
            |||||||||||||||||||||||||||||||||||||||||||||||||
Mutant  101 SDEPIGYAYDPVLRKWYAINLPCIDKSNCFIASSCGLVCFMDNDSRSELH     150

WT      151 VCNPITKCSMKLPEPTGSKFSDYSALAISVNRVSHNYTISVVKSKQVPGN     200
            |||||||||||||||||||||||||||||||||||||||||||||||||
Mutant  151 VCNPITKCSMKLPEPTGSKFSDYSALAISVNRVSHNYTISVVKSKQVPGN     200

WT      201 FFQWDISIHIYDSETMMWVTSLTEVLSGWRGGDESVICDGVLYLLIYSTG     250
            |||
Mutant  201 FFQ---------------------------------------------------     203

WT      251 GGAPDNRHGLVTYNISNHSSHGLLIRSFIPAPCSLTCGRLMNLKQKLVMV     300
Mutant  204 -----------------------------------------------------     203

WT      301 GGIGKQDRPDIIKGIGIWILCGKEWREIARMPHKFFQGFGEFDDVFASCG     350
Mutant  204 -----------------------------------------------------     203

WT      351 TDDLIYIQSYGAPALLTFDMNLRQWRWSQKCPVTKRFPLQLFTGFCFEPR     400
Mutant  204 -----------------------------------------------------     203

WT      401 LEINP      405
Mutant  204 -------      203
```

Figure 2

```
# Length: 415
# Identity:     272/415 (65.5%)
# Similarity:   344/415 (82.9%)
# Gaps:          14/415 ( 3.4%)
# Score: 1494.0

#=======================================

WMW           1 MEGQTSWIRHCYNDMSRDLEDLDSYLDFTNEGGKEAVAVSVESILPDDLL     50
                ||.:|||..:.|:.::. .:.:.:||.:.:::,.| ....|::|:|||||
At3g61590     1 MEAETSWTNYPYSYITY-VPEAESYREQSDDEAK-VETFSMDSLLPDDLL     48

WMW          51 ERILSYLPIASIFRAGSVCKRWHDIVSSRRFLWNVS--HILSQKPWYFMFT     99
                |||||:||||||||||||:||||:::||||||||.|.| :.:|:|:|||||
At3g61590    49 ERILSFLPIASIFRAGTVCKRWNEIVSSRRFLCNFSNNSVSQRPWYFMFT     98

WMW         100 SSDEPIGYAYDPVLRKWYAINLPCIDKSNCFIASSCGLVCFMDNDSRSEL     149
                ::|:|.|||||||::||||:.:||||:.||.|:||||||||||||||.|:::
At3g61590    99 TTDDPSGYAYDPIIRKWYSFDLPCIETSNWFVASSCGLVCFMDNDCRNKI     148

WMW         150 HVCNPITKCSMKLPEPTGSKFSDYSALAIS--------VNRVSHNYTISVV     192
                :|.|||||....|.||.|.|.:||:|::::.|       |||.:.:|::|:|
At3g61590   149 YVSNPITKQWRTLIEPPGHKSTDYTAMSTSVNRANQAVNRANRSYSVSIV     198

WMW         193 KSKQVPGNFFQWDISIHIYDSETMMWVTSLTEVLSGWRGGDESVICDGVL     242
                |||||||||||||||:|||:|.||||.|.|.|.:.:||||||||:||||:.||
At3g61590   199 KSKQVPGNFFQWDLSIHLYSSETMTWTTLVNDVLSGWRGGNESVICNNVL     248

WMW         243 YLLIYSTGGGAPDNRHGLVTYNISN---HSSHGLLIRSFIPAPCSLTCGRL     290
                |.:||||||. |:|||:..|:|: ..|.|:|:|||||.|||||||||
At3g61590   249 YFMIYSTGGS---DHRHGLIASNLSSIGSPSSGILMRSFIPMPCSLTCGRL     296

WMW         291 MNLKQKLVMVGGIGKQDRPDIIKGIGIWILCGKEWREIARMPHKFFQGFG     340
                |||::::||:||||||.|||::||||||||||:|.||||.|:::||.:|||||
At3g61590   297 MNLRERLVIVGGIGKHDRPEVIKGIGIWVLKGKEWVEMAKMPQRFFQGFG     346

WMW         341 EFDDVFASCGTDDLIYIQSYGAPALLTFDMNLRQWRWSQKCPVTKRFPLQ     390
                |||:|||.|||||:||||||:||||||||||||:.||||||||||:||||
At3g61590   347 EFDEVFASSGTDDLVYIQSYGSPALLTFDMNLKYWRWSQKCPVTKKFPLQ     396

WMW         391 LFTGFCFEPRLEINP     405
                |||||||||||||.|
At3g61590   397 LFTGFCFEPRLEIAP     411
```

Figure 3
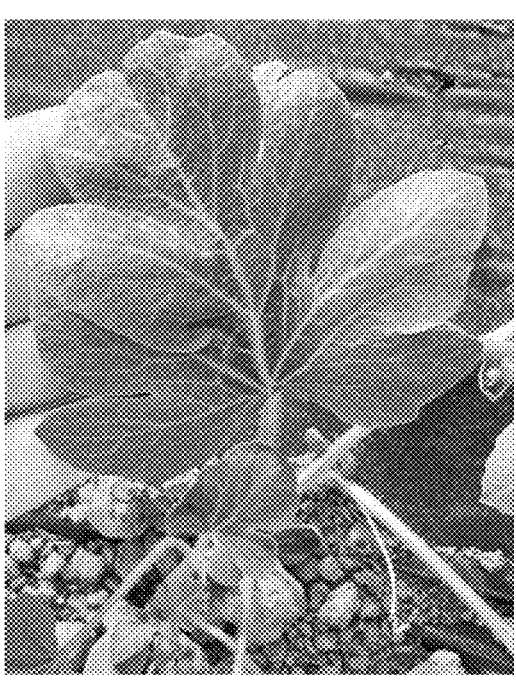 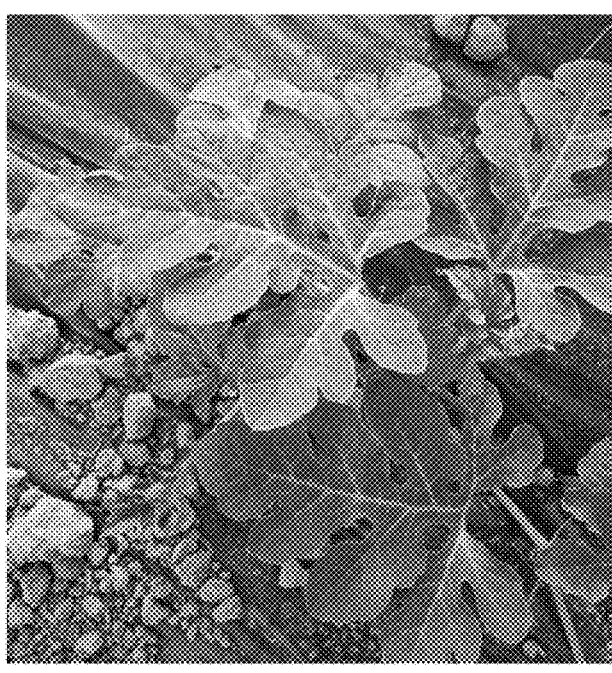
Figure 4
 

Figure 6

```
ID7          1 MIKWLLCFSFLSFSFAIPPASEVSSSNLAVPHFQVAAEEAFYKGQTSWIR       50
                                                          .:|||||||
ID1          1 ------------------------------------------------MEGQTSWIR        9

ID7         51 HCYNDMSRDLEDLDSYLDFTNEGGKEAVAVSVESILPDDLLERILSYLPI      100
                |||||||||||||||||||||||||||||||||||||||||||||||||||
ID1         10 HCYNDMSRDLEDLDSYLDFTNEGGKEAVAVSVESILPDDLLERILSYLPI       59

ID7        101 ASIFRAGSVCKPWHDIVSSRRFLWNVSHILSQKPWYFMFTSSDEPIGYAY      150
                |||||||||||||||||||||||||||||||||||||||||||||||||
ID1         60 ASIFRAGSVCKRWHDIVSSRRFLWNVSHILSQKPWYFMFTSSDEPIGYAY      109

ID7        151 DPVLRKWYAINLPCIDKSNCFIASSCGLVCFMDNDSRSELHVCNPITKCS      200
                |||||||||||||||||||||||||||||||||||||||||||||||||||
ID1        110 DPVLRKWYAINLPCIDKSNCFIASSCGLVCFMDNDSRSELHVCNPITKCS      159

ID7        201 MKLPEPTGSKFSDYSALAISVNRVSHNYTISVVKSKQVPGNFFQWDISIH      250
                |||||||||||||||||||||||||||||||||||||||||||||||||||
ID1        160 MKLPEPTGSKFSDYSALAISVNRVSHNYTISVVKSKQVPGNFFQWDISIH      209

ID7        251 IYDSETMMWVTSLTEVLSGWRGGDESVICDGVLYLLIYSTGGGAPDNRHG      300
                |||||||||||||||||||||||||||||||||||||||||||||||||||
ID1        210 IYDSETMMWVTSLTEVLSGWRGGDESVICDGVLYLLIYSTGGGAPDNRHG      259

ID7        301 LVTYNISNHSSHGLLIRSFIPAPCSLTCGRLMNLKQKLVMVGGIGKQDRP      350
                |||||||||||||||||||||||||||||||||||||||||||||||||||
ID1        260 LVTYNISNHSSHGLLIRSFIPAPCSLTCGRLMNLKQKLVMVGGIGKQDRP      309

ID7        351 DIIKGIGIWILCGKEWREIARMPHKFFQGFGEFDDVFASCGTDDLIYIQS      400
                |||||||||||||||||||||||||||||||||||||||||||||||||||
ID1        310 DIIKGIGIWILCGKEWREIARMPHKFFQGFGEFDDVFASCGTDDLIYIQS      359

ID7        401 YGAPALLTFDMNLRQWRWSQKCPVTKRFPLQLFTGFCFEPRLEINP      446
                |||||||||||||||||||||||||||||||||||||||||||||||
ID1        360 YGAPALLTFDMNLRQWRWSQKCPVTKRFPLQLFTGFCFEPRLEINP      405
```

WATERMELON GENE CONFERRING A HIGH NUMBER OF MALE FLOWERS

CROSS-REFERENCE TO RELATED APPLICATIONS

This application is a National Stage Entry of PCT/EP2022/056848, filed Mar. 16, 2022, which claims priority to European Patent Application No. 21171772.3, filed May 3, 2021, and U.S. Provisional Application No. 63/166,040, filed Mar. 25, 2021, the disclosures of each of which are hereby incorporated by reference in their entireties.

FIELD

The present invention is directed to watermelon plants comprising a mutation in an F-box gene, whereby the plant produces many male flowers and no female flowers (or few female flowers, e.g. at a late stage of the growing period) when the mutant allele of the gene is in homozygous form. As the plants do not produce female flowers (or only a few female flowers at a late stage), also no (or very few) fruit setting can take place on the plant. It is, therefore, ideal as pollenizer plant, to produce many male flowers and pollen for pollinating other watermelon plants.

The invention is, thus, directed at watermelon plants, seeds and plant parts comprising at least one, preferably two mutant alleles of the recessive gene, their use as pollenizer plants in watermelon cultivation and fruit production and methods of generating and/or selecting (or identifying) watermelon plants comprising at least one mutant allele of the gene. In one aspect selection can be done easily phenotypically, as leaf shape is modified in the homozygous mutant plant, at least in two genetic backgrounds, but maybe also in other backgrounds. Also the petals of the male flowers are fused together, although not in all cases and not in all backgrounds.

The F-box gene is herein referred to as ClHWS (for *Citrullus lanatus* HAWAIIAN SKIRT), as, when doing a BLAST analysis against the UniProt/SwissProt NCBI database, the most similar protein is At3g61590 (*Arabidopsis thaliana* F-box/kelch-repeat protein). Pairwise alignment of At3g61590 with ClHWS shows a sequence identity of only 65.5% (FIG. 2) and the phenotype conferred by At3g61590 mutants and the watermelon ClHWS mutant are very different, with few similarities, indicating that the genes may not be functionally the same in the different species.

F-box proteins constitute one of the largest superfamily of proteins in plants, with several hundred F-box genes in some species. In *Arabidopsis* at least 694 F-box genes have been identified. A review on plant F-box genes is provided by Xu et al., PNAS 2009 (vol. 106, no. 3, pp 835-840). Plant F-box genes play a role in protein ubiquitination and degradation and have been found genetically to control many crucial processes such as embryogenesis, hormonal responses, seedling development, floral organogenesis, senescence, and pathogen resistance.

BACKGROUND

Cultivated watermelon plants are generally monoecious, with separate male and female flowers developing on the plant. Male flowers contain stamen and produce pollen (they are often called staminate flowers). Female flowers contain ovaries and pistils (they are often called pistilate flowers). The ratio of male to female flowers vary but for most cultivars it is between 3:1 or 4:1 and 7:1, i.e. ranging from about 75% male flowers to about 25% female flowers (3:1 ratio) or from about 80% male flowers to about 20% female flowers (4:1 ratio), to about 87.5% male flowers to about 12.5% female flowers (7:1 ratio).

The present invention relates in one aspect to a recessive gene, which when mutated and present in homozygous form results in ratios of about 100% male flowers to 0% female flowers, or 99.5%:0.5%. 99%:1%, 98%:2%, 97%:3% male flowers to female flowers, optionally 96%:4%, or 95% to 5% male flowers to female flowers or about 92% to 8%, or about 91: to 9%, or about 90%:10%. Thus, in one aspect the invention relates to a recessive gene, which when mutated and present in homozygous form results in a 'larger ratio of male to female flowers', which refers to a statistically significant higher ratio of male flowers to female flowers developing over a specified period of time (e.g. 1, 2, 3 or more weeks) in the plant line homozygous for the mutant allele compared to the control line homozygous for the wild type allele.

In one aspect the percentage of male flowers produced by the plant homozygous for the mutant allele is thus significantly higher than for the plant homozygous for the wild type allele, e.g. at least 90%, 91%, 92%, 93%, 94%, 95%, 96%, 97%, 98%, 99%, 99.5% or 100% of the flowers that develop on the plant during a specified period (e.g. during week 4, 5 and/or 6 after transplantation into the field) or during the entire growing cycle of the plant are male flowers. The best way to compare the percentage of male flowers, or the ratio of male to female flowers, is to grow a plant which is homozygous for the mutant allele under the same conditions and for the same time next to a plant homozygous for the wild type allele and count the number of flowers that develop during a specific period, e.g. during one or more weeks. Preferably at least several plants of each genotype are grown in order to compare the average numbers of male and female flowers developing per genotype during the period.

Thus, in one aspect a higher or larger percentage of male flowers refers to a statistically significant higher percentage of male flowers developing over a specified period (e.g. 1, 2, 3 or more weeks) in the plant line homozygous for the mutant allele compared to the control line homozygous for the wild type allele. For example, at least 90%, 91%, 92%, 93%, 94%, 95%, 96%, 97%, 98%, 99% or even 100% of the flowers that develop are male flowers in the plant homozygous for the mutant Clhws allele, while in the control plant (homozygous for the wild type/non-mutant Clhws allele) the percentage of male flowers is significantly lower. E.g. in the Examples the mutant Clhws plant had (in two different backgrounds) 17% and 24% more male flowers than the control plant.

Watermelon plants are grown for fruit production are either diploid (2n), producing seeded fruits after pollination of the female flowers with pollen of the male flowers, or triploid (3n), producing seedless fruit after pollination of the female flowers with pollen from another watermelon plant (called a pollenizer plant), as the flowers of the triploid plants do not produce fertile pollen.

Thus, as the triploid plants do not produce fertile pollen so-called pollinator or pollenizer plants are planted in the same field, as pollination of the female flowers is required to induce fruit formation on the triploid plant. The pollenizer plants are diploid (2n). Generally a ratio of pollenizer to triploid plants of around 1 to 3 are planted in a given scheme for providing sufficient pollen for pollinating all the female flowers of the F1 hybrid plants. A further requirement is that the pollenizer plants produce large amounts of pollen during the time when the female flowers of the triploid plants are developed. McGregor and Waters (2014, Hort Science 49(6): 714-721) have analysed the synchronization of staminate flower production of 20 pollenizers and pistilate flowers of 29 triploid varieties during the first 6 weeks after transplant into the field and concluded that some pollenizers and triploids are better synchronized in flowering characteristics than others.

Commercial pollenizers can be distinguished as being harvestable or non-harvestable pollenizers (see also McGregor and Waters 2014, supra). Harvestable pollenizers are diploid pollenizers, which produce marketable, seeded fruits upon pollination of the female flowers. Non-harvestable pollenizers are diploid pollenizers which produce agronomically undesirable fruits upon pollination of the female flowers, such as white fleshed fruits, fruits having a brittle rind, etc. A grower can thus choose to produce triploid, seedless fruits and diploid, seeded fruits in one field, or to only produce triploid, seedless fruits and discarding the diploid, seeded fruits of the pollenizer. Obviously pollenizers take up a lot of space in the field, which can otherwise be occupied by triploid plants, and for this reason several pollenizers have been developed which produce compact plants.

All commercial pollenizers produce fruits (either harvestable or non-harvestable), as they all produce female flowers which are pollinated. One advantage of the ClHWS gene described herein is that the watermelon plants which comprise a mutant allele of the gene in homozygous form do not produce female flowers (or produce few female flowers, which are generally not fertilized and do not produce fruits) but produce many male flowers and large amounts of pollen during the growing season. Also, as no or very few female flowers are produced, the plant continues to produce male flowers for longer. There is, therefore, no need to harvest or to discard fruits that develop on the pollenizer plants. Also fewer pollenizer plants are required in a field (a decrease of at least 5%, 10%, 15%, 20% or even 25% of pollenizer plants) in order to produce sufficient pollen for pollinating the triploid plants, whereby more triploid plants can be grown per area and more triploid fruits can be harvested from a field.

The present inventors have found that mutating a single recessive gene in cultivated watermelon, referred herein to as the ClHWS gene, results in the watermelon plants developing only male flowers (optionally few female flowers, e.g. at a later stage in cultivation, which are generally not fertilized). The many male flowers are fully fertile and produce large amounts of pollen. The gene was found after finding a mutant plant having abnormal leaf shape in a mutant watermelon population (Tilling population). FIG. 3 shows the leaf shape of the mutant plant on the left and the leaf of the wild type/non-mutant plant on the right.

This leaf shape phenotype was mapped in an F2 mapping population and led to the identification of the ClHWS gene on chromosome 5. In the mutant plant there was a premature STOP codon in the coding region (also referred to herein as the Trp204STOP or W204* mutant), leading to a truncated protein being made, see FIG. 1, showing an alignment of the mutant Clhws protein (indicated as 'Mutant') and the wild type ClHWS protein (indicated as 'WT').

Besides the abnormal (or 'modified' or 'broader lobed') leaf shape, the mutant plant also did not develop female flowers but only male flowers. The male flowers had fused petals (see FIG. 4, left hand), which still enables insects to enter the flowers to collect pollen. When occasionally few female flowers did develop, e.g. later in the growing period, the female flowers were generally not pollinated and did not set fruits. Also male flowers continued to develop over a longer period.

When the mutant Clhws allele was combined with another recessive gene called 'multibranching', the percentage and number of male flowers was increased even further, see Example 2. Therefore, plants comprising both a mutant Clhws allele in homozygous form (as described herein) and a mutant multibranching allele in homozygous form is, therefore, one embodiment of the invention. Mutant multibranching alleles are described in application U.S. 63/217, 071 and EP21194565.4, which are incorporated herein by reference. Further, one mutant multibranching allele is the allele found in variety Sidekick, which contains the allele encoding the mutant multibranching protein of SEQ ID NO: 9. The multibranching protein of SEQ ID NO: 9 comprises a duplication of 8 amino acids compared to the wild type protein of SEQ ID NO: 11. The mutant multibranching allele of variety Sidekick is also described in U.S. Pat. No. 7,314,979B2, incorporated herein by reference. This particular allele is also present in other watermelon seeds, deposited by Nunhems B.V. as described e.g. in U.S. application Ser. No. 16/705,760 (published as US 2020/0 093086 A1), incorporated herein by reference. For example, accession NCIMB 41773 (WH9307), or accession number NCIMB 42704 (WH9716) contain the mutant multibranching allele in homozygous form.

As mentioned. BLAST analysis resulted in the identification of a gene called HAWAIIAN SKIRT of *Arabidopsis thaliana* (abbreviated AtHWS). The Athws mutant is characterized in Zinnia et al. 2007 (Plant Physiology Vol. 144, pp 1370-1382). The hws-1 mutant plant failed to shed its reproductive organs (sepals, petals and anther filaments), the sepals were fused at the lower margins and floral organs remained attached at the base to the developed pods (siliques), containing the seeds, seen in FIG. 1F and FIG. 5F. Also anther filaments were often fused to each other or to the silique and some had aberrant pods with siliques containing more than two valves. Another phenotype seen was that the hws-1 mutant had larger leaves and larger seeds than the normal plant, when grown under the same conditions.

The AtHWS gene encodes a protein of 411 amino acids, with no introns in the open reading frame, but an intron in the 5'UTR. The hws-1 mutant contained a truncated protein (FIG. 5B), which is believed to be non-functional if expressed. The AtHWS gene is expressed in many tissues, such as cotyledon margins, sepals, stigma, silique, base of petals and sepals, anther filaments, pollen, floral leaves, cauline leaves, developing seed, tissue of the roots, etc. Reasons for this protein having being an F-box protein came from studies in a yeast two hybrid system, in which AtHWS was associated with ASK proteins (see page 1377, LH paragraph of Zinnia et al. supra), while the AtHWS gene only has a low sequence similarity to the other 700 F-box superfamily members in *Arabidopsis* (which were assigned to be members of the F-box family based on sequence similarity). Functional characteristics are commonly assigned to newly identified genes (e.g. identified in whole genome sequencing projects) based on sequence similarity, without in vivo evidence.

The present ClHWS gene encodes an F-box protein and the plant homozygous for the mutant, truncated protein identified herein develops a higher percentage of male flowers and is very suitable as a pollenizer plant. This in vivo evidence establishes a role of the protein in flower development. Based on the low sequence identity to AtHWS and the differences in phenotype, the naming of the present protein as ClHWS is, thus, not based on any evidence of similar functional roles of the *Arabidopsis* and the watermelon HWS F-box proteins.

Thus, when the mutant Clhws allele is present in homozygous form in a diploid watermelon plant, indicated herein as Clhws/Clhws, the plants produce a higher percentage of male flowers and optionally leaves which have a different (abnormal or 'modified' or 'broader lobed') shape than the plant homozygous for the wild type allele (ClHWS/ ClHWS). The mutant Clhws protein of SEQ ID NO: 2, encoded by the mutant Clhws allele wherein codon TGG encoding W or Trp (nucleotides 610 to 612 of SEQ ID NO: 3 or 4) is changed into codon TAG (translation stop codon), is only 203 amino acids in length and lacks 202 amino acids of the wild type protein. This mutant is herein also referred to as Trp204* or W204* or W204STOP. Three-dimensional structure prediction showed that the W204* mutant lacked most of the C-terminal beta sheets of the wild type protein (see FIG. 5, showing the wild type protein). It is, therefore, believed that the truncated protein is non-functional in vivo, even though the F-box domain is not changed. This means that any mutant allele, which results in no wild type protein being made or which results in a non-functional protein being made will result in the phenotype as seen herein for the identified Trp204* mutant.

Therefore, in one aspect a watermelon plant or plant part comprising at least one copy of a mutant Clhws allele is provided herein, wherein the mutant allele comprises a reduced expression or no expression (e.g. due to mutations in the promoter or other regulatory element) resulting in a significantly reduced level or no wild type protein being made, or comprises one or more amino acids inserted, deleted or replaced with respect to the wild type protein of SEQ ID NO: 1 (or a wild type protein comprising at least 90%, 91%, 92%, 93%, 94%, 95%, 96%, 97%, 98% or 99% sequence identity to SEQ ID NO: 1), resulting in the encoded protein having reduced function or no function in vivo, when the mutant allele is present in homozygous form in a diploid watermelon plant.

In the Charleston Grey reference genome of watermelon (world wide web at cucurbitgenomics.org) the wild type gene is found on chromosome 5 starting at base 1109369 and ending at base 1110586. In the reference genome of variety 97103 v2 the wild type gene is found on chromosome 5 starting at base 1045193 and ending at base 1046410. Both genomic sequences are identical and are also included herein as SEQ ID NO: 4. As no intron is present, the cDNA of SEQ ID NO: 3 is identical to the genomic DNA of SEQ ID NO: 4.

It should be noted that in these reference genomes there is a gene annotated in the same region, but starting 1187 nucleotides further upstream (and comprising an intron) and encoding the protein of SEQ ID NO: 7. This gene, named ClCG05G000990, is most likely wrongly annotated (see Examples). The genomic sequence encoding the protein ClCG05G000990 of SEQ ID NO: 7 is provided in SEQ ID NO: 8. This sequence thus also comprises SEQ ID NO: 4, which starts at nucleotide 1188 of SEQ ID NO: 8. In the annotation of ClCG05G000990 there is an exon from nucleotide 1 to 129 of SEQ ID NO: 8, an intron from nucleotide 130 to 1193 of SEQ ID NO: 8 and an exon from nucleotide 1194 to 2405 of SEQ ID NO: 8, resulting in the protein ClCG05G000990 of SEQ ID NO: 7.

The wild type and mutant ClHWS proteins are shown in FIG. 1. The conserved F-box domain is highlighted in bold.

Even though all of the conserved F-box domain is present in the truncated Clhws protein, it is highly unlikely that the truncated protein will have a function in vivo, and it is assumed that the mutation is a loss-of-function allele. As mentioned, the presence of this mutant Clhws allele in homozygous form in a diploid watermelon plant leads to the plant producing a higher percentage of male flowers than the wild type plant and mostly no fruit setting or fruit development on the plant. Also leaf shape was found to be modified (FIG. 3, left and FIG. 7, left) e.g. to be more broadly lobed and petals of the male flowers were often, but not always, fused in certain genetic backgrounds (FIG. 4) while they were e.g. not fused in other backgrounds, see FIG. 8 (but male flowers may still look different/have a different appearance than wild type male flowers, see FIG. 8, left mutant and right wild type male flower), making selection of watermelon plants comprising a mutant Clhws allele very easy by phenotypic selection (e.g. based on leaf shape and/or male flower appearance), at least in certain genetic backgrounds.

Figure 7:

The abnormal or 'modified' or 'broader lobed' leaf shape seen in the original mutant was also seen when the mutant Clhws allele was transferred to a different genetic background, as shown in FIG. 7, where the left hand foto shows the leaf of the mutant Clhws plant and on the right-hand side the leaf shape of the wild type plant lacking the mutant Clhws allele. The broader lobed leaf shape, therefore, appears to be due to the presence of the mutant Clhws allele in homozygous form. It is not yet clear if the broader leaf shape is seen in all genetic backgrounds, which is why this characteristic is optional in the plant comprising the mutant Clhws allele.

Furthermore, another mutant allele, W229*, also showed the broader lobed leaf shape in young plants, see Example 3. As the W204* mutant and the W229* mutant result in truncated proteins which lack 202 and 177 amino acids, respectively, of the wild type protein, it is concluded that these proteins are non-functional in vivo and that (at least) any mutation which leads to a non-functional protein (loss-of-function protein) or whereby the wild type protein is not expressed (knock-out mutant) will confer the phenotype of producing a higher percentage of male flowers (or higher ratio of male to female flowers).

The wild type ClHWS protein shown in SEQ ID NO: 1 is 405 amino acids long and comprises three distinct regions, the N-terminal region from amino acid 1 to 44, the conserved F-box domain from amino acid 45 to 83 and the C-terminal region, which folds into a large number of beta-sheets, starting at amino acid 93 and ending at amino acid 380. The predicted three-dimensional structure of the protein is shown in FIG. 5.

Further mutants have been generated having mutations in the endogenous ClHWS allele and their phenotype will be confirmed by generating a plant homozygous for the mutant allele. The following mutants have been identified so far:

TABLE A

| SNP | Codon change | Change in protein of SEQ ID NO: 1 | Protein region affected | Phenotype observed in homozygous plants |
|---|---|---|---|---|
| G/A | TGG (W), TAG (STOP) | W204Stop | C-terminal beta sheets | Mainly male flowers, modified leaf shape and fused petals |
| G/A | GGG (G), GAG (E) | G340E | C-terminal beta sheets | Not tested |
| G/A | GCT (A), ACT (T) | A362T | C-terminal beta sheets | Not tested |

TABLE A-continued

| SNP | Codon change | Change in protein of SEQ ID NO: 1 | Protein region affected | Phenotype observed in homozygous plants |
|---|---|---|---|---|
| G/A | TGG (W), TGA (Stop) | W229Stop | C-terminal beta sheets | Modified leaf shape, see Example 3 (mainly male flowers to be determined) |
| G/A | GAG (E), AAG (K) | E324K | C-terminal beta sheets | Not tested |
| C/T | TCT (S). TTT (F) | S67F | F-box domain | Not tested |
| G/A | AGC (S), AAC (N) | S348N | C-terminal beta sheets | Not tested |
| G/A | GGA (G), GAA (E) | G228E | C-terminal beta sheets | Not tested |
| C/T | CTT (L), TTT (F) | L242F | C-terminal beta sheets | Not tested |
| G/A | AGA (R), AAA (K) | R64K | F-box domain | normal (wild type) leaf shape |
| G/A | GTT (V), ATT (I) | V219I | C-terminal beta sheets | Not tested |
| G/A | TGC (C), TAC (Y) | C69Y | F-box domain | Not tested |

Therefore, one aspect herein is a watermelon plant, plant part or seed comprising at least one mutant allele of the ClHWS gene, whereby the mutant allele results in a phenotypic features of i) only male flowers developing or a larger percentage of male flowers developing or a larger ratio of male to female flowers developing than on the homozygous wild type plant, and optionally further one or more phenotypic features selected from ii) male flowers frequently but not always having fused petals and/or male flowers having a different appearance and iii) the plant having differently shaped leaves than the wild type, when the mutant allele is in homozygous form, due to either a mutant protein being produced which has reduced function or loss of function compared to the wild type ClHWS protein, or due to the mutant allele having reduced gene expression or no gene expression compared to the wild type ClHWS allele, resulting in less or no functional wild type ClHWS protein being made in the plant.

A mutant Clhws allele may, thus, comprise one or more amino acids inserted, deleted or replaced compared to the wild type ClHWS protein, or a mutant Clhws allele may comprise one or more mutations in a regulatory region of the protein, such as a promoter or enhancer, resulting in reduced or no functional wild type protein being made, which would thereby equally result in the phenotypic feature (when the mutant allele is in homozygous form in a diploid) of i) only male flowers developing or a larger percentage of male flowers developing or a larger ratio of male to female flowers developing than in the homozygous wild type and optionally further one or both of the following phenotypic features: ii) male flowers frequently but not always having fused petals and/or male flowers having a different appearance and iii) the plant having differently shaped leaves.

In one aspect the mutant allele comprises one or more amino acids replaced, inserted and/or deleted in the conserved F-box domain (amino acids 45 to 83 of SEQ ID NO: 1 or the equivalent amino acids of a protein comprising at least 90% sequence identity to SEQ ID NO: 1) and/or in the region of the C-terminal beta sheets (amino acids 93 to 380 of SEQ ID NO: 1 or the equivalent amino acids of a protein comprising at least 90% sequence identity to SEQ ID NO: 1).

Regarding mutations in the F-box domains (or in other parts of the protein), in one aspect especially mutations which lead to amino acid replacements, whereby the properties of the wild type amino acid and the replaced amino acid are different, are one aspect herein, as such different amino acid properties will reduce or abolish the proper folding and/or the normal function of the protein or of the domain. So, for example a replacement of a non-polar amino acid by a polar amino acid (comprising a hydrophilic side chain), or vice versa, or the replacement of an amino acid having a charged side chain with a non-charged or differently charged side-chain, or vice versa. Non-polar amino acids are Alanine (A or Ala), Cysteine (C or Cys), Glycine (G or Gly), Isoleucine (I or Ile), Leucine (L or Leu), Methionine (M or Met), Phenylalanine (F or Phe), Proline (P or Pro), Tryptophan (W or Trp), Valine (V or Val). Polar amino acids are Arginine (R or Arg), Asparagine (N or Asn), Aspartate (D or Asp), Glutamate (E or Glu), Glutamine (Q or Gln), Histidine (H or His), Lysine (K or Lys), Serine (S or Ser), Threonine (T or Thr), Tyrosine (Y or Tyr).

Thus, in one aspect any one (or more) of the non-polar amino acids of the F-box domain (L, P, I, A, F, G, V, C, W) are replaced by a polar amino acid (D, E, R, S, Y, T, K, H) and/or any one (or more) of the polar amino acids of the F-box domain are replaced by a non-polar amino acid. The resulting mutant allele can then be tested for its function by generating a plant homozygous for the mutant allele and analyzing the phenotype. If the mutant allele results in the plant having modified phenotypic characteristics with i) only male flowers developing or a larger percentage of male flowers or a larger ratio of male to female flowers developing than in the homozygous wild type and further optionally ii) male flowers frequently but not always having fused petals and/or a different appearance and/or iii) the plant having differently shaped leaves, when the mutant allele is in homozygous form in a diploid plant, then the mutant allele is an allele encodes a mutant ClHWS protein having reduced function or no function in vivo.

In another aspect the mutant Clhws allele encodes a truncated protein, whereby at least 20, 30, 40, 50, 60, 70, 80, 90, 100, 110, 120, 130, 140, 150, 160, 170, 177, 180, 190, 200, 201, 202, 203, 204, 205, 206, 207, 208, 209, 210, 211, 212, or more amino acids of the C-terminal end of the wild type ClHWS protein are missing or are optionally replaced by different amino acids, rendering the protein to have a reduced in vivo function or no in vivo function.

In a different aspect the mutant Clhws allele encodes a truncated protein, whereby at least 1, 2, 3, 4, 5, 6, 7, 8, 9, 10, 20, 30, 40, 50, 60, 70, 80, 90, 100, 110, 120, 130, 140, 150, 160, 170, 177, 180, 190, 200, 201, 202, 203, 204, 205, 206, 207, 208, 209, 210, 211, 212, 220, 225, 250, 300, 301, 302, 303, 304, 305, 306, 307, 308, 309, 310, 311 or more amino acids are inserted into, or are replaced or deleted from the wild type ClHWS protein, rendering the protein to have a reduced in vivo function or no in vivo function.

In a further aspect the mutant Clhws allele encodes a mutant protein, whereby one or more amino acids of the F-box domain of the wild type ClHWS protein are deleted or are optionally replaced by different amino acids, or comprising an insertion of one or more amino acids in the F-box domain, rendering the protein to have a reduced in vivo function or no in vivo function. The F-box domain is the domain starting at amino acid 45 and ending at amino acid 83 of SEQ ID NO: 1.

In one aspect the functional (or wild type) watermelon ClHWS gene is the gene encoding a ClHWS protein, wherein a ClHWS protein is the protein of SEQ ID NO: 1 or a protein comprising at least 90%, 91%, 92%, 93%, 94%, 95%, 96%, 97%, 98% or 99% sequence identity to SEQ ID NO: 1 (referred to as a functional variant). Functional variants of the protein of SEQ ID NO: 1 do, in one aspect, comprise an F-box domain which is 100% identical to the F-box domain of SEQ ID NO: 1. The slight amino acid sequence variation is, therefore, in a specific aspect found outside of the conserved F-box domain.

Thus, other cultivated watermelons may contain an allelic, functional variant of the ClHWS gene, having at least 90%, 91%, 92%, 93%, 94%, 95%, 96%, 97%, 98% or 99% nucleotide sequence identity to SEQ ID NO: 4, and may encode a wild type (functional) ClHWS protein having at least 90%, 91%, 92%, 93%, 94%, 95%, 96%, 97%, 98% or 99% sequence identity to SEQ ID NO: 1. As mentioned, such proteins are herein also referred to as functional variants of the protein of SEQ ID NO: 1 and such genes are referred to as allelic variants of the gene of SEQ ID NO: 4. Importantly, they should lead to the modified phenotypic characteristic (described elsewhere) when mutated to either knock-down or knock-out gene expression or when mutated to encode a reduced function or loss of function protein. E.g. an allelic variant into which the same mutation is introduced as generated herein, such as the single nucleotide change (G to A) of nucleotide 611 of SEQ ID NO: 4 (leading to codon TGG being changed into codon TGA, i.e. W204STOP), should give the same phenotype when present in homozygous form in a diploid plant.

In one aspect of the invention a plant or plant cell is provided, characterized in that the plant or plant cell has decreased activity of a ClHWS protein compared to a corresponding wild type plant cell, wherein the ClHWS protein of the wild type plant cell is encoded by nucleic acid molecules selected from the group consisting of:

a) nucleic acid molecules, which encode a protein with the amino acid sequence given under SEQ ID NO: 1 (watermelon);

b) nucleic acid molecules, which encode a protein, the sequence of which has an identity of at least 90%, 91%, 92%, 93%, 94%, 95%, 96%, 97%, 98% or 99% with the amino acid sequence given under SEQ ID NO: 1 (watermelon);

c) nucleic acid molecules, which encode a protein, the sequence of which has an identity of at least 90%, 91%, 92%, 93% 94%, 95%, 96%, 97%, 98% or 99% with the amino acid sequence given under SEQ ID NO: 1 (watermelon) and wherein the protein comprises the amino acid sequence of the F-box domain of amino acids 45 to 83 of SEQ ID NO: 1;

d) a nucleic acid molecule of SEQ ID NO: 3 or SEQ ID NO: 4 or a sequence comprising at least 90%. 91%, 92%, 93%, 94%, 95%, 96%, 97%, 98% or 99% sequence identity to SEQ ID NO: 3 or to SEQ ID NO:4 and encoding a ClHWS protein:

e) a nucleic acid molecule comprising or consisting of SEQ ID NO: 4 or comprising or consisting of SEQ ID NO: 8 and encoding a ClHWS protein of SEQ ID NO: 1 or of SEQ ID NO: 7.

The decreased activity of the ClHWS protein is caused by a mutant Clhws allele. Decreased activity may be caused by a knock-down or knock-out of the expression of the mutant Clhws allele (e.g. through a mutation in the promoter or other regulatory sequence) or through the mutant Clhws allele encoding a loss-of-function or decreased-function Clhws protein (mutant Clhws protein).

In one aspect the mutant Clhws allele encodes a mutant Clhws protein having decreased function or loss-of-function compared to the wild type protein, e.g. the mutant Clhws protein comprises one or more amino acids replaced, deleted and/or inserted compared to the wild type protein.

In one aspect the mutant Clhws protein comprises one or more amino acids replaced, deleted and/or inserted in a region of the protein selected from the group: a) the conserved F-box domain of the protein, and b) the region starting at amino acid 84 or 93 and ending at amino acid 380, especially starting at amino acid 93 and ending at amino acid 380, especially in the region of the C-terminal beta sheets and c) lacking at least 10, 20, 30, 40, 50, 60, 70, 80, 90, 100, 110, 120, 130, 140, 150, 160, 170, 180, 190, 200, 201, 202, 203, 204, 205 or more of the wild type amino acids at the C-terminal end of the protein.

In one aspect, at least one amino acid is replaced by another amino acid or by a STOP codon, resulting in a loss of function or decreased function protein and the phenotypic change (as e.g. described above) when the allele is in homozygous form (when no wild type allele is present in the diploid plant or plant cell).

In another aspect one or more amino acids are missing, e.g. through a mutation causing a premature STOP codon, resulting in a loss of function or decreased function protein and the phenotypic changes (as e.g. described above) when the allele is in homozygous form (when no wild type allele is present in the diploid plant or plant cell).

In one aspect the mutant allele encodes a protein comprising an amino acid change in the wild type ClHWS protein of SEQ ID NO: 1 as shown in Table A, or the equivalent amino acid change in a wild type protein comprising at least 90% identity to SEQ ID NO: 1. The equivalent amino acid in a sequence comprising at least 90% sequence identity to SEQ ID NO: 1 can easily be identified by pairwise alignment of the proteins using e.g. the program Needle (using default parameters). For example, W204 in SEQ ID NO: 1 corresponds to W245 in SEQ ID NO: 7: SEQ ID NO: 1 and SEQ ID NO: 7 have 90.4% sequence identity to each other and it is only the N-terminal region which is different. FIG. 6 shows the mutants of Table A in SEQ ID NO: 1 in bold and the equivalent amino acid in SEQ ID NO: 7 (also in bold). Should SEQ ID NO:7 be a real protein and not an annotation error, mutants whereby the protein has a reduced function or loss of function (as described herein for the protein of SEQ ID NO: 1 and other wild type proteins comprising at least 90% sequence identity to SEQ ID NO: 1) are herein encompassed.

In one aspect the mutant protein is truncated, missing at least 10, 20, 30, 40, 50, 60, 70, 80, 90, 100, 110, 120, 130, 140, 150, 160, 170, 177, 180, 190, 200, 201, 202, 203, 204, 205, 206, 207, 208, 209, 210, 211, 212, or more amino acids of the C-terminal end of the wild type ClHWS protein of SEQ ID NO: 1 (or of a wild type protein comprising at least 90% identity to SEQ ID NO: 1) are missing or are optionally replaced by one or more different amino acids, rendering the protein to have a reduced in vivo function or no in vivo function.

In one aspect the W (Trp) at position 204 or at position 229 of SEQ ID NO: 1, or at the equivalent position of a protein comprising at least 90% identity to SEQ ID NO: 1, is deleted, or replaced by a different amino acid, or is replaced by a stop codon. In one aspect the W (Trp) at position 245 or at position 270 of SEQ ID NO: 7 or at the equivalent position of a protein comprising at least 90% identity to SEQ ID NO: 7, is deleted, or replaced by a different amino acid, or is replaced by a stop codon.

The equivalent amino acid can be easily identified in a pairwise alignment between both proteins, e.g. the protein of SEQ ID NO: 1 and the protein comprising at least 90% sequence identity to SEQ ID NO: 1, using pairwise alignment tools, such as Emboss 'Needle' (using default parameters).

A reduced function or a loss-of function of the protein is present when the mutant allele changes the in vivo phenotype from the wild type phenotype. i.e. production of male and female flowers in certain ratios, normal leaf shape and petals not being fused when the wild type allele is present in homozygous form, into a modified phenotype of i) only male flowers developing or a larger percentage of male flowers developing or a larger ratio of male to female flowers developing than in the homozygous wild type, and further optionally ii) male flowers frequently but not always having fused petals or male flowers having a different appearance and/or iii) the plant having differently shaped leaves, when the mutant allele is in homozygous form in a diploid plant.

The equivalent amino acids in a sequence comprising at least 90%, 91%, 92%, 93%, 94%, 95%, 96%, 97%, 98% or more sequence identity to SEQ ID NO: 1 can be identified by pairwise alignment (e.g. using the program Needle) with SEQ ID NO: 1. The equivalent amino acid of the W204 of SEQ ID NO: 1 can for example easily be identified in a sequence comprising at least 90% sequence identity to SEQ ID NO: 1 or even in the *Arabidopsis* AtHWS protein of only 65.5% sequence identity to SEQ ID NO: 1, see FIG. 2.

In one aspect W204 or the W229 of the watermelon protein of SEQ ID NO: 1 (or the equivalent amino acid in a sequence comprising at least 90%, 91%, 92%, 93%, 94%, 95%, 96%, 97%, 98% or more sequence identity to SEQ ID NO: 1), is replaced by a different amino acid, is deleted or is replaced by a stop codon.

SUMMARY

A cultivated watermelon plant or plant part is provided comprising at least one copy of a mutant allele of a gene named ClHWS, said mutant allele conferring a phenotypic change of i) only male flowers developing or a larger percentage of male flowers or a larger ratio of male to female flowers developing than on the homozygous wild type plant and further optionally ii) male flowers frequently, but not always, having fused petals or male flowers having a different appearance and/or iii) the plant having differently shaped leaves (e.g. more broadly lobed leaves), when the mutant allele is in homozygous form in a diploid plant.

In one aspect the gene is located on chromosome 5 of the watermelon genome, especially the gene is located in a region starting at base 1109369 and ending at base 1110586 of chromosome 5 of the Charleston Grey chromosome.

In one embodiment the plant or plant part or seed comprising the mutant allele of the ClHWS gene is diploid, tetraploid, triploid or polyploid. Preferably the mutant allele is present in two copies in a diploid plant or plant part or seed. Optionally it may be present in four copies in a tetraploid plant or plant part or seed, or in one, two or three copies in a triploid plant or plant part or seed.

The plant part comprising the mutant allele of the ClHWS gene may be a cell, a flower, a leaf, a stem, a cutting, pollen, a root, a rootstock, a scion, a fruit, a protoplast, an embryo, an anther.

Also encompassed is a vegetatively propagated watermelon plant propagated from such a plant part comprising at least one mutant allele of the ClHWS gene.

Likewise a seed from which a plant of the invention can be grown is provided.

Further, male flowers, anthers and pollen produced by a plant according to the invention is provided.

A method of producing seedless watermelon fruits is provided, said method comprising growing a diploid (pollenizer) plant comprising two copies of a mutant allele of a ClHWS gene in the vicinity of a triploid plant and harvesting the fruits produced by said triploid plants. In particular the fruits develop after pollination of the female flowers of the triploid plant with pollen of the diploid pollenizer plant (comprising two copies of a mutant allele of a ClHWS gene).

Interplanting of pollenizer and triploid plants in one field may be either done by seeding or transplants of the pollenizer and triploids. Various interplanting methods can be used, as known in the art and various ratios of pollenizer: triploid hybrid may be used. One row of pollenizer plants may for example be present at least every 2, at least every 3, or at least every 4, or at least every 5 rows of triploids, but other methods of interplanting may also be used. As the pollenizer does not set fruit itself due to the lack (or very low number) of female flowers, and as the male flowers are produced for an extended period after transplanting (e.g. more than 6, 7, 8, 9, 10 weeks after transplanting), the entire field requires less pollenizer plants and more triploid hybrids can be grown. The overall yield of seedless fruits is higher per hectare. Also, there is no need to remove or separate or plow under any diploid fruits, as these are not produced.

In one aspect the pollenizer plant comprises both a mutant Clhws allele in homozygous form and a mutant multibranching allele in homozygous form. This combination results in a very high number of male flowers and a 'multibranching' growth type of the plant, which is more compact and uses less space in the field or greenhouse. This pollenizer is a preferred pollenizer e.g. when interplanting in the field. Thus, in one aspect a mutant Clhws allele as described herein, especially a mutant Clhws allele which is a knock-out or loss-of-function allele (no expression of the allele or encoding a non-functional Clhws protein, e.g. a truncated protein) is combined with a mutant multibranching allele, e.g. with the mutant allele of SEQ ID NO:10, encoding the mutant protein of SEQ ID NO: 9, or another mutant multibranching allele which results in a multibranching phenotype when in homozygous form. Preferably both the mutant Clhws allele and the mutant multibranching allele are in homozygous form, to result in a high percentage of male flowers developing and the plant having a multibranching growth type.

A method of producing seedless watermelon fruits is provided, said method comprising growing a triploid plant and a diploid pollenizer plant comprising two copies of a mutant allele of a ClHWS gene, and in one aspect further comprising two copies of a mutant multibranching allele, allowing pollination of the flowers of the triploid plant and optionally harvesting the seedless triploid fruits.

A method for growing watermelon plants is provided, comprising growing a diploid watermelon plant comprising two copies of a mutant allele of a ClHWS gene and in one aspect further comprising two copies of a mutant allele of the multibranching gene, especially in a field or in a greenhouse or tunnel with other watermelon plants comprising female flowers, and optionally harvesting the watermelon fruits produced from said female flowers.

A method for production of a cultivated watermelon plant producing only male flowers or producing a higher percentage of male flowers (compared to a plant homozygous for the wild type ClHWS gene) is provided comprising the steps of:

a) introducing random or targeted mutations into one or more watermelon plants, plant parts or seeds; or providing a population of mutant plants or seeds (e.g. a TILLING population).

b) selecting a plant comprises a mutant allele of a ClHWS gene, especially a mutant allele which produces significantly reduced or no wild type ClHWS protein (e.g. a knock-out allele) or which produces a reduced function or loss of function mutant ClHWS protein (e.g. a truncated protein), c) optionally removing any transgenic construct (e.g. CRISPR construct) from the plant.

As plants which are homozygous for the mutant Clhws allele do not produce female flowers (or a very low percentage of female flowers, e.g. late during the growing season), other methods have to be used to produce seeds of the plants. In one aspect a diploid watermelon plant which is homozygous for the mutant Clhws allele is used as male parent to pollinate a diploid female parent plant which is heterozygous for the mutant Clhws allele. The seeds are collected from this cross. 50% of the seeds are homozygous for the mutant Clhws allele. This method is encompassed herein. Optionally the female parent is male sterile. In one aspect non-destructive seed genotyping or seed selection methods are used to separate seeds which are homozygous for the mutant Clhws allele from other seeds or for enriching a seed lot for seeds which are homozygous for the mutant Clhws allele.

Figure 8:
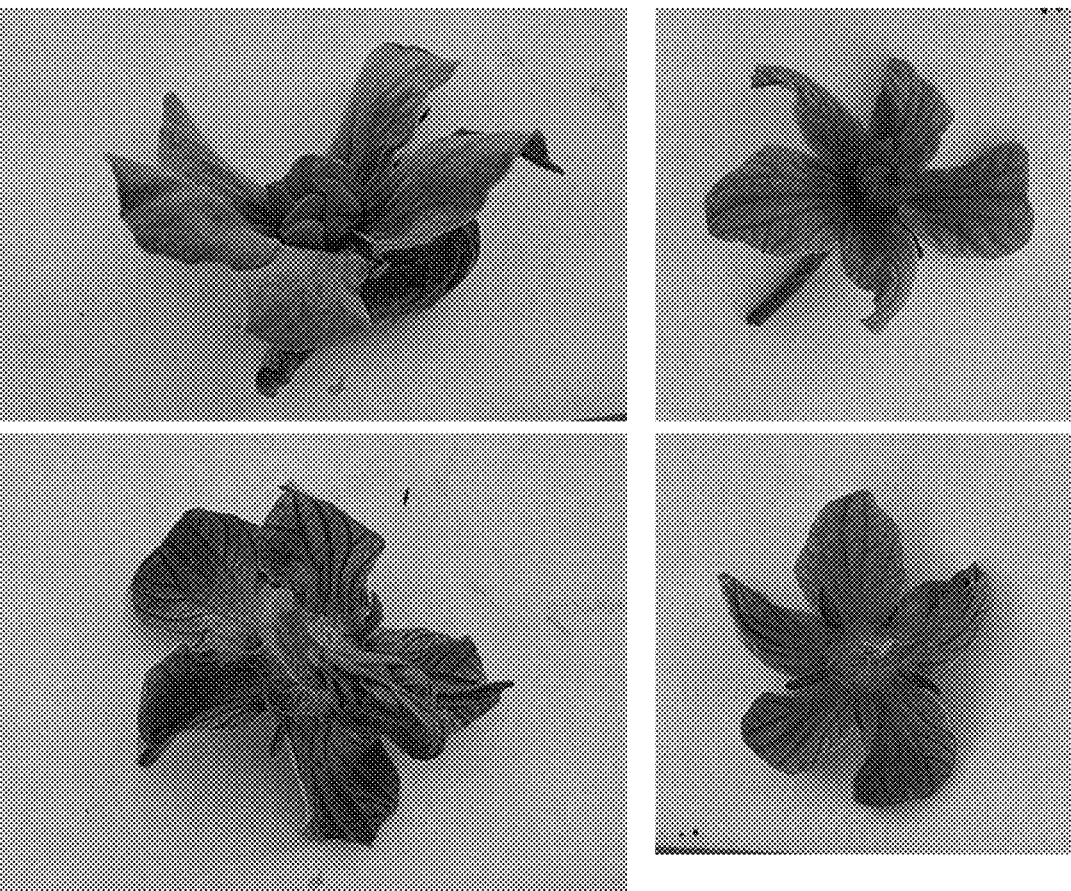

A method for selecting watermelon plants is provided comprising the steps of:

a) selecting plants which produce leaves having an abnormal or 'modified' or 'broader lobed' leaf shape as e.g. shown in FIG. 3 or FIG. 7, left side; and/or which produce only male flowers or a larger percentage of male flowers, and/or which produce male flowers having fused petals as shown in FIG. 4 (left) or different flower appearance as shown in FIG. 8 (left), and optionally b) confirming that the selected plants comprise a mutant Clhws allele in homozygous form on the locus on chromosome 5.

The selected plants may e.g. be put into trays together and sold as pollenizer plants.

Step b) may be carried out on the starting material, e.g. for the male parent of a cross with a female parent which is heterozygous for the mutant allele. If the plants are selected from a population of seeds produced by crossing a male parent (homozygous for the mutant allele) with a female parent (e.g. heterozygous for the mutant allele), then only step a) can be carried out by itself.

Use of a mutant Clhws allele of a ClHWS gene as described herein for producing of watermelon plants, plant parts or fruits is also an aspect of the invention.

General Definitions

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc. Similarly, "a fruit" or "a plant" also refers to a plurality of fruits and plants.

As used herein, the term "plant" includes the whole plant or any parts or derivatives thereof, preferably having the same genetic makeup as the plant from which it is obtained, such as plant organs (e.g. harvested or non-harvested fruits, leaves, flowers, anthers, etc.), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants, such as plant cuttings, embryos, pollen, anthers, ovules, fruits (e.g. harvested tissues or organs), flowers, leaves, seeds, clonally propagated plants, roots, stems, root tips, grafts (scions and/or root stocks) and the like. Also any developmental stage is included, such as seedlings, cuttings prior or after rooting, etc. When "seeds of a plant" are referred to, these either refer to seeds from which the plant can be grown or to seeds produced on the plant, after self-fertilization or cross-fertilization.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, e.g. the ClHWS locus (where the ClHWS gene is located: the alleles of the gene may be wild type alleles designated ClHWS, or mutant alleles designated Clhws), all of which alleles relate to one trait or characteristic at a specific locus (e.g. male flowering). In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous), e.g. two identical copies of the mutant Clhws allele (i.e. Clhws/Clhws) or one copy of the mutant Clhws allele and one copy of the wild type allele (i.e. Clhws/ClHWS). Likewise a triploid plant is referred to as homozygous for the gene if it has three identical alleles of a gene (e.g. three copies of the mutant Clhws allele, i.e. Clhws/Clhws/Clhws) and a tetraploid plant is referred to as homozygous for the gene if it has four identical alleles of the gene, e.g. four copies of the mutant Clhws allele.

"ClHWS gene" is a single, recessive gene identified in cultivated watermelon on chromosome 5, which when mutated results in a phenotypic change of i) only male flowers developing or a larger percentage of male flowers developing or a larger ratio of male to female flowers developing than in the homozygous wild type plant, and further optionally ji) male flowers frequently but not always having fused petals or a different male flower appearance and/or iii) the plant having differently shaped leaves, e.g. more broadly lobed leaves or a 'modified leaf shape', ClHWS is the wild type (WT), functional allele as present in normal cultivated watermelon plants (developing both male and female flowers on the plant in certain ratios, having petals which are not fused and having normal leaf shape) and Clhws is the mutant allele resulting in the phenotypic change of at least i) above, when the mutant allele is in homozygous form in a diploid (Clhws/Clhws). In one aspect the ClHWS gene is the gene encoding a protein of SEQ ID NO. 1 or encoding a protein comprising at least 90%, 91%, 92%, 93%, 94%, 95%, 96%, 97%, 98% or 99% sequence identity to SEQ ID NO: 1, when aligned pairwise using e.g. Needle. It is noted that the expression of the phenotypic changes caused by the mutant Clhws allele may vary somewhat depending on the specific mutation in the allele and/or on the genetic background of the watermelon line. So, for example, in one background no female flowers may develop during the growing cycle, while in another background very few female flowers will develop, e.g. late in the growing cycle.

"Multibranching gene" is a single, recessive gene identified in cultivated watermelon on chromosome 8, which when mutated results in a phenotypic change of equal to or more than 45 secondary branches developing when the mutant allele is in homozygous form. In watermelons and other cucurbits, the main stem grows and forms primary lateral branches. On the primary lateral branches, the plant makes secondary lateral branches. These secondary branches are counted starting at 90 cm from the end/crown on the main stem to the end/crown. Secondary branching is, thus, in one aspect measured by counting the number of secondary branches starting at distance of 90 cm from the crown to the end/crown of the plant. This is done for several (at least 5, 6, 7, 8, 9, 10) plants of a line and the average number of secondary branches is then calculated for each line.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The term "gene" means a (genomic) DNA sequence comprising a region (transcribed region), which is transcribed into a messenger RNA molecule (mRNA) in a cell, and an operably linked regulatory region (e.g. a promoter). An example is the ClHWS gene of the invention. Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Mutant Clhws allele" or "Clhws allele" refers herein to a mutant allele of the ClHWS gene on chromosome 5 in watermelon, which causes the plant to have a phenotypic change (of at least i), described elsewhere herein) when the mutant allele is in homozygous form. The mutation in the mutant allele can be any mutation or combination of mutations, including deletions, truncations, insertions, point mutations, non-sense mutations, mis-sense mutations or non-synonymous mutations, splice-site mutations, frame shift mutations and/or mutations in one or more regulatory sequences such as promoter sequence, or enhancer or silencer sequences. In one aspect the mutant Clhws allele is a mutant allele of the ClHWS gene whereby the ClHWS gene is the gene encoding a protein of SEQ ID NO: 1 or encoding a protein comprising at least 90%, 91%, 92%, 93%, 94%, 95%, 96%, 97% or 98% or 99% sequence identity to SEQ ID NO: 1 (when aligned pairwise).

"Wild type ClHWS allele" or "ClHWS allele" refers herein to the functional allele of the ClHWS gene, which causes the plant to have a normal development of both male and female flowers in certain ratios, normal leaf shape and petals of the flowers which are not fused (see also the Figures). The wild type ClHWS allele is found in any commercial variety of watermelon (e.g. Nunhems variety Premium F1, Montreal F1, and others). In one aspect the wild type ClHWS allele is a wild type allele of the ClHWS gene whereby the ClHWS gene is the gene encoding a protein of SEQ ID NO: 1 or encoding a protein comprising at least 90%, 91%, 92%, 93%, 94%, 95%, 96%, 97%, 98% or 99% sequence identity to SEQ ID NO: 1 (when aligned pairwise).

"Mutant multibranching allele" refers herein to a mutant allele of the gene in watermelon, which causes the watermelon plant to develop equal to or more than 45 secondary branches when the mutant allele is in homozygous form (also referred to as 'multibranching growth' type). A mutant multibranching allele is found e.g. in variety Sidekick. It comprises e.g. the sequence of SEQ ID NO: 10 in the genome, which encodes the protein of SEQ ID NO: 9. Other mutant multibranching alleles can be generated by e.g. TILLING or Crispr based methods.

"Wild type multibranching allele" refers herein to the functional allele of the gene, which causes the plant to develop a normal number of secondary branches. The wild type allele is found in any commercial variety of watermelon (e.g. Nunhems variety Premium F1, Montreal F1, and others). In one aspect the wild type multibranching allele is a wild type allele of the multibranching gene, whereby the gene is the gene encoding a protein of SEQ ID NO: 11 or encoding a protein comprising at least 95%, 96%, 97%, 98% or 99% sequence identity to SEQ ID NO: 11 (when aligned pairwise, e.g. using Needle).

The term "locus" (loci plural) means a specific place or places or a site on a chromosome where for example a gene or genetic marker is found. The ClHWS locus is, thus, the location in the genome of watermelon, where the mutant allele and/or the wild type allele of the ClHWS gene is found. The ClHWS locus is a locus on cultivated watermelon chromosome 5 (using the chromosome assignment of the published watermelon genome found at world wide web at cucurbitgenomics.org under "Watermelon: Genome". "Charleston Grey") i.e. Clhws was generated in the cultivated watermelon genome by mutagenesis and the mutant Clhws allele was mapped to a defined region of chromosome 5 of cultivated watermelon.

"Induced mutant alleles" are mutant alleles in which the mutation(s) is/are/have been induced by human intervention, e.g. by mutagenesis via physical or chemical mutagenesis methods or via e.g. tissue culture (as described in e.g. Zhang et al. Plos 9(5) e96879), including also targeted gene editing techniques (such as Crispr based techniques. TALENS, etc.).

"Diploid plant" refers to a plant, vegetative plant part(s), or seed from which a diploid plant can be grown, having two sets of chromosome, designated herein as 2n.

A "DH plant" or "doubled-haploid plant" is a diploid plant produced by doubling the haploid genome of the diploid plant using e.g. in vitro techniques. A DH plant is, therefore, homozygous at all loci.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Polyploid plant" refers to plants having a higher ploidy than diploid, i.e. triploid (3n), tetraploid (4n), hexaploid (6n), octaploid (8n), etc.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of normal triploid plants (comprising three copies of the wild type ClHWS allele), by producing an appropriate amount of pollen at the appropriate day-time and for an appropriate period of time.

"Hybrid triploid plant" or "F1 triploid" or "triploid hybrid" is a triploid plant grown from hybrid, triploid seed obtained from cross fertilizing a male diploid parent with a female tetraploid parent. The male parent is used for inducing fruit set and seed production on a tetraploid female parent, resulting in fruits containing F1 hybrid triploid seeds. Both the male parent and the female parent used to produce F1 triploid seeds are inbred so that each parent line is nearly homozygous and stable.

"Seedless fruit" are fruits which contain no viable mature seeds. The fruit may contain one or more small, edible, white ovules. Optionally the fruit may contain a few brown or black seeds, but these are not viable. Viable mature seeds are seeds which can be germinated in soil under appropriate conditions and grow into plants.

"Interplanting" refers to the combination of two or more types of seeds and/or transplants sown or transplanted on the same field, especially the sowing and/or transplanting of pollenizers in the same field as triploid hybrid plants (for seedless fruit production on the triploid plants and diploid fruit production on the pollenizer plants). For example, the pollenizer may either be planted in separate rows or interplanted with the triploid plants in the same row (e.g. in hills within each row). Pollenizers may also be planted in between rows of triploids. Also seeds of pollenizers and triploid hybrids may be mixed prior to seeding, resulting in random seeding. The transplants of the triploid hybrid plants and/or pollenizer plants may also comprise a rootstock of a different plant. Suitable rootstocks are known in the art. Watermelon plants with a different rootstock are referred to as "grafted".

"Planting" or "planted" refers to seeding (direct sowing) or transplanting seedlings (plantlets) into a field by machine or hand.

"Vegetative propagation" or "clonal propagation" refers to propagation of plants from vegetative tissue, e.g. by in vitro propagation or grafting methods (using scions and rootstocks). In vitro propagation involves in vitro cell or tissue culture and regeneration of a whole plant from the in vitro culture. Grafting involves propagation of an original plant by grafting onto a rootstock. Clones (i.e. genetically identical vegetative propagations) of the original plant can thus be generated by either in vitro culture or grafting. "Cell culture" or "tissue culture" refers to the in vitro culture of cells or tissues of a plant. "Regeneration" refers to the development of a plant from cell culture or tissue culture or vegetative propagation. "Non-propagating cell" refers to a cell which cannot be regenerated into a whole plant.

"Recessive" refers to an allele which expresses its phenotype (e.g. predominantly male flowers developing) when no dominant allele is present in the diploid genome, i.e. when it is homozygous in a diploid. The mutant Clhws allele results in a plant having a phenotypic change (described elsewhere) when present in two copies in a diploid plant, optionally in four copies in a tetraploid plant or in two or three copies in a triploid plant or in the respective number of copies in another polyploidy. The dominant allele is herein also referred to as the wild type (WT) allele.

"Cultivated watermelon" or "*Citrullus lanatus*" refers herein to *Citrullus lanatus* ssp. *vulgaris*, or *Citrullus lanatus* (Thunb.) Matsum. & Nakai subsp. *vulgaris* (Schrad.), and having good agronomic characteristics, especially producing marketable fruits of good fruit quality and fruit uniformity.

"Wild watermelon" refers herein to *Citrullus lanatus* ssp. *lanatus* and *Citrullus lanatus* ssp. *mucosospermus*, producing fruits of poor quality and poor uniformity.

"SNP marker" refers to a Single Nucleotide Polymorphism between e.g. a mutant Clhws allele and a wild type ClHWS allele. For example, SEQ ID NO: 5 provides a sequence comprising a SNP at nucleotide 101, whereby the presence of a 'G' (Guanine) indicates the presence of the wild type ClHWS allele and the presence of a 'A' (Adenine) indicates the presence of the mutant allele, which encodes the protein of SEQ ID NO: 2 (W204STOP mutation). Using a SNP marker assay which can distinguish between the mutant and wild type allele of the ClHWS gene (i.e. an allele specific assay) one can screen pants, plant parts or the DNA therefrom for the presence of the mutant allele.

"Cultivated watermelon genome" and "physical position on the cultivated watermelon genome" and "chromosome 5" refers to the physical genome of cultivated watermelon, the reference genome is found on the world wide web at cucurbitgenomics.org under "Watermelon: Genome", e.g. "Watermelon (Charleston Grey)" and the physical chromosomes and the physical position on the chromosomes.

A "chromosome region comprising the mutant Clhws allele" refers to the genomic region of e.g. chromosome 5 of cultivated watermelon which region carries the mutant Clhws allele. The presence of the allele can be determined phenotypically and/or by the presence of one or more molecular markers, e.g. SNP markers or other markers, linked to the mutant Clhws allele or preferably markers distinguishing different Clhws alleles or by the genomic sequence of the allele sequence itself (e.g. sequencing the allele). A marker is "linked to the Clhws allele", if it is physically coupled to the allele. An "allele specific marker" is a marker which is specific for a particular allele (e.g. a specific mutant allele) and is thus discriminating between e.g. the mutant allele and the wild type allele.

A pair of "flanking markers" refers to two markers, preferably two SNP markers or two sequences comprising the SNP markers, which are linked to the Clhws allele, and/or which are closely linked to the Clhws allele, whereby the Clhws allele is located in-between the two markers or in-between the two sequences comprising the markers.

"Brix" or "degree Brix" or "° brix" refers to the mean total soluble solids content as measured on several mature fruits using a refractometer. Preferably the mean of at least three fruits, each measured between the centre and the rind of the cut-open fruit, is calculated.

"Marketable" in relation to fruit quality means that the watermelon fruits are suitable for being sold for fresh consumption, having good flavour (no off-flavours), a degree brix of at least 9.0, preferably at least 10.0 or at least 11.0 and preferably also a uniform fruit flesh color, being e.g. white (e.g. variety Cream of Saskatchewan), yellow (e.g. variety Yamato Cream 1), orange (e.g. variety Tendersweet), pink (e.g. variety Sadul), pinkish red (e.g. variety Crimson Sweet), red (e.g. variety Sugar Baby) or dark red (e.g. variety Dixie Lee).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

"Physical distance" between loci (e.g. between molecular markers and/or between phenotypic markers) on the same chromosome is the actually distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of about 1%. If no recombinants can be found, the RF is zero and the loci are either extremely close together physically or they are identical. The further apart two loci are, the higher the RF.

"Uniformity" or "uniform" relates to the genetic and phenotypic characteristics of a plant line or variety. Inbred lines are genetically highly uniform as they are produced by several generations of inbreeding. Likewise, and the F1 hybrids and the triploid hybrids which are produced from such inbred lines are highly uniform in their genotypic and phenotypic characteristics and performance.

A genetic element, an introgression fragment, or a gene or allele conferring a trait (such as the phenotypic characteristics of the mutant Clhws allele) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as wild type line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Cultivated watermelons containing the genetic element, locus, introgression fragment, gene or allele (e.g. a mutant Clhws allele) can be generated de novo, e.g. by mutagenesis (e.g. chemical mutagenesis, CRISPR-Cas induced, etc.) and then e.g. be crossed into other cultivated watermelons.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30, 40, 50 or more plants (or plant parts) are measured, preferably in randomized experimental designs with several replicates and suitable control plants grown under the same conditions in the same experiment. "Statistically significant" or "statistically significantly" different or "significantly" different refers to a characteristic of a plant line or variety that, when compared to a suitable control show a statistically significant difference in that characteristic (e.g. the p-value is less than 0.05, p<0.05, using ANOVA) from the (mean of the) control.

The term "traditional breeding techniques" encompasses herein crossing, backcrossing, selfing, selection, double haploid production, chromosome doubling, embryo rescue, protoplast fusion, marker assisted selection, mutation breeding etc., all as known to the breeder, by which, for example, a chromosome 5 comprising a mutant Clhws allele can be obtained, identified and/or transferred.

"Backcrossing" refers to a breeding method by which a (single) trait, such as the phenotypic changes conferred by the mutant Clhws allele, can be transferred from one (often an inferior) genetic background (also referred to as "donor") into another (often a superior) genetic background (also referred to as "recurrent parent". An offspring of a cross (e.g. an F1 plant obtained by crossing e.g. the donor with the recurrent parent watermelon, or an F2 plant or F3 plant, etc., obtained from selfing the F1), is "backcrossed" to the parent with e.g. the superior genetic background. After repeated backcrossing, the trait of the one (often inferior) genetic background will have been incorporated into the other (often superior) genetic background.

"Marker assisted selection" or "MAS" is a process of using the presence of molecular markers (such as SNP markers), which are genetically and physically linked to a particular locus or to a particular chromosome region or allele specific markers, to select plants for the presence of the specific locus or region or allele. For example, a molecular marker genetically and physically linked to the mutant Clhws allele or an allele specific marker, can be used to detect and/or select e.g. watermelon plants, or plant parts, comprising the Clhws allele. The closer the linkage of the molecular marker to the locus, the less likely it is that the marker is dissociated from the locus through meiotic recombination. Likewise, the closer two markers are linked to each other the less likely it is that the two markers will be separated from one another (and the more likely they will co-segregate as a unit). Allele specific markers are preferred markers, as they select for the allele directly.

A molecular marker (or a sequence comprising a molecular marker) within 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less of another marker (or a sequence comprising the molecular marker), or of a locus, refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less, of the genomic DNA region flanking the marker (i.e. either side of the marker).

"LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Transgene" or "chimeric gene" refers to a genetic locus comprising a DNA sequence, such as a recombinant gene, which has been introduced into the genome of a plant by transformation, such as Agrobacterium mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome. When referring to a "sequence" herein, it is understood that the molecule having such a sequence is referred to, e.g. the nucleic acid molecule.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 90%, 92%, 95%, 98%, 99% or more (as determined by Emboss "needle" using default parameters, i.e. gap creation penalty=10, gap extension penalty=0.5, using scoring matrix DNAFULL for nucleic acids and Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 91%, 92%, 93%, 94%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2× SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C. for 20 min, or equivalent conditions.

"M1 generation" or "M1 plants" in context with the present invention shall refer to the first generation that is produced directly from the mutagenic treatment. A plant grown from seeds treated with a mutagen e.g. is a representative of an M1 generation.

"M2 generation" or "M2 plant" shall refer herein to the generation obtained from self-pollination of the M1 generation. A plant grown from seeds obtained from a self-pollinated M1 plant represents a M2 plant. M3, M4, etc. refers to further generations obtained after self-pollination.

An "mRNA coding sequence" shall have the common meaning herein. An mRNA coding sequence corresponds to the respective DNA coding (cDNA) sequence of a gene/allele apart from that thymine (T) is replaced by uracil (U).

A "mutation" in a nucleic acid molecule (DNA or RNA) is a change of one or more nucleotides compared to the corresponding wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "nucleic acid molecule" shall have the common understanding in the art. It is composed of nucleotides comprising either of the sugars deoxyribose (DNA) or ribose (RNA).

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a pre-mature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid, but preferably at least 10, 20, 30, 40, 50, 60, 70, 80, 90, 100 or more amino acids, at either the N-terminus or the C-terminus of the protein is missing compared to the amino acid sequence of the corresponding wild type protein. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made.

A "mutation in a protein" is a change of one or more amino acid residues compared to the wild type sequence, e.g. by replacement, deletion, truncation or insertion of one or more amino acid residues.

"Mutant protein" is herein a protein comprising one or more mutations in the nucleic acid sequence encoding the protein, whereby the mutation results in (the mutant nucleic acid molecule encoding) a "reduced-function" or "loss-of-function" protein, as e.g. measurable in vivo, e.g. by the phenotype conferred by the mutant allele.

"Wild type 3-dimensional structure" or "wild type protein folding" refers to the in vivo folding of the wild type protein to carry out its normal function in vivo. "Modified 3-dimensional structure or modified protein folding" refers to the mutant protein having a different folding than the wild type protein, which reduces or abolishes its normal function or activity in vivo, i.e. the protein has a reduced-function or loss-of-function. Protein truncations also lead to a modified 3-dimensional structure. The 3-D structure can be predicted to be modified using e.g. programs such as RaptorX and comparing the predicted wild type protein structure to the predicted modified protein structure.

In context of the present invention, "decreased activity" of a protein shall mean a decrease in activity of a Clhws protein when compared to a corresponding wild type plant cell or a corresponding wild type plant. Decrease shall in one aspect comprise an entire knock-out or knock-down of gene expression, or the production of a loss-of-function or of a reduced-function Clhws protein, e.g. a mutant Clhws protein may have lost function or decreased function compared to the wild type, functional ClHWS protein. A decrease in activity can be a decrease in the expression of a gene encoding a ClHWS protein (also referred to as knock-down), or a knock-out of the expression of a gene encoding a ClHWS protein and/or a decrease in the quantity of a ClHWS protein in the cells, or a reduced-function or loss-of-function in the activity of a Clhws protein in the cells.

In context with the present invention, the term "wild type plant cell" or "wild type plant" means that they comprise wild type ClHWS alleles and not mutant Clhws alleles. Thus, the wild type plant or wild type plant cell is a plant or plant cell comprising fully functional ClHWS genes, encoding a fully functional ClHWS proteins (also referred to as wild type ClHWS protein), e.g. regarding watermelon plants or plant cells a diploid watermelon plant producing the protein of SEQ ID NO: 1 (or a variant wild type protein comprising at least 90% sequence identity to SEQ ID NO: 1) and producing normal flowers, normal ratios of male to female flowers, normal petals and leaves.

"Knock-out" or "entire knock-out" shall be understood that expression of the respective gene is not detectable anymore.

"Loss-of-function" or "reduced-function" or "decreased function" shall mean in context of the present invention that the protein, although possibly present in amounts equal or similar to a corresponding wild type protein, does not evoke its normal effect anymore, i.e. for mutant alleles encoding such a protein when present in homozygous form in a diploid plant, the plant produces a phenotypic change described elsewhere herein.

"Conserved domain" refer to conserved protein domains, such as the "F-box domain". In the watermelon ClHWS protein of SEQ ID NO: 1 a 'F-box domain' is found from amino acid 45 to 83, or the equivalent amino acids in a protein comprising at least 90%, 91%, 92%, 93%, 94%, 95%, 96%, 97%, 98%, 99% or more sequence identity to SEQ ID NO: 1. Conserved domains can e.g. be found in the Conserved Domain Database of the NCBI (world wide web at ncbi.nlm.nih.gov/cdd).

"Targeted gene editing" is referred to techniques whereby endogenous target genes can be modified, e.g. one or more nucleotides can be inserted, replaced and/or deleted e.g. in the promoter or coding sequence. For example CRISPR based techniques, such as Crispr-Cas9 gene editing. Crispr-Cpf1 gene editing, or more recent techniques called 'base editing' or 'primer editing' can be used to modify endogenous target genes, such as the endogenous wild type ClHWS gene in watermelon.

"Genotyping" methods are methods whereby the genotype or allelic composition of a plant or plant part or seed can be determined. Bi-allelic genotyping assays, such as KASP-assays, can distinguish between two alleles at a locus.

"Oligonucleotides" or "oligos" or "oligonucleotide primers or probes" are short, single-stranded polymers of nucleic acid, e.g. at least 10, 11, 12, 13, 14, 15, 16, 17, 18, 19, 20, 21, 22, 23, 24 or more nucleotides in length. Oligos may be unmodified or modified with a variety of chemistries depending on their intended use, for example, the addition of 5' or 3' phosphate groups to enable ligation or block extension, respectively, labeling with radionuclides or fluorophores and/or quenchers for use as probes, the incorporation of thiol, amino, or other reactive moieties to enable the covalent coupling of functional molecules such as enzymes, and extension with other linkers and spacers of diverse functionality. DNA oligos are the most commonly used, but RNA oligos are also available. The length of an oligo is usually designated by adding the suffix -mer. For example, an oligonucleotide with 19 nucleotides (bases) is called a 19-mer. For most uses, oligonucleotides are designed to base-pair with a strand of DNA or RNA. The most common use for oligonucleotides is as primers for PCR (polymerase chain reaction). Primers are designed with at least part of their sequence complementary to the sequence targeted for amplification. Optimal primer length for a complementary sequence is e.g. 18 to 22 nucleotides. Optimal primer sequences for PCR are usually determined by primer design software.

"DNA microarrays" are arrays which have many microscopic spots of DNA, usually oligonucleotides, bound on a solid support. Assay targets can be DNA, cDNA, or cRNA. Depending on the system, the hybridization of targets to specific spots is detected by fluorescence, chemiluminescence, or colloidal silver or gold. Microarrays are used for multiple applications such as simultaneous measurement of the expression of large numbers of genes, enabling genome-wide gene expression analysis, as well as genotyping studies using e g single-nucleotide polymorphism (SNP) or InDel analysis.

"Complementary strands" refer to two strands of complementary sequence, and may be referred to as sense (or plus) and anti-sense (or minus) strands for double stranded DNA. The sense/plus strand is, generally, the transcribed sequence of DNA (or the mRNA that was generated in transcription), while the anti-sense/minus strand is the strand that is complementary to the sense sequence. For any of the sequences provided herein only one strand of the sequence is given, but the complementary strand of the given strand is also encompassed herein. The complementary nucleotides of DNA are A complementary to T, and G complementary to C. The complementary nucleotides of RNA are A complementary to U, and G complementary to C.

FIGURES

FIG. 1: A pairwise amino acid sequence alignment between the wild type (WT) ClHWS protein of SEQ ID NO: 1 and the W204* mutant Clhws protein of SEQ ID No: 2. The F-box domain is highlighted in bold.

FIG. 2: A pairwise amino acid sequence alignment between the *Arabidopsis* HWS protein At3g61590 with the ClHWS protein of SEQ ID NO: 1. The *Arabidopsis* sequence has 6 repetitive regions following the F-box domain, which is from amino acid 41 to 85: Kelch 1 region is from amino acid 81 to 135, Kelch 2 region is from amino acid 137 to 178, Kelch 3 region is from amino acid 196 to 246, Kelch 4 region is from amino acid 251 to 299, Kelch 5 region is from amino acid 302 to 350, Kelch 6 region is from amino acid 352 to 401.

FIG. 3: Photograph of the leaves of the plant comprising the W204* mutant allele in homozygous form (left photograph) and of the leaves of the plant comprising the wild type ClHWS allele in homozygous form (right photograph).

FIG. 4: Photograph of a male flower of the plant comprising the W204* mutant allele in homozygous form (left photograph), whereby the petals are fused and sepals are partially absent. On the right side a normal male flower (without fused petals) of the plant comprising the wild type ClHWS allele in homozygous form (right photograph).

FIG. 5: 3-dimensional (3D) structure prediction (world wide web at raptorx.uchicago.edu/) for the wild type ClHWS protein, with the N-terminal region (amino acid 1 to 44), F-box domain (amino acid 45 to 83) and the C-terminal region from amino acid 93 to 380, which comprises a number of beta sheets. The protein is, thus, highly structured. In the W204* mutant most of the beta sheets at the C-terminal end are missing.

FIG. 6: Pairwise alignment of the protein of SEQ ID NO: 1 (encoded by SEQ ID NO: 4) and the protein of SEQ ID NO: 7 (encoded by SEQ ID NO: 8). The F-box is indicated by solid line boxes, the C-terminal beta sheet region is indicated by dashed line boxes. The mutants of Table A are indicated in bold and underline.

FIG. 7: Photograph of a leaf of the mutant F3 plant comprising the W204* mutant allele in homozygous form (left foto) and a leaf of the wild type plant having a wild type ClHWS allele (right foto). The plant comprising the mutant allele has a 'modified leaf shape' or 'more broadly lobed leaves' compared to the wild type.

FIG. 8: Photograph of male flowers of the mutant F3 plant comprising the W204* mutant allele in homozygous form (two fotos on the left side) and of a male flower of the wild type plant having a wild type ClHWS allele (two fotos on the right side). The plant comprising the mutant allele has male flowers with different appearance compared to the wild type.

DETAILED DESCRIPTION

A first embodiment of the present invention concerns cultivated watermelon plants. *Citrullus lanatus*, comprising at least one copy of a mutant allele of a gene, named herein ClHWS gene, conferring (when in homozygous form) a change in the ratio of male to female flowers developing, especially a higher percentage of male flowers developing (or lower percentage of female flowers developing) when compared to the plant homozygous for the functional, wild type allele of the gene. Thus, the wild type ratio of male to female flowers, or the percentage of male flowers out of all flowers, is modified in the plant comprising the mutant allele in homozygous form, with significantly fewer female flowers or even no female flowers being produced.

The watermelon plant which is homozygous for the mutant allele of the ClHWS gene, will therefore in one aspect produce a modified (higher) percentage of male flowers or a modified (higher) ratio of male to female flowers compared to the wild type plant, e.g. 100% male flowers to 0% female flowers, or 99.5%:0.5%, 99%:1%, 98%:2%, 97%:3% male flowers to female flowers, optionally 96%:4%, or 95% to 5%, or 94% to 6% (about 15.6:1), or 93% to 7% (ratio about 13:1), or 92% to 8% (ratio about 11:1), or 91% to 9% (ratio about 10:1), or 90%:10% (ratio about 9:1) male flowers to female flowers. Thus, the male flower to female flower ratio is at least 9:1, preferably at least 10:1, or higher.

In one aspect the watermelon plant which is homozygous for the mutant allele of the ClHWS gene produces a significantly higher percentage of male flowers compared to the plant homozygous for the wild type allele. e.g. at least 90%, 91%, 92%, 93%, 94%, 95%, 96%, 97%, 98%, 99%, 99.5% or 100% of the flowers that develop are male flowers.

This higher percentage of male flowers (or higher ratio of male to female flowers) in a mutant line can be analysed by growing a plant line which is homozygous for the mutant allele under the same conditions and for the same period as a wild type line (homozygous for the wild type allele) and counting the male and female flowers which develop during that period. The period may be a certain number of weeks (e.g. 1, 2, 3, 4, 5, 6, 7 or more weeks) or the entire growing period. The average percentage of male flowers of the mutant line and the wild type line can then be compared. Likewise the ratio of male to female flowers can be compared between the genotype homozygous for the mutant allele and the genotype homozygous for the wild type allele. Preferably the genetic backgrounds of the two lines are similar, e.g. the mutant allele can be backcrossed into a certain line and the recurrent parent line is the control line (comprising the wild type allele in homozygous form).

In one aspect the plant homozygous for the mutant allele produces 100% or 99.5% or 99% (or at least 90%, 91%, 92%, 93%, 94%, 95%, 96%, 97%, 98%) male flowers out of the total number of flowers produced during at least 1, 2, 3, 4, 5, 6, 7 or 8 weeks of growing in the field, e.g. during week 4, 5 and/or 6 after transplant into the field or during the entire growing period in the field.

Watermelon seeds may e.g. be sown in the greenhouse and after about 4 to 5 weeks the seedlings may be transplanted into the field. The first flowers may develop already in week 1 or 2 after transplant, with all plants flowering in weeks 4, 5, 6 after transplant. Therefore, in one aspect the male and female flowers developing on a plant line homozygous for the mutant allele and a plant line homozygous for the wild type allele can be counted easily in weeks 4, 5 and/or 6 after transplant into the field. But other periods may also be used, e.g. weeks 3, 4, 5, 6 and 7 after transplant into the field, or week 8, 9 and 10 after transplant, or other specified periods (see Examples). The control (wild type) line and the line comprising the mutant allele in homozygous form should both be compared during the same developmental age of the plants and during the same growing conditions for the same period of time. Also, sufficient number of plants per line should be included. e.g. preferably at least 2, 3, 4, 5, 6 or more. Comparisons can be carried out in the greenhouse or in a tunnel or in the field. See also the Examples for a field trial set-up to compare flower development.

If few female flowers do develop on the plant homozygous for the mutant allele, these are generally not fertilized and do not develop into fruits. Also, if female flowers do develop, these develop generally later in the developmental age of the plant, so that during the earlier developmental stages (e.g. during at least 1, 2, 3, 4, 5 or 6 weeks after transplant into the field) only or mainly male flowers are produced.

Other phenotypes, conferred when the mutant allele is in homozygous form, can be that the petals of the male flowers are fused or the male flower appearance is different and/or that the leaf shape is different than in the wild type Thus, in one aspect cultivated watermelon plants are provided, comprising at least one copy of a mutant allele of a single recessive gene called ClHWS whereby the plants show a phenotypic change (compared to the plant homozygous for the functional wild type allele) of at least i) only male flowers developing or a larger percentage of male flowers developing or a larger ratio of male to female flowers developing than in the homozygous wild type, and further optionally ii) male flowers frequently but not always having fused petals or male flowers having a different appearance and/or iii) the plant having differently shaped leaves (e.g. more broadly lobed).

The ClHWS gene is an endogenous gene of cultivated watermelon, which when mutated and in homozygous form results in a significantly higher percentage of male flowers (or exclusively male flowers) being produced, optionally with other characteristics being changed, such as leaf shape and/or male flower appearance or male flowers comprising fused petals.

A segregating population made by crossing the mutant watermelon plant identified by the inventors with an elite watermelon line enabled mapping of the gene to a region of 0.27 Mb towards one end of chromosome 5. Further analysis in the region led to the identification of a gene comprising a mutation which led to a premature STOP codon of the codon encoding amino acid 204 (W204) and a truncation of the encoded protein.

The single nucleotide change (Guanine to Adenine) resulted in the codon TGG (encoding amino acid W or Trp or Tryptophan of amino acid 204) being mutated to TAG (translation STOP codon). The mutation was unique to the line and was not found in 107 whole genome re-sequenced lines. The gene was named ClHWS. To screen plants for the mutant allele an allele specific marker was designed, provided in SEQ ID NO: 5. The SNP at nucleotide 101 of SEQ ID NO: 5 (either being a G to detect the codon TGG or an A to detect the codon TAG, can thus be used to distinguish between the wild type allele and the mutant allele (W204*), encoding the truncated protein. For other mutants (e.g. those of Table A) similar allele specific markers can be easily designed. The TGG codon, which was mutated into TAG, is found in the genomic sequence of SEQ ID NO: 4 at nucleotides 610 to 612 and in the genomic sequence of SEQ ID NO: 8 at nucleotides 1797 to 1799. In the genome of watermelon a change of nucleotide 611 of SEQ ID NO: 4 or at nucleotide 1798 of SEQ ID NO: 8 is, therefore, detectable with the SNP marker and encodes a mutant ClHWS protein. In homozygous form this mutation leads to the phenotype described.

In the mutant watermelon plant the codon for Tryptophan (W or Trp) at amino acid position 204 of the wild type ClHWS protein (SEQ ID NO: 1) was replaced by a STOP codon in the mutant protein, which thereby prematurely ended at amino acid 203 (SEQ ID NO: 2), as shown in FIG. 1. In the cDNA of the mutant allele nucleotide 611 is an Adenine (A), while it is a Guanine (G) in the wild type cDNA (SEQ ID NO:3). This single nucleotide change (or SNP, from G→A) results in the codon changing from codon TGG (encoding Trp or W) into TAG (a stop codon). Further, cDNA and genomic DNA were found to be identical, as no introns were present.

It was found that this truncation of the ClHWS protein lead to the protein being non-functional or having reduced function in vivo. As a result the plant homozygous for this mutant protein (and thus lacking the functional wild type protein) develops a combination of phenotypes which differ from the wild type, especially a significantly increased percentage of male flowers (and a higher ratio of male to female flowers), occasionally fused petals seen in male flowers and a different leaf shape. When looking at the Protein Structure Property Prediction of the wild type ClHWS protein in RaptorX (world wide web at raptorx.uchicago.edu/Structure Property Pred/predict/), one can see that the amino acids W204 is in a highly conserved and highly structured and folded region consisting of many beta-sheets (FIG. 5). As can be seen the entire protein is folded into three distinct structures, with amino acid 93 to 380 comprising a number of beta sheets, which fold into the 3-D structure shown. The truncated protein which contains amino acid 1 to 203 only is highly likely to abolish the protein functionality in vivo. It is, therefore, very likely that the same phenotypic change will be seen at least in any other mutant, in which either the wild type protein is not expressed or in which the encoded protein is non-functional. In Table A or B, for example, the W229Stop mutant also results in a truncated protein and Example 3 shows that seedlings of this mutant show the same abnormal (broader lobed) leaf shape as seen in the W204Stop mutant. It is, therefore, expected that also a higher percentage of male flowers will be developing in plants homozygous for the W229Stop mutant allele.

However, also reduced expression of the wild type allele or reduced function proteins may lead to a higher percentage of male flowers developing. The person skilled in the art can easily test this without undue burden by generating mutant Clhws alleles (e.g. by mutagenesis and TILLING or by targeted gene editing), making them homozygous in the plant and analyzing the phenotype. The skilled person can, for example, focus on mutants which are predicted by e.g. Provean analysis to be 'deleterious' and analyze their phenotype in vivo, in homozygous plants. See Example 3. Although Provean analysis is only a tool to predict protein function, it is useful in saving resources by starting with the analysis of mutant alleles that have a higher chance of having an effect on reducing or abolishing protein function in vivo.

In one aspect a watermelon plant or plant part is provided comprising at least one copy of a mutant allele of a gene named ClHWS, wherein said mutant allele either a) comprises one or more mutations in a regulatory element, resulting in no expression or reduced expression of the allele compared to the wild type allele, and/or b) encodes a mutant protein comprising one or more amino acids replaced, inserted or deleted compared to the wild type protein, wherein said mutant allele of a) or b) confers a significantly increased percentage of male flowers (or a phenotype of i) only male flowers developing or a larger percentage of male flowers or a larger ratio of male to female flowers developing than in the homozygous wild type, and further optionally ii) male flowers frequently but not always having fused petals or male flowers having a different appearance and/or iii) the plant having differently shaped leaves), when the mutant allele is in homozygous form, and wherein the wild type watermelon allele encodes a protein of SEQ ID NO: 1 or a protein comprising at least 90%, 91%, 92%, 93%, 94%, 95%, 96%, 97%, 98%, 99% or more sequence identity to SEQ ID NO: 1.

The wild type functional ClHWS protein of watermelon is provided in SEQ ID NO: 1. There may however be some amino acid sequence variation within watermelons and functional ClHWS proteins may comprise e.g. at least 1, 2, 3, 4, 5, 6, 7, 8, 9, 10, 11, 12, 13, 14, 15 or more amino acids which are different than in SEQ ID NO: 1 provided herein or whereby the protein comprises comprising at least 90%, 91%, 92%, 93%, 94%, 95%, 96%, 97%, 98%, 99% or 99.3%, 99.4%, 99.5% or 99.6%, 99.7%, 99.8% or 99.9% sequence identity to the proteins of SEQ ID NO: 1 (when aligned pairwise using e.g. Emboss-Needle). Such functional variants of the ClHWS protein of SEQ ID NO: 1 may exist in other lines or varieties of watermelon. These alleles may, thus, vary in sequence, but the phenotype of the plant is equal to the wild type phenotype. Such functional variant alleles (allelic variants) can be found by e.g. sequencing the ClHWS gene of many different watermelon lines or varieties which have a normal flowering pattern and normal leaf shape and petals.

Therefore, in one aspect functional variants of the watermelon protein of SEQ ID NO: 1 are proteins comprising at least 90%, 91%, 92%, 93%, 94%, 95%, 96%, 97%, 98%, 99% or 99.3%, 99.4%, 99.5% or 99.6%, 99.7%, 99.8% or 99.9% sequence identity to the protein of SEQ ID NO: 1, when aligned pairwise (using e.g. Needle with default parameters). In one aspect the amino acid sequence variation is found outside the conserved F-box domain. In one aspect the functional proteins, which comprise at least 90%, 91%, 92%, 93%, 94%, 95%, 96%, 97%, 98%, 99% or 99.3%, 99.4%, 99.5% or 99.6%, 99.7%, 99.8% or 99.9% sequence identity to the protein of SEQ ID NO: 1, therefore comprise 100% identical amino acids to SEQ ID NO: 1 for the F-box domain shown in FIG. 1 in bold.

As the F-box domain is highly conserved within the species, any mutation (deletion, insertion and/or replacement of at least 1, 2, 3, 4, 5 or more amino acids) in the domain is predicted to lead to the mutant ClHWS protein having a reduced function or no function in vivo, thereby leading to the modified phenotype described herein when the mutant allele is in homozygous form in e.g. a diploid plant.

Thus, inserting, deleting and/or replacing one or more amino acids in the F-box domain will negatively affect the protein function.

Similarly, due to the 3-D structure folding of the C-terminal region starting at amino acid 93 and ending at amino acid 380 of SEQ ID NO: 1 (or the equivalent region in a protein comprising at least 90%, 93% 95%, 96%, 97%, 98% or 99% sequence identity to SEQ ID NO: 1) comprising a large number of beta sheets, inserting, deleting and/or replacing one or more amino acids in the C-terminal region will negatively affect the protein function. This is, therefore, also an aspect herein. Therefore, any insertion, deletion or replacement of one or more amino acids of amino acid 93 to 380 (or the equivalent region in a protein comprising at least 90%, 93% 95%, 96%, 97%, 98% or 99% sequence identity to SEQ ID NO: 1), including truncations or deletions of all or part of the region, is encompassed herein as being a mutant Clhws allele which confers the modified phenotype described herein.

Therefore, in one aspect a watermelon plant or plant part is provided comprising at least one copy of a mutant allele of a gene named ClHWS, wherein said mutant allele encodes a mutant protein comprising one or more amino acids inserted, deleted or replaced in the F-box domain of the protein starting at amino acid 45 and ending at amino acid 83 of SEQ ID NO: 1 or the equivalent amino acids in a variant ClHWS protein comprising at least 90%, 93% 95%, 96%, 97%, 98% or 99% sequence identity to SEQ ID NO: 1, or comprising one or more amino acids inserted, deleted or replaced in the C-terminal region starting at amino acid 93 and ending at amino acid 380 of SEQ ID NO: 1, or the equivalent amino acids in a variant ClHWS protein comprising at least 90%, 93% 95%, 96%, 97%, 98% or 99% sequence identity to SEQ ID NO: 1, and wherein said mutant allele confers i) only male flowers developing or a larger percentage of male flowers or a larger ratio of male to female flowers developing than in the homozygous wild type, and further optionally ii) male flowers frequently but not always having fused petals or male flowers having a different appearance and/or iii) the plant having differently shaped leaves), when the mutant allele is in homozygous form.

The term 'starting at' and 'ending at' or 'from' and 'to' includes the first and last amino acid mentioned.

Thus, insertion, deletion and/or replacement of one or more amino acids in the F-box domain (starting at amino acid 45 and ending at amino acid 83) and/or in the C-terminal region starting at amino acid 93 and ending at amino acid 380, may be the insertion, deletion and/or replacement of at least 1, 2, 3, 4, 5, 6, 7, 8, 9, 10 or more amino acids. Included are also truncations relative to the wild type protein, whereby at least 10, 20, 30, 40, 50, 60, 70, 80, 90, 100, 150, 160, 170, 177, 200, 202, 210, 220, 250, 300, 350 or more amino acids of the C-terminal part of the protein are missing (or are replaced by different amino acids than the wild type).

In yet another aspect a watermelon plant or plant part is provided comprising at least one copy of a mutant allele of a gene named ClHWS, wherein said mutant allele encodes a mutant protein comprising at least 10, 20, 30, 40, 50, 60, 70, 80, 90, 100, 110, 120, 130, 140, 150, 160, 170, 177, 180, 190, 200, 202 or more amino acids inserted, deleted and/or replaced in SEQ ID NO: 1 or in a variant ClHWS protein or a protein comprising at least 90%, 93% 95%, 96%, 97%, 98% or 99% sequence identity to SEQ ID NO: 1, and wherein said mutant allele confers the modified phenotype described when the mutant allele is in homozygous form. The mutant ClHWS protein may thus e.g. be truncated at the N-terminal or C-terminal, lacking said at least 10, 20, 30, 40, 50, 60 70, 80, 90, 100, 150, 160, 170, 177, 180, 190, 200, 202, 210, 220, 230, 250, 300, 350 or more amino acids at the N-terminal or C-terminal, or any other at least 10 amino acids may be deleted, replaced or inserted compared to the wild type functional ClHWS protein.

Mutant alleles can be generated by various techniques, such as random mutagenesis or targeted gene editing, and the phenotype of the mutant allele can then be analysed in plants homozygous for the mutant allele. Using random or targeted mutagenesis techniques any mutation can be generated or reconstructed. e.g. the mutants described in Table A can be easily made de novo. TILLING primers can, for example, be designed to the specific mutations in the allele, enabling de novo identification of e.g. M2 plants comprising the mutants of Table A. No seed deposit is requirement for enablement when the gene sequence is disclosed. Similarly, targeted gene editing can be used to generate any desired mutation in the allele.

Any mutant allele which results in an insertion, deletion and/or replacement of one or more amino acids of the wild type, functional protein may result in a mutant protein having reduced function or no function and may thus result in the phenotype of i) only male flowers developing or a larger percentage of male flowers developing or a larger ratio of male to female flowers developing than in the homozygous wild type plant, and further optionally ii) male flowers frequently but not always having fused petals or male flowers having a different appearance and/or iii) the plant having differently shaped leaves, when the mutant allele is in homozygous form. Plants and plant parts comprising such mutant alleles are one embodiment herein.

The 'equivalent amino acid' can easily be determined by pairwise amino acid sequence alignment, using e.g. Emboss Needle (default parameters).

A mutation in the codon may be a (at least one) nucleotide insertion, deletion or replacement in the codon, leading to e.g. a different reading frame or a different codon, e.g. encoding a different amino acid or a STOP codon. Also the entire codon may be deleted or replaced by a different codon (or optionally a stop codon), resulting in either a deletion of the encoded amino acid, or the replacement thereof.

In one aspect the mutant allele encodes an amino acid substitution (replacement) or deletion or a stop codon of amino acid number W204 of SEQ ID NO: 1 or the equivalent amino acid in a protein comprising at least 90%, 91%, 92%, 93%, 94%, 95%, 96%, 97%, 98% or 99% sequence identity to SEQ ID NO: 1, e.g. W245 of SEQ ID NO: 8.

In one aspect the mutant allele encodes an amino acid substitution (replacement) or deletion or a stop codon of amino acid number W229 of SEQ ID NO: 1 or the equivalent amino acid in a protein comprising at least 90%, 91%, 92%, 93%, 94%, 95%, 96%, 97%, 98% or 99% sequence identity to SEQ ID NO: 1, e.g. W270 of SEQ ID NO: 8.

In one aspect the mutant allele encodes an amino acid substitution (replacement) or deletion or a stop codon of amino acid number R64 of SEQ ID NO: 1 or the equivalent amino acid in a protein comprising at least 90%, 91%, 92%, 93%, 94%, 95%, 96%, 97%, 98% or 99% sequence identity to SEQ ID NO: 1, e.g. R105 of SEQ ID NO: 8.

In one aspect the mutant allele encodes an amino acid substitution (replacement) or deletion or a stop codon of amino acid number S67 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. S108 of SEQ ID NO: 8.

In one aspect the mutant allele encodes an amino acid substitution (replacement) or deletion or a stop codon of amino acid number C69 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. C110 of SEQ ID NO: 8.

In one aspect the mutant allele encodes an amino acid substitution (replacement) or deletion or a stop codon of amino acid number V219 of SEQ ID NO: 1 or the equivalent amino acid in a protein comprising at least 90%, 91%, 92%, 93%, 94%95%, 96%, 97%, 98% or 99% sequence identity to SEQ ID NO: 1, e.g. V260 of SEQ ID NO: 8.

In one aspect the mutant allele encodes an amino acid substitution (replacement) or deletion or a stop codon of amino acid number G228 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. G269 of SEQ ID NO: 8.

In one aspect the mutant allele encodes an amino acid substitution (replacement) or deletion or a stop codon of amino acid number L242 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. L283 of SEQ ID NO: 8.

In one aspect the mutant allele encodes an amino acid substitution (replacement) or deletion or a stop codon of amino acid number E324 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. E365 of SEQ ID NO: 8.

In one aspect the mutant allele encodes an amino acid substitution (replacement) or deletion or a stop codon of amino acid number G340 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. G381 of SEQ ID NO: 8.

In one aspect the mutant allele encodes an amino acid substitution (replacement) or deletion or a stop codon of amino acid number S348 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. S389 of SEQ ID NO: 8.

In one aspect the mutant allele encodes an amino acid substitution (replacement) or deletion or a stop codon of amino acid number A362 of SEQ ID NO: 1 or the equivalent amino acid in a protein comprising at least 90%, 91%, 92%, 93%, 94% 95%, 96%, 97%, 98% or 99% sequence identity to SEQ ID NO: 1, e.g. A403 of SEQ ID NO: 8.

In one aspect the mutant allele encodes the amino acid change of Table A or B in SEQ ID NO: 1 or in an allele encoding a ClHWS protein comprising at least 90%, 91%, 92%, 93%, 94%,95%, 96%, 97%, 98% or 99% sequence identity to SEQ ID NO: 1.

In one aspect the mutant allele encodes a mutant ClHWS protein which comprises a truncation of at least 10, 20, 30, 40, 50, 60, 70, 80, 90, 100, 110, 120, 130, 140, 150, 160, 170, 177, 180, 190, 200, 202, 210, 213, 215, 220, 230, 240, 250, 300, 310, 320, 330 amino acids of the C-terminal end of the protein of SEQ ID NO: 1 or of the C-terminal end of a protein comprising at least 90%, 91%, 92%, 93%, 94%, 95%, 96%, 97%, 98% or 99% sequence identity to SEQ ID NO: 1. In one aspect all amino acids starting at (and including) amino acid W204 of SEQ ID NO: 1, or the equivalent amino acid in a protein comprising at least 90%, 91%, 92%, 93%, 94% 95%, 96%, 97%, 98% or 99% sequence identity to SEQ ID NO: 1, are deleted or replaced by one or more different amino acids. In another aspect all amino acids starting at (and including) amino acid W229 of SEQ ID NO: 1, or the equivalent amino acid in a protein comprising at least 90%, 91%, 92%, 93%, 94% 95%, 96%, 97%, 98% or 99% sequence identity to SEQ ID NO: 1, are deleted or replaced by one or more different amino acids.

As mentioned the watermelon plant or plant part may comprise a mutant Clhws allele, wherein the mutant allele is produced by random mutagenesis or targeted mutagenesis, such as CRISPR based methods. Random mutagenesis may for example be chemical induced (e.g. EMS treatment) or radiation induced mutagenesis or other methods, whereby mutations are randomly induced in the genome and then plants or plant parts comprising mutations in the endogenous ClHWS gene can be screened for and identified. Targeted mutagenesis are methods whereby mutations are specifically introduced into a target gene, such as the ClHWS gene, using e.g. Crispr-Cas9, or Crispr-Cpfl or other known methods.

In one aspect the plant comprising the mutant allele is not produced exclusively by an essentially biological process, meaning that the mutant allele has at one point been generated by human intervention. If such a human generated mutant allele is transferred from one plant to another by crossing and selection, then the patent covers plants comprising the mutant allele, even if the plant itself has been generated solely by crossing and selection.

In one aspect the watermelon plant is diploid and comprises at least one copy of a mutant Clhws allele as described above, i.e. the plant is heterozygous. As the phenotype is only seen when the mutant allele is in homozygous form, these plants have normal flowering and normal leaves. Selfing of such heterozygous plants will generate a plant which is homozygous and which comprises two copies of the mutant allele. In one aspect the watermelon plant is diploid and comprises two copies of a mutant Clhws allele as described above, i.e. the plant is homozygous. The plant therefore also has a modified phenotype as described herein.

The plants and plant parts comprising at least one copy of a mutant Clhws allele is preferably a cultivated plant, not a wild plant. So preferably cultivated watermelon (*Citrullus lanatus*). The plant may be an inbred line, a F1 hybrid or a breeding line.

In one aspect the plant is a watermelon plant and the watermelon plant is diploid, triploid or tetraploid, comprising at least one copy of a mutant Clhws allele. The diploid plant or plant part comprises in one aspect two copies, the triploid plant or plant part comprises one, two or three copies and the tetraploid plant or plant part comprises two or four copies of the mutant Clhws allele.

Also seeds from which a plant or plant part as described above can be grown are encompassed herein.

The plant and seed from which the plant can be grown is particularly suitable as pollenizer, to produce pollen for the pollination of other watermelon plants. The pollenizer will produce only or mainly male flowers, which produce pollen. As no or very few female flowers are produced, the plants will not produce fruits (or very few fruits). It is preferably interplanted with watermelon plants of which the fruits are to be harvested, e.g. diploid or triploid watermelon plants, of which the female flowers are pollinated with pollen of the pollenizer plant.

To maintain a diploid pollenizer plant, a plant which is homozygous for the mutant Clhws allele is used, in one aspect, as male parent to pollinate a female parent which is heterozygous for the mutant Clhws allele. The seeds produced by the female parent will be heterozygous for the mutant allele or homozygous for the mutant allele, with a ratio of 50%:50%. This method is encompassed herein.

A method of crossing a diploid male parent comprising two copies of a mutant Clhws allele with a female parent comprising one copy of a mutant Clhws allele, allowing fruits to develop and collecting the seeds from said fruits. The method further comprises selecting those seeds or seedlings which are homozygous for the mutant Clhws allele.

The selection can be done by either a) germinating the seeds to grow seedlings and selecting the seedlings which comprises two copies of the mutant Clhws allele by selecting seedlings comprising a modified leaf shape and/or b) selecting seeds or seedlings based on DNA analysis or image analysis or seed weight and/or shape comprising two copies of the mutant Clhws allele.

The DNA analysis is preferably a non-destructive (seeds remain viable) analysis of the DNA, such as seed-chipping to have tissue comprising genomic DNA and then analysing the presence of the mutant allele in the DNA (e.g. using PCR based assays).

Image analysis may for example be computer vision-based analysis such as described by SeedX (world wide web at seed-x.com) and in patent applications WO2019106638, WO2019106639 and WO2019106641.

Seed weight and/or shape may also be different between the seeds which are homozygous for the mutant allele and seeds which are heterozygous for the mutant allele.

The plant part comprising at least one copy of the mutant Clhws allele may be a cell, a flower, a leaf, a stem, a cutting, an ovule, pollen, a root, a rootstock, a scion, a fruit, a protoplast, an embryo, an anther.

Further a vegetatively propagated plant propagated from a plant part and comprising at least one copy of a mutant Clhws allele in its genome is provided.

In one aspect also a method of producing seedless watermelon fruits is provided, said method comprising growing a diploid watermelon plant comprising two copies of a mutant Clhws allele in the vicinity of a triploid watermelon plant, allowing pollination of the flowers of the triploid plant with pollen of the diploid plant and optionally harvesting the seedless fruits that develop on the triploid plant.

When referring to 'growing in the vicinity' this means that the diploid pollenizer plants are near enough to the triploid plants to allow insects, who can visit the pollenizer plants, to transfer the pollen from the male flowers of the pollenizer plant to the triploid plants. The pollenizer may be interplanted in rows or in between rows or randomly in the same field as the triploid plants. Also, the pollenizer may be grafted to the same rootstock as a triploid plant, to generate a double grafted plant. Such double grafted plants can then be grown in the vicinity of triploid plants, in order to provide pollen to those plants.

A method for screening plants, plant parts or DNA therefrom for the presence of a mutant allele of a of a gene named ClHWS, or for selecting a plant or plant part comprising a mutant allele of a gene named ClHWS, or for generating a plant or plant part comprising a mutant allele of a gene named ClHWS, is provided, wherein said mutant allele either a) comprises one or more mutations in a regulatory element, resulting in no expression or reduced expression of the allele compared to the wild type allele, and/or b) encodes a mutant protein comprising one or more amino acids replaced, inserted and/or deleted compared to the wild type protein, wherein the wild type watermelon allele encodes a protein of SEQ ID NO: 1 or a protein comprising at least 90%, 91%, 92%, 93%, 94%, 95%, 96%, 97%, 98% or 99% sequence identity to SEQ ID NO: 1.

In one aspect the mutant Clhws allele comprises a mutation in the genomic DNA, resulting in the expression of a mutant ClHWS protein comprising one or more amino acids inserted, deleted or replaced as described above, e.g. W204 of SEQ ID NO: 1 or W229 of SEQ ID NO: 1 (or the equivalent amino acid in a sequence comprising at least 90%, 91%, 92%, 93%, 94%, 95%, 96%, 97%, 98% or 99% identity to SEQ ID NO: 1).

However, also different mutant alleles of the ClHWS gene, causing at least a higher percentage of male flowers to develop when in homozygous form, are embodiments of the invention. Such different mutant Clhws alleles can be generated by the skilled person without undue burden. The skilled person can, for example, generate other mutants in the ClHWS gene and determine whether they equally result in at least a higher percentage of male flowers when in homozygous form in a diploid watermelon plant.

Having identified the nucleotide sequence of the gene, the skilled person can generate watermelon plants comprising mutants in the ClHWS gene by various methods, e.g. mutagenesis, TILLING or CRISPR-Cas or other methods known in the art. Especially with targeted gene modification technologies such as Crispr-Cas, TALENS and others, targeted mutations can be made by the person skilled in the art. The skilled person can then confirm the phenotype of a plant homozygous for the mutant Clhws allele, i.e. at developing least a higher percentage of male flowers. Therefore, the skilled person is not limited to the specific ClHWS mutants generated by the inventors, but the skilled person can equally generate other mutations in the Clhws allele of watermelon and thereby generate other mutants which lead to at least a higher percentage of male flowers when in homozygous form. Various mutations can be generated and tested for the resulting phenotype, for example the regulatory elements can be mutated to reduce expression (knockdown) or eliminate expression (knock-out) of the allele and thus reduce or eliminate the amount of wild type ClHWS protein present in the cell or plant. Alternatively, mutations which lead to reduced function or loss-of-function of the ClHWS protein can be generated, i.e. mutations (such as missense mutations or frame shift mutations) which lead to one or more amino acids being substituted, inserted and/or deleted, or whereby the protein is truncated through the introduction of a premature stop-codon in the coding sequence (non-sense mutations). As the ClHWS protein comprises several conserved domains it is in one aspect encompassed that one or more amino acids are replaced, deleted and/or inserted in any one of these domains, as such mutations will likely reduced the protein function or result in a loss of function. Whether the mutation results in the expected phenotype (or combination of phenotypes) can then be tested by generating plants homozygous for the mutation and growing the plant line next to a wild type plant line and analysing the phenotypes of both lines, e.g. the percentage of male flowers, the ratio of male to female flowers, optionally the fusion of petals or male flower phenotype and/or the leaf shape phenotype.

Alternatively, the skilled person can carry out a method for production of a cultivated watermelon plant capable of producing a higher percentage of male flowers and/or a method for generating watermelon plants comprising mutant Clhws alleles comprising the steps of:

a) introducing mutations in a population of watermelon plants, plant parts or seeds, especially cultivated plants: or providing a population of mutated plants, preferably an M2 or M3 population, or progeny thereof;

b) selecting a mutated plant producing a modified leaf shape (e.g. more broadly lobed compared to the wild type, non-mutated plant line) and/or many male flowers (e.g. a higher percentage of male flowers than the wild type, non-mutated plant line, or a higher ratio of male to female flowers) and/or male flowers with fused petals or phenotypically different male flowers (compared to the wild type, non-mutated control plant line);

c) optionally determining if the plant selected under b) comprises a mutant allele of a ClHWS gene; and d) optionally growing the plants obtained under c).

Steps b) and c) can also be switched, so that step b) is selecting a plant comprising a mutant allele of a ClHWS gene and step c) is determining if the plant (or a progeny thereof) produce a modified leaf shape and/or many male flowers and/or male flowers with fused petals or male flowers having a different phenotype/having a different appearance.

Step a) can be carried out by e.g. mutagenizing seeds of one or more lines or varieties of watermelon, for example by treatment with mutagenizing agents such as chemical mutagens, e.g. EMS (ethyl methane sulphonate), or irradiation with UV radiation. X-rays or gamma rays or the like. The population may for example be a TILLING population. Preferably the mutagenized plant population has been selfed at least once (e.g. to produce an M2 generation, or M3, M4, etc.) prior to carrying out the next step, step b) or c).

The phenotyping of step b) can be easily done visually. The modified leaf shape is easily determined and is in one aspect the first sign that the endogenous mutant allele is present.

Such plants, or progeny thereof, can be tested for the presence of the mutant Clhws gene by further phenotypic analysis (e.g. letting flowers develop) and/or by genotyping the plants for mutations in the ClHWS gene and encoded protein, or expression of the ClHWS gene, sequencing and other methods known to the skilled person. There are, thus, various methods, or combinations of methods, for verifying if a phenotypically selected plant comprises a mutant allele of a ClHWS gene.

If step b) is the selection of plants comprising a mutant allele of the ClHWS gene, the skilled person can also use various methods for detecting the DNA, mRNA or protein of the ClHWS gene in order to identify a plant comprising a mutant Clhws allele. The genomic DNA of the wild type watermelon ClHWS gene, encoding a functional ClHWS protein (SEQ ID NO: 1) is the DNA of SEQ ID NO: 4 and the cDNA (mRNA) encoding the protein of SEQ ID NO: 1 is given in SEQ ID NO: 3. The promoter is upstream of this sequence and can e.g. be retrieved by sequencing or from the watermelon genome database. For example the at least 1000 or at least 2000 bases upstream of the ATG start include the promoter sequence.

In one aspect the mutant allele of the Clhws gene is a mutant allele resulting in reduced expression or no expression of the Clhws gene or is a mutant allele resulting in one or more amino acids of the encoded ClHWS protein being replaced, inserted or deleted, compared to the wild type ClHWS protein.

In one aspect the mutant allele of the ClHWS gene is obtainable by inducing mutations, either targeted or random, into the gene (promoter or other regulatory elements, splice sites, coding region, etc.) and selecting plants, e.g. from the progeny, comprising a mutant Clhws allele. In one aspect an allele comprising a mutation in a codon, especially in a codon of the F-box domain, or of the C-terminal region (starting at amino acid 93 and ending at amino acid 380 of SEQ ID NO: 1 or the equivalent region in a sequence comprising at least 90%, 91%, 92%,93%, 94%, 95%, 96%, 97%, 98% or 99% sequence identity to SEQ ID NO: 1), is selected, e.g. a mutation which causes an amino acid replacement, deletion, a frame shift or a stop-codon. In one aspect the mutant allele causes a truncation of the encoded watermelon ClHWS protein.

In a preferred aspect the truncation is at the C-terminal end and is long enough to result in a loss-of-function of the protein. Without limiting the invention, it is believed that the two truncated proteins generated herein (W204STOP and W229STOP) lack any in vivo function, as they lack 202 and 177 amino acids of the C-terminal end of the wild type protein of 405 amino acids. It is without undue burden, however, to generate other mutant alleles, which also lack C-terminal amino acids (e.g. at least the last 40, 45, 50, 60, 70, 80, 90, 100 or more C-terminal amino acids, including at least part of the C-terminal region of the beta-sheets, see FIG. 5) and also result a higher percentage of male flowers developing when in homozygous form. The C-terminal region forming the beta sheets runs from amino acid 93 to 380 of SEQ ID NO: 1. Therefore, in one aspect the truncation results in all or part of amino acids 93 to 380 of SEQ ID NO: 1 (or the equivalent region in a sequence comprising at least 90%, 91%, 92%,93%, 94%, 95%, 96%, 97%, 98% or 99% sequence identity to SEQ ID NO: 1) being absent.

In one aspect the SNP marker Adenine (A) at nucleotide 101 of SEQ ID NO: 5 (marker m WM23348454) is detected in the genome of a watermelon plant or plant part, or DNA therefrom. This SNP marker detects the allele comprising the W204STOP mutation in SEQ ID NO: 1 in watermelon (or the W245STOP codon in SEQ ID NO: 8).

In one aspect the SNP marker Adenine (A) at nucleotide 101 of SEQ ID NO: 5 (marker mWM23348454), which corresponds to an Adenine for nucleotide 611 in SEQ ID NO: 3 and 4, and to an Adenine for nucleotide 1798 in SEQ ID NO: 8, is detected in the genome of a watermelon plant or plant part, or genomic DNA or cDNA therefrom. Therefore, a method for detecting the presence of an Adenine (mutant) or a Guanine (wild type) at nucleotide 611 of SEQ ID NO: 3 or 4 (or in a sequence comprising at least 90% identity to SEQ ID NO: 3 or 4), or at nucleotide 1798 of SEQ ID NO: 8 (or in a sequence comprising at least 90% identity to SEQ ID NO:8) is provided herein. Thus, genomic DNA or cDNA of watermelon can be screened for the presence of an A (mutant) or G (wild type) for nucleotide 101 of SEQ ID NO: 5 and a plant or plant part comprising the A can optionally be selected.

For other mutant Clhws alleles, such as those in Table A and B, similar SNP markers (or other markers) and SNP genotyping (or other genotyping) assays can easily be designed. Thus, allele specific markers and detection methods are encompassed herein, especially for any mutant allele which results in an amino acid insertion, deletion or replacement in the F-box domain or in the C-terminal region (starting at amino acid 93 and ending at amino acid 380) of a ClHWS protein of watermelon.

Especially in one aspect the genotype of marker mWM2334845 can be determined and used to select plants or progeny plants comprising a Adenine at nucleotide 101 of SEQ ID NO: 5 and thus comprising the mutant Clhws allele in which the encoded ClHWS protein is truncated and lacks all amino acids downstream (C-terminal) of amino acid 203 of SEQ ID NO: 1 (or the corresponding amino acid of a sequence comprising at least 90% identity to SEQ ID NO: 1).

The diploid plant heterozygous for Clhws (i.e. Clhws ClHWS) will be heterozygous for the SNP marker. e.g. will have the genotype 'AG' for nucleotide 101 of SEQ ID NO: 5 (i.e. the plant comprises one chromosome having a Adenine, A, at nucleotide 101 of SEQ ID NO: 5 or at nucleotide 101 of a sequence comprising at least 90%, 91%, 92%, 93%, 94%, 95%, 96%, 97%, 98% or more sequence identity to SEQ ID NO:5 and a second chromosome having a Guanine, G, at nucleotide 101 of SEQ ID NO: 5 or at nucleotide 101 of a sequence comprising at least 90%, 91%, 92%, 93%, 94%, 95%, 96%, 97%, 98% or more sequence identity to SEQ ID NO:5), while a plant homozygous for Clhws (i.e. Clhws Clhws) will have the genotype 'AA' for nucleotide 101 of SEQ ID NO: 5 (i.e. the plant comprises two chromosomes which both have a Adenine, A, at nucleotide 101 of SEQ ID NO: 5 or at nucleotide 101 of a sequence comprising at least 90%, 91%, 92%, 93%, 94%, 95%, 96%, 97%, 98% or more sequence identity to SEQ ID NO:5).

The marker m WM23348454 was designed based on the induced mutation of nucleotide 611 (Guanine) in the genomic DNA of the wild type ClHWS gene of SEQ ID NO: 4 to Adenine (G611→A), whereby the codon TGG (encoding Trp or W) is changed into the codon TAG encoding a STOP codon, resulting in a translation stop and a truncated ClHWS protein. Thus, nucleotide 611 of the genomic ClHWS sequence of SEQ ID NO: 4 corresponds to nucleotide 101 of marker mWM23348454 of SEQ ID NO: 5. As genomic DNA and cDNA/mRNA are identical, nucleotide 611 of the cDNA/mRNA ClHWS sequence of SEQ ID NO: 3 corresponds to nucleotide 101 of marker mWM23348454 of SEQ ID NO: 5. The marker can thus also be used to screen cDNA/mRNA or genomic DNA for this mutation. Nucleotide 1798 of the genomic ClHWS sequence of SEQ ID NO: 8 also corresponds to nucleotide 101 of marker mWM23348454 of SEQ ID NO: 5.

Mutant-allele-specific markers and marker assays can equally easily be developed for any mutant Clhws allele, as the underlying genomic change, e.g. in a codon, can be used to design a marker assay to detect the genomic change, e.g. underlying the amino acid changes disclosed herein or other genomic changes in the mutant Clhws allele compared to the wild type ClHWS allele.

Using such allele-specific markers, which detect specific mutant Clhws alleles, genotyping can be carried out to detect the presence and copy number of the allele in plants and plant material (or DNA derived therefrom). So in diploids, the marker genotype for the above mutant Clhws allele (underlying the W204STOP change of the protein in watermelon) is 'AA' when the mutant allele is in homozygous form. In triploids or tetraploids the marker genotype can be used to determine copy number of the mutant allele. The genotype may thus for example be AAA if three copies are present in a triploid, or AAAA if for copies are present in a tetraploid, or AAG if two copies are present in a triploid, etc.

Plants, Seeds and Plant Parts

In one embodiment a cultivated watermelon plant or seed is provided, or a part thereof (such as a cell, a tissue, organ, fruit, etc.), comprising at least one copy of a mutant allele of a gene named ClHWS, said mutant allele conferring at least a significantly higher percentage of male flowers when the mutant allele is in homozygous form.

In one aspect the mutant allele is a mutant allele of the watermelon gene which encodes the ClHWS protein of SEQ ID NO: 1 or a protein comprising at least 90%, 91%, 92%, 93%, 94%, 95%, 96%, 97%, 98% or 99% sequence identity to SEQ ID NO: 1 (wild type functional protein), whereby the mutant allele has a reduced expression or no expression, or whereby the mutant allele encodes a mutant ClHWS protein comprising one or more amino acids replaced, inserted and/or deleted compared to the wild type protein.

In one embodiment the one or more amino acid replacements, insertions or deletions comprise or consist of the replacement, insertion or deletion of one or more amino acids in one or more of the conserved F-box domain and/or the C-terminal region (amino acid 93 to 380). The mutant protein has a reduced-function or loss-of-function compared to the wild type protein (and thus compared to a wild type plant comprising the wild type ClHWS gene), preferably the plant comprising the mutant allele in homozygous form produces a modified phenotype as described herein.

When referring herein to a specific nucleotide or amino acid position, e.g. at amino acid 204 of SEQ ID NO: 1, "or at amino acid 204 of a sequence comprising at least 90%, 91%, 92%, 93%, 94%, 95%, 96%. 97%, 98% or 99% sequence identity to the SEQ ID NO", this means that the nucleotide or amino acid is present in a variant sequence at a nucleotide or amino acid corresponding to the same nucleotide or amino acid (e.g. corresponding to amino acid 204 of SEQ ID NO: 1) in the variant sequence, i.e. in a sequence comprising at least 90%, 91%, 92%, 93%, 94%, 95%, 96%, 97%, 98% or 99% sequence identity to the mentioned SEQ ID NO. It may for example be that the variant sequence is one or a few nucleotides or amino acids shorter, but when one pairwise aligns the variant sequence with the mentioned SEQ ID NO, one can see which nucleotide or amino acid of the variant sequence corresponds to the same nucleotide or amino acid.

The mutant allele is a mutation in an endogenous gene of cultivated watermelon. The existence of a gene conferring a modified phenotype, as described herein, enables the skilled person to generate other de novo mutants in the gene, e.g. in any cultivated line or variety.

The skilled person can, without undue burden, generate plants according to the invention, e.g. by carrying out a method for generation and/or identification of ClHWS mutants in a mutant population or by targeted gene editing of the ClHWS gene.

As mentioned above, as the ClHWS gene has been identified to be the gene encoding a protein of SEQ ID NO: 1 (wild type watermelon protein) in normal watermelon plants, the same or other mutants than the ones generated by the inventors can be generated de novo.

As natural variation may exist in the wild type, functional ClHWS proteins, the wild type ClHWS protein need not be 100% identical to the protein of SEQ ID NO: 1 but may have less sequence identity to SEQ ID NO: 1, e.g. at least 90%, 91%, 92%, 93%, 94%, 95% 96%, 97%, 98%, 99% or 99.5% or 99.6%, 99.7%, 99.8% or 99.9% when aligned pairwise over the entire length to SEQ ID NO: 1 In one aspect the conserved F-box domain, and/or the N-terminal region, and/or the C-terminal region is however 100% identical to that of SEQ ID NO: 1, so that the variation of at least 90% identity lies outside of the one or more or all of the conserved domains or regions.

As mentioned, a mutant allele of a ClHWS protein-encoding gene causes a plant to produce at least a high percentage of male flowers, optionally further also fused petals or male flowers having a different appearance and/or modified leaf shape, when the plant is homozygous for the mutant allele, especially a diploid plant homozygous for the mutant allele and optionally a triploid plant comprising at least one, two or three copies of the mutant allele or a tetraploid plant comprising at least two or four copies of the mutant allele. Concerning the embodiments of the invention, the mutation in the mutant allele of a ClHWS protein-encoding gene can be any mutation, including deletions, truncations, insertions, point mutations, nonsense mutations, missense or non-synonymous mutations, splice-site mutations, frame shift mutations and/or mutations in regulatory sequences. In one aspect the mutation in the mutant allele of a ClHWS protein-encoding gene is a point mutation. The mutation can occur in a DNA sequence comprising the coding sequence of a ClHWS protein-encoding gene or in an RNA sequence encoding a ClHWS protein or it can occur in the amino acid of a ClHWS protein. Concerning a DNA sequence of a ClHWS protein-encoding gene the mutation can occur in the coding sequence or it can occur in non-coding sequences like 5'- and 3'-untranslated regions, promoters, enhancers etc. of a ClHWS protein-encoding gene. In respect to RNA encoding a ClHWS protein the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted and/or deleted at the C-terminal end of the protein or in one or more of the conserved domains of the protein. For example, truncation of the protein to cause deletion of at least 10, 15, 20, 25, 30, 40, 50, 100, 150, 170, 177, 200, 202 or more amino acids of the C-terminal end of the wild type protein will result in a mutant protein which causes a modified phenotype in comparison to the wild type plant, as was shown by the W204STOP mutant protein.

Similarly, mutations whereby any of the conserved domains or highly structured regions (such as the C-terminal region comprising the beta-sheets) are deleted, all or in part, or are replaced by one or more different amino acids, will result in a loss of function or decrease of function of the protein.

For example, a stop codon mutation e.g. in the N-terminal part preceding the conserved F-box domain or in the F-box domain results in a truncated protein having a reduced function or loss of function.

Likewise, amino acid insertions, deletions or replacements in the N-terminal part preceding the C-terminal region or in the C-terminal region can result in a protein having a reduced function or loss of function.

Any mutant allele can be analysed for the phenotype when the allele is in homozygous form in e.g. diploid plants, to see if indeed the plant comprises a change in e.g. flowering, flower morphology and/or leaf morphology, as described.

One embodiment of the invention, therefore, concerns plant cells or plants according to the invention comprising a mutant allele of a ClHWS protein-encoding gene characterized in that the mutant allele comprises or effects one or more of the mutations selected from the group consisting of a) a deletion, truncation, insertion, point mutation, nonsense mutation, missense or non-synonymous mutation, splice-site mutation, frame shift mutation in the genomic sequence;

b) a mutation in one or more regulatory sequences;

c) a deletion, truncation, insertion, point mutation, nonsense mutation, missense or non-synonymous mutation, splice-site mutation, frame shift mutation in the coding sequence;

d) a deletion, truncation, insertion, point mutation, nonsense mutation, missense or non-synonymous mutation, splice-site mutation, frame shift mutation in the pre-mRNA or mRNA; and/or e) a deletion, truncation, insertion or replacement of one or more amino acids in the ClHWS protein.

In one aspect the mutant allele results in reduced expression or no expression of the ClHWS gene or the mutant allele encodes a protein having a decreased function or a loss-of-function.

Reduced expression or no expression means that there is a mutation in a regulatory region of the ClHWS gene, such as the promoter, whereby reduced mRNA transcript or no mRNA transcript of the ClHWS allele is being made, compared to plants and plant parts comprising a wild type ClHWS allele. The decrease in the expression can, for example, be determined by measuring the quantity of mRNA transcripts encoding ClHWS protein, e.g. using Northern blot analysis or RT-PCR. Here, a reduction preferably means a reduction in the amount of RNA transcripts by at least 50%, in particular by at least 70%, optionally by at least 85% or by at least 95%, or even by 100% (no expression) compared to the plant or plant part comprising a wild type ClHWS gene. Expression can be analysed e.g. in flower tissue or leaf tissue.

In one aspect the protein comprising one or more amino acids replaced, inserted or deleted compared to the wild type protein. Thus, for watermelon, one or more amino acids are inserted, deleted or replaced compared to the wild type ClHWS protein of SEQ ID NO: 1 or a wild type ClHWS protein comprising at least 90%, 91%, 92%, 93%, 94%, 95%, 96%, 97%, or 98% or 99% sequence identity to SEQ ID NO: 1: whereby the mutant protein has reduced function or loss of function compared to the wild type protein and thus results in i) only male flowers developing or a larger percentage of male flowers developing or a larger ratio of male to female flowers developing than in the homozygous wild type plant and further optionally ii) male flowers frequently but not always having fused petals or male flowers having a different appearance and/or iii) the plant having differently shaped leaves, when the mutant allele is present in homozygous form in a diploid plant.

In one aspect the wild type ClHWS protein comprises the conserved F-box domain. Thus in one aspect the mutant allele is a mutant allele of the gene ClHWS, which gene encodes a wild type protein of SEQ ID NO: 1 (watermelon) or a wild type protein comprising at least 90%, 91%, 92%, 93%, 94%, 95%, 96%, 97% or 98% or 99% sequence identity to SEQ ID NO: 1, and whereby the wild type protein comprises the conserved F-box domain of amino acids 45 to 83 of SEQ ID NO: 1.

In one aspect the wild type ClHWS protein comprises the C-terminal region. Thus in one aspect the mutant allele is a mutant allele of the gene ClHWS, which gene encodes a wild type protein of SEQ ID NO: 1 (watermelon) or a wild type protein comprising at least 90%, 91%, 92%, 93%, 94%, 95%, 96%, 97% or 98% or 99% sequence identity to SEQ ID NO: 1, and whereby the wild type protein comprises the C-terminal region of amino acids 93 to 380 of SEQ ID NO: 1.

In one aspect the wild type ClHWS protein comprises the N-terminal region. Thus in one aspect the mutant allele is a mutant allele of the gene ClHWS, which gene encodes a wild type protein of SEQ ID NO: 1 (watermelon) or a wild type protein comprising at least 90%, 91%, 92%, 93%, 94%, 95%, 96%, 97% or 98% sequence identity to SEQ ID NO: 1, and whereby the wild type protein comprises the N-terminal region of amino acids 1 to 44 of SEQ ID NO: 1.

In one aspect the wild type ClHWS protein comprises the conserved F-box domain and the C-terminal region, i.e. any variation of the functional wild type protein is outside this conserved domain or region.

In another aspect the wild type ClHWS protein comprises the conserved F-box domain and the C-terminal region and the N-terminal region, i.e. any variation of the functional wild type protein is outside these conserved domains or regions.

The mutant alleles of the above wild type alleles are in one aspect mutant alleles having reduced expression or no expression (through e.g. mutations in the promoter or enhancer elements) or producing a mutant protein which comprises one or more amino acids inserted, deleted or replaced compared to the wild type protein, whereby the mutant protein has a reduced function or no function in vivo, as can be determined when the mutant allele is in homozygous form in a plant and by analysing the phenotype (or combination of phenotypes) of the plant homozygous for the mutant allele compared to the plant homozygous for the wild type allele. The same phenotypic analysis can be done for a mutant allele having reduced gene expression or no gene expression. Thus, any mutant allele can be made homozygous in the plant and the phenotype can be compared to the control plant comprising the original, non-mutated allele.

In one aspect, therefore, a mutant Clhws allele is provided encoding a mutant protein wherein the W204 or W229 of SEQ ID NO: 1 (or a sequence comprising at least 90% identity to SEQ ID NO: 1), is replaced by another amino acid or is deleted, e.g. the codon being replaced by a STOP codon.

When amino acids from one amino acid to another amino acid are mentioned herein this includes the start/first and end/last amino acid mentioned.

When referring to an amino acid being 'deleted', this includes a mutation whereby the codon is changed into a stop codon, or the codon is deleted, or a mutation whereby there is a frameshift, resulting in the amino acid not be encoded. Equally, when referring to an amino acid being 'replaced', this includes a mutation whereby the codon encodes a different amino acid, or a codon is inserted, or a mutation whereby there is a frameshift resulting in a different amino acid being encoded.

The plants and plant parts comprising at least one copy of a mutant Clhws allele may be plants of the family Cucurbitaceae, especially cultivated species such as watermelon (*Citrullus lanatus*). Also plants and plant parts of the family Cucurbitaceae, especially watermelon, comprising two copies of a mutant Clhws allele are encompassed herein.

In one aspect the mutant Clhws allele is heterozygous in a diploid plant cell or plant, e.g. in a diploid watermelon plant. In another aspect the mutant Clhws allele is homozygous in a diploid plant cell or plant.

The plant cells and plants are preferably cultivated plants, such as elite breeding lines or varieties, and not wild plants. Watermelon may be any type of watermelon.

Watermelon plants, and parts thereof, which comprises at least one copy of the mutant Clhws allele, may be diploid, tetraploid or triploid. In another aspect it may be another polyploid, e.g. a pentaploid, hexaploid, heptaploid, octaploid, etc. A tetraploid plant comprising four copies of Clhws can for example be used to make an octaploid, by doubling the chromosomes. Crossing such an octoploid with a diploid homozygous for Clhws will result in a pentaploid comprising five copies of Clhws. In one aspect the polyploidy watermelon plant comprises at least one copy of the mutant Clhws allele, but it may also comprise more copies, e.g. in a preferred aspect a triploid plant comprises two or three copies of a mutant Clhws allele or a tetraploid comprises two or four copies of a mutant Clhws allele.

A diploid plant may, thus, have the genotype Clhws/ClHWS (heterozygous for the mutant allele) or Clhws/Clhws (homozygous for the mutant allele). In one aspect the diploid plant comprising the Clhws allele in homozygous form is a double haploid plant (DH), e.g. a double haploid watermelon, plant or plant cell or plant part.

A triploid watermelon plant may have the genotype Clhws/ClHWS/ClHWS or Clhws Clhws/ClHWS or Clhws/Clhws/Clhws. The triploid plant with genotype Clhws/ClHWS/ClHWS can be made by crossing a wild type female tetraploid (ClHWS/ClHWS/ClHWS1/ClHWS) with a diploid male homozygous for the mutant allele (Clhws/Clhws). The triploid plant with genotype Clhws/Clhws/ClHWS can be made by crossing a female tetraploid (Clhws/Clhws/Clhws/Clhws) with a diploid male homozygous for the wild type allele (ClHWS/ClHWS).

A tetraploid watermelon plant may have the genotype Clhws/ClHWS/ClHWS/ClHWS or Clhws/Clhws/ClHWS/ClHWS or Clhws/Clhws/Clhws ClHWS/or Clhws/Clhws/Clhws/Clhws. The genotypes Clhws/Clhws/ClHWS/ClHWS can be made by doubling the chromosomes of a diploid Clhws/ClHWS. The genotypes Clhws/Clhws/Clhws/Clhws can be made by doubling the chromosomes of a diploid Clhws/Clhws. The other two genotypes, Clhws/ClHWS/ClHWS/ClHWS and Clhws/Clhws/Clhws/ClHWS can for example be made by crossing two tetraploids of genotype Clhws/Clhws/ClHWS/ClHWS and identifying the genotypes in the progeny.

In one aspect the watermelon plant is homozygous for Clhws, in another aspect it is heterozygous for Clhws. In one aspect it is an inbred line or a variety. In a further aspect it is an F1 hybrid.

Seeds from which any of the watermelon plants described can be grown (comprising at least one mutant Clhws allele) are also encompassed herein, as are parts of such a plant, such as flowers, cells, roots, fruits, rootstocks, scions, leaves, stems, vegetative propagations, cuttings, and also in vitro cell- or tissue cultures, as well as pollen, microspores, ovaries, etc. are encompassed herein.

Diploid Watermelon Plants Comprising a Mutant Clhws Allele

In one aspect the watermelon plant is a diploid line (e.g. an inbred line) or variety, comprising at least one mutant copy of Clhws, preferably two mutant copies (i.e. is homozygous for Clhws). In one aspect the diploid plant homozygous for Clhws will produce a phenotype of i) only male flowers developing or a larger percentage of male flowers developing or a larger ratio of male to female flowers developing than in the homozygous wild type plant, and optionally further ii) male flowers frequently but not always having fused petals or male flowers having a different appearance and/or iii) the plant having differently shaped leaves.

In the specific mutant allele identified herein (W204*) all these three phenotypes were seen together, but it is also possible that other mutants in the Clhws allele may not show the combination of all three phenotypes, for example the fusion of the petals may be absent or less frequent or the leaf shape may be less easily differentiated from the wild type leaves than the leaves shown in FIG. 3 (left foto). Such mutants, which vary in their phenotype regarding fused petals or male flower appearance and/or leaf shape are encompassed herein, as long as the mutants comprise an increased percentage of male flowers being produced compared to the wild type plant. So, the effect of the mutant allele on increasing the percentage of male flowers or increasing the ratio of male to female flowers over the percentage and ratio seen in the plants homozygous for the functional wild type allele is the most important effect for using such plants as pollenizers. Therefore, any such mutant alleles which result in phenotype i) described herein are encompassed herein and phenotypes ii) and/or iii) are optionally present or a present in slightly different degrees.

Furthermore, although the mutant Clhws allele which comprises the W204* mutation confers phenotypes i), ii) and iii) in the original genetic background in which it was generated, the expression of phenotypes ii) and iii) were somewhat different in a different genetic background (see Example 2).

Therefore, in one aspect the diploid watermelon plant comprises one or two copies of a mutant Clhws allele, which allele (when in homozygous form) confers at least the phenotype described under i), namely: only male flowers developing or a larger percentage of male flowers or a larger ratio of male to female flowers developing than in the control plant which is homozygous for the functional wild type ClHWS allele. Optionally the phenotypes described under ii) and/or iii) may also be conferred by the mutant allele.

Seeds from a diploid plant, comprising one or two copies of a mutant Clhws allele, can be grown are also encompassed herein, as are parts of such a plant, such as flowers, leaves, stems, vegetative propagations, cells, cuttings, fruits and also in vitro cell- or tissue cultures, as well as pollen, microspores, anthers, ovaries, rootstocks, scions, etc. are encompassed herein. Thus, in one embodiment the diploid plant, or seeds from which the plant can be grown, or tissue or parts of the plant (pollen, anthers, microspores) comprises a mutant Clhws allele as described herein.

In one aspect the diploid plant (or plant part or seed) comprises one copy of the mutant Clhws allele which encodes a truncated protein, e.g. the mutant protein of SEQ ID NO: 2, comprising only amino acids 1 to 203 of the wild type protein and lacking the remaining amino acids or the mutant protein comprising only amino acids 1 to 228 of the wild type protein and lacking the remaining amino acids.

In one aspect the diploid plant (or plant part or seed) comprises two copies of the mutant Clhws allele which encodes a truncated protein, e.g. the mutant protein of SEQ ID NO: 2, comprising only amino acids 1 to 203 of the wild type protein and lacking the remaining amino acids or the mutant protein comprising only amino acids 1 to 228 of the wild type protein and lacking the remaining amino acids.

In one aspect the diploid plant (or plant part or seed) is provided which comprises one or two copies of the mutant Clhws allele wherein in the genomic DNA nucleotide 611 of SEQ ID NO: 4 is an Adenine or wherein in the genomic DNA nucleotide 1798 of SEQ ID NO: 8 is an Adenine.

In one aspect the diploid plant (or plant part or seed) is provided which comprises one or two copies of the mutant Clhws allele wherein in the genomic DNA nucleotide 687 of SEQ ID NO: 4 is an Adenine or wherein in the genomic DNA nucleotide 1874 of SEQ ID NO: 8 is an Adenine.

In one aspect the diploid plant (or plant part or seed) comprises one or two copies of the mutant Clhws allele as described in Tables A and B.

In one aspect the diploid plant (or plant part or seed) comprises any other mutant Clhws allele as described herein, resulting in homozygous form in the modified phenotype described.

Use as Pollenizer

The diploid plants comprising a mutant Clhws allele in homozygous form are in one aspect used as pollenizer, to provide pollen for other watermelon plants, such as diploid watermelon plants or triploid watermelon plants.

Thus, for diploid watermelon plants comprising two copies of a mutant Clhws allele a method of producing seeded (pollinating other diploid plants) or seedless (pollinating triploid plants) fruits is provided. Thus, in one aspect a method for growing diploid watermelon plants to produce pollen is provided, comprising the steps: seeding or planting diploid watermelon plants comprising two copies of a mutant Clhws allele in their genome, preferably in the vicinity of diploid or triploid watermelon plants comprising wild type copies of the ClHWS gene, and harvesting the seeded or seedless watermelon fruits which develop on those plants.

When the plant comprising the mutant Clhws allele in homozygous form is used to provide pollen to pollinate the flowers of diploid plants lacking the mutant allele, the pollen will contain one copy of the mutant allele and the seeds that develop in the fruits will, therefore, also contain one copy of the mutant allele. Such fruits and seeds are therefore encompassed herein.

When the plant comprising the mutant Clhws allele in homozygous form is used to provide pollen to pollinate the flowers of triploid plants, the pollen only induces fruit set and the developing fruits are seedless.

A method for producing seedless fruits on triploid hybrid watermelon plants is provided, said method comprising:

(a) providing a diploid watermelon plant comprising two copies of a mutant Clhws allele and a triploid watermelon plant.

(b) allowing pollination of the flowers of the triploid plant with pollen of the diploid plant, or pollinating the flowers of the triploid plant with pollen of the diploid plant, and optionally (c) harvesting the (seedless) fruits produced on the triploid plant.

Step a) may comprise growing the diploid watermelon plant near or in the vicinity of the triploid plant or it may comprise collecting flowers or pollen from the diploid plant and pollinating the flowers of the triploid plant in step b).

The method may be carried out in the field or in controlled environments such as tunnels or glasshouses.

The flowers and/or the pollen or stamen of the pollenizer plants may, thus, in one aspect be collected, e.g. by hand and optionally stored until needed for pollination.

In the field, the method may involve seeding or transplanting the diploid pollenizer and the triploid plants into a field.

There are various methods to do this, e.g. pollenizer plants may be planted in separate rows from the triploid plants (e.g.

1 row pollenizer plants followed by e.g. 2 to 4 rows of triploid plants, i.e. ratios of 1:2, 1:3, 1:4) or may be interplanted within rows of triploid plants or in-between rows of triploid plants (but not in separate pollenizer rows). Triploid plants are normally planted on hills in a row, and one strategy is to plant the pollenizer on e.g. every third or fourth hill, with the other hills being triploids. Another strategy is to plant the pollenizer not on the hills, but between the hills.

Bees move the viable pollen from the male flowers of the pollenizer to the female (fruit bearing) flowers of the triploid watermelon. Placing the pollenizer in the row with triploid plants rather than in separate rows can be a plus because honey bees often work down a row rather than across rows.

Thus, basically, in the triploid production field, the pollenizer plant described herein (comprising two mutant Clhws alleles) may be interplanted at regular intervals in the same row (e.g. 1, 2, 3 or 4 consecutive triploid plants followed by one pollenizer plant, etc.), or rows of triploid hybrids and pollenizer plants may alter at certain intervals (e.g. 1, 2, 3 or 4 rows of triploids followed by one row of pollenizer plants). Alternatively, the triploids are planted in rows and the pollenizer plants are planted at regular intervals in-between rows.

Thus, a field may comprising triploid hybrid watermelon seedlings and the pollenizer seedling according to the invention in a ratio of 5:1, 4:1, 3:1, 2:1 or 1:1.

In one embodiment each of 5, 4, 3, 2 or 1 consecutive plants are triploid hybrid watermelon seedling followed by at least one pollenizer seedling according to the invention. Optionally each of the consecutive triploid hybrid plants may also be followed by 1, 2 or 3 pollenizer seedling according to the invention.

In another embodiment the field comprises rows of only triploid hybrids and rows of only pollenizer seedlings, whereby the ratio of triploid rows to pollenizer rows is 5:1, 4:1, 3:1, 2:1, or optionally 1:1.

Optimal distances between plants and between rows may vary greatly depending on location, growing conditions, etc. Distances between plants may thus be any distance, such as about 3 feet (about 90 cm), about 4 feet (about 120 cm), about 5 feet (about 150 cm) or about 6 feet (about 180 cm) or more.

Any triploid hybrid may be used, such as known triploid hybrid varieties.

The triploid hybrids and/or the pollenizer plants may be grafted to a different rootstock, as often rootstocks are used to increase stress and/or disease tolerance of the plants. Such grafted plants, especially a plant comprising a scion which is a diploid pollenizer plant comprising two mutant alleles of the Clhws gene and a different rootstock are encompassed herein.

A method is, therefore, provided comprises seeding or growing diploid watermelons plants comprising two copies of a mutant Clhws allele in a cultivation area, such as a field or greenhouse or tunnel, near or in the vicinity of diploid or triploid watermelon plants and allowing pollination of the flowers of the diploid or triploid watermelon plants and optionally harvesting the fruits.

In a specific aspect the diploid pollenizer plant (comprising two copies of a mutant Clhws allele as described herein) is further homozygous for the mutant multibranching allele, whereby the pollenizer plant has a multibranching growth type and, as shown in the examples, produces many male flowers over an extended period.

In one aspect the plant comprising at least one copy but preferably two copies of a mutant Clhws allele, therefore, further comprises at least one copy but preferably two copies of a mutant multibranching allele. This may be any mutant multibranching allele, but in one aspect the mutant multibranching allele encodes the protein of SEQ ID NO: 9. In one aspect, therefore, the mutant multibranching allele comprises the genomic DNA of SEQ ID NO: 10, or a sequence comprising substantial sequence identity to SEQ ID NO: 10 and which due to the degeneracy of the genetic code also encodes the protein of SEQ ID NO: 9. However, the mutant multibranching allele may also be a different mutant allele at the locus, as long as the mutant allele confers a multibranching growth type when in homozygous form.

With this pollenizer, one can e.g. plant one pollenizer plant between each third, or each fourth or each fifth triploid (or diploid) watermelon plant for optimum pollination.

Also watermelon plants, which are heterozygous for a mutant Clhws allele and are heterozygous for a mutant multibranching allele are encompassed herein, as such plants are useful in making homozygous plants.

Likewise watermelon plants, which are homozygous for a mutant Clhws allele and are heterozygous for a mutant multibranching allele are encompassed herein.

Vegetative Propagation and Plant Tissue Culture

The diploid pollenizer plants can also be reproduced vegetatively (clonally) and such vegetatively propagated plants, or 'vegetative propagations' are an embodiment of the invention. They can easily be distinguished from other watermelon plants by the presence of a mutant Clhws allele and/or phenotypically. The presence of one or more mutant Clhws alleles can be determined as described elsewhere herein.

Vegetative propagations can be made by different methods. For example, one or more scions of a plant of the invention may be grafted onto a different rootstock, e.g. a biotic or abiotic stress tolerant rootstock.

Other methods include in vitro cell or tissue culture methods and regeneration of vegetative propagations from such cultures. Such cell or tissue cultures comprise or consist of various cells or tissues of a plant of the invention. In one aspect such a cell or tissue culture comprises or consists of vegetative cells or vegetative tissues of a plant of the invention.

In another aspect a cell or tissue culture comprises or consists of reproductive cells or tissues, such as anthers, pollen, microspores or ovules of a plant of the invention. Such cultures can be treated with chromosome doubling agents to make e.g. double haploid plants, or they can alternatively be used to make haploid plants (e.g. to make diploids from a tetraploid or to make haploids from a diploid).

An in vitro cell or tissue culture may, thus, comprise or consist of cells or protoplasts or plant tissue from a plant part selected from the group consisting of: fruit, embryo, meristem, cotyledon, pollen, microspores, ovule, leaf, anther, root, root tip, pistil, flower, seed, stem. Also, parts of any of these are included, such as e.g. only the seed coat (maternal tissue).

Thus, in one aspect of the invention a cell culture or a tissue culture of cells of a plant comprising one or two copies of a mutant Clhws allele, all as described above, is provided. As mentioned, a cell culture or a tissue culture comprises cells or protoplasts or plant tissue from a plant part of a plant comprising a mutant Clhws allele may comprise or consist of cells or tissues selected from the group consisting of: embryo, meristem, cotyledon, pollen, microspore, leaf, anther, root, root tip, pistil, flower, seed, stem: or parts of any of these.

Also provided is a watermelon plant regenerated from such a cell culture or tissue culture, wherein the regenerated plant (or progeny thereof, e.g. obtained after crossing or selfing the regenerated plant) comprises the mutant Clhws allele. Therefore, in one aspect the watermelon plant comprising a mutant Clhws allele in one or more copies is a vegetatively propagated watermelon plant.

In a different aspect the cells and tissues of the invention (and optionally also the cell or tissue culture), comprising a mutant Clhws allele in one or more copies, are non-propagating cells or tissues.

Further Methods

A method for seedless triploid watermelon fruit production is provided, said method comprising:

1. providing a diploid watermelon plant or seed comprising two copies of a mutant Clhws allele,
2. providing a triploid hybrid (F1) watermelon plant or seed lacking a mutant Clhws allele,
3. planting or seeding said triploid hybrid plants in a field (or greenhouse or tunnel) and planting or seeding the diploid watermelon plants of step 1 in the same field (or greenhouse or tunnel), and optionally
4. harvesting the seedless watermelon fruits produced on the triploid plants, whereby the fruits are produced after pollination of the female flowers with pollen comprising a mutant Clhws allele.

A method for watermelon fruit production is provided, said method comprising:

1. providing a diploid watermelon plant or seed comprising two copies of a mutant Clhws allele.
2. providing a watermelon plant or seed lacking a mutant Clhws allele (comprising only wild type Clhws alleles).
3. allowing pollen comprising the mutant Clhws allele to be transferred to the female flowers of the plant of step 2 (either by insects or by hand), optionally
4. harvesting the watermelon fruits produced on the plants, whereby the fruits are produced after pollination of the female flowers with pollen comprising a mutant Clhws allele.

Also provided is a method for production of a watermelon plant capable of producing a high percentage of male flowers or only male flowers, or a method for producing mutant alleles of the ClHWS gene, comprising the steps of a) introducing mutations in a population of watermelon plants or providing a mutant population of watermelon plants; or providing watermelon plants comprising randomly induced mutations or targeted induced mutations in the ClHWS target gene,
b) selecting a plant comprising a mutant allele of the Clhws gene;
c) optionally verifying if the plant selected under b) produces a higher percentage of male flowers when the mutant Clhws allele is in homozygous form, compared to a control plant which comprises the wild type alleles of the ClHWS gene.

A watermelon plant comprising at least one copy of a mutant Clhws allele produced by the above method and/or a mutant Clhws allele induced and identified by the above method is encompassed.

The population of watermelon plants under a) is preferably a single genotype of a cultivated watermelon breeding line or variety, which is treated/has been treated with (or subjected to) a mutagenic agent, or progeny of such a population e.g. obtained after selfing individuals of the population to produce M2, M3 or further generation plants. This may for example be a TILLING population. It may also be a watermelon line which has been subjected to targeted gene modification using e.g. Crispr based methods.

In step b) the selection of a plant comprising a mutant allele of the Clhws gene can be carried out phenotypically and/or by screening the plants (or plant parts or DNA therefrom) for the presence of a mutant allele of the Clhws gene, i.e. an allele which either has reduced expression or no expression of the wild type ClHWS allele or an allele encoding a mutant ClHWS protein.

Regarding the screening for the phenotype or combination of phenotypes, it is understood that these can only be selected if the mutant Clhws allele is in homozygous form and if the mutant allele has reduced expression or no expression or encodes a reduced function or loss-of-function protein, so that the phenotype or combination of phenotypes is seen. The screening for the phenotype or combination of phenotypes can be done as described, e.g. growing a line comprising the mutant Clhws allele in homozygous form under the same growth conditions as a control line or variety comprising the wild type ClHWS allele in homozygous form and then analysing one or more of a) counting male and female developing over a specified period (a period wherein the control plant produces male and female flowers), b) determining if the male flowers frequently have fused petals or a different male flower phenotype in the mutant line and/or c) determining if the leaf shape is different in the mutant line.

Regarding the screening or selection of the plants for the presence of a mutant allele of the ClHWS gene, this can be done by various methods which detect ClHWS DNA, RNA or protein, for example by e.g. designing PCR primers which amplify part of the coding region or all of the coding region to amplify the genomic DNA in order to determine if a plant comprises a mutation in the genomic DNA, or other methods.

Thus, to determine the presence or select a plant comprising a mutant Clhws allele is present various methods can be used. For example, marker analysis or sequence analysis of the chromosome region comprising the ClHWS locus can be carried out, or PCR or RT-PCR can be used to amplify the Clhws allele (or a part thereof) or the mRNA (cDNA) or sequencing can be done. Also genetic analysis to determine the recessive inheritance may be carried out.

If gene editing methods have been used the vector/construct that has been introduced into the plant to induce the mutations in the allele is preferably removed from the plant line comprising the mutant Clhws allele, so that the plant line does not comprise such a vector or construct.

In a further aspect a method of producing seeds of a pollenizer plant comprising a mutant Clhws allele in homozygous form is provided, said method comprising.

i) using a pollenizer plant, which is homozygous for a mutant Clhws allele, as male parent in a cross with a watermelon female parent plant which is heterozygous for a mutant Clhws allele, ii) harvesting the seeds produced from said cross, and optionally iii) selecting from the seeds or seedlings of ii) those which are homozygous for the mutant Clhws allele.

The seeds produced in step ii) will be a mix of seeds which comprise the mutant allele in heterozygous form (Clhws/ClHWS) and seeds comprising the mutant allele in homozygous form (Clhws/Clhws), with about 50% of each genotype. As in one aspect seedlots comprising the mutant allele in homozygous form or seedlings comprising the mutant allele in homozygous form are to be sold, the heterozygous seeds or seedlings are preferably discarded. In one aspect the selection in step iii) can be done using non-destructive seed genotyping methods or by germinating the seeds and selecting seedlings based on e.g. DNA analysis and/or based on selecting seedlings having a modified leaf shape.

A seedlot enriched for seeds comprising the mutant Clhws allele in homozygous form is an aspect of the invention, wherein at least 80%, 90%, 95%, 96%, 97%, 98%, 99% or 100% of seeds in the seedlot are homozygous for the mutant Clhws allele.

Also, seedlings (e.g. a container comprising the seedlings, such as trays) enriched for seedlings comprising the mutant Clhws allele in homozygous form, wherein at least 80%, 90%, 95%, 96%, 97%, 98%, 99% or 100% of the seedlings are homozygous for the mutant Clhws allele.

In one aspect the seedlings are selected based on a modified leaf shape and placed in e.g. trays, to be sold as pollenizer plants.

Also, the use of a pollenizer watermelon plant as described for producing seedless triploid watermelon fruits is provided, whereby the pollen of the pollenizer induces fruit set on the female flowers of the triploid plants.

Further the use of a mutant Clhws allele for generating pollenizer watermelon plants and/or pollen for pollinating other watermelon plants is provided.

In one aspect the plants, plant parts and plant cells according to the invention are not exclusively obtained by means of an essentially biological process as defined by Rule 28 (2) EPC (European Patent Convention).

In one aspect the plants are non-GMO (i.e. they do not contain a genetic construct inserted into the genome through transformation).

In one aspect the mutant alleles are generated by mutagenesis (e.g. chemical or radiation mutagenesis) or by targeted mutagenesis, especially using the CRISPR system (e.g. Crispr/Cas9 or Crispr/Cpf1 or other nucleases). In one aspect the cultivated plant comprising the mutant Clhws allele is not a transgenic plant, i.e. non-transgenic progeny are selected which do not comprise e.g. the CRISPR construct.

In one aspect the mutant allele of the ClHWS gene comprises a human induced mutation, i.e. a mutation introduced by mutagenesis techniques, such as chemical mutagenesis or radiation mutagenesis, or targeted mutagenesis techniques, such as Crispr based techniques.

A method for targeted mutagenesis of the endogenous ClHWS gene in watermelon is provided herein, using any targeted gene modification method, such as CRISPR based methods (e.g. Crispr/Cas9 or Crispr/Cpf1), TALENS. Zine Fingers or other methods.

In one aspect an isolated mutant ClHWS protein and an isolated wild type ClHWS protein is provided or an isolated nucleic acid molecule encoding a mutant ClHWS protein or a wild type ClHWS protein. Also an antibody able to bind a mutant or wild type ClHWS protein is encompassed herein.

Detection Methods

In one aspect a screening method for identifying and/or selecting seeds, plants or plant parts or DNA from such seeds, plants or plant parts comprising in their genome a mutant allele and/or a wild type allele of a ClHWS protein-encoding gene is provided.

The method comprises screening at the DNA, RNA (or cDNA) or protein level using known methods, in order to detect the presence of the mutant allele and/or of the wild type allele. There are many methods to detect the presence of a mutant and/or wild type allele of a gene.

Thus, a method for screening and/or selecting plants or plant material or plant parts, or DNA or RNA or protein derived therefrom, for the presence of a mutant Clhws allele and/or a wild type ClHWS allele is provided comprising one or more of the following steps:

a) determining the gene expression of the endogenous ClHWS gene, e.g. to detect if it is reduced or abolished;

b) determining the amount of wild type ClHWS protein, e.g. to detect if it is reduced or abolished;

c) determining if a mutant and/or wild type mRNA, cDNA or genomic DNA encoding a mutant or wild type ClHWS protein is present;

d) determining if a mutant and/or wild type ClHWS protein is present;

e) determining if plants or progeny thereof show a mutant phenotype (as described) or a wild type phenotype.

Routine methods can be used, such as RT-PCR, PCR, antibody-based assays, sequencing, genotyping assays (e.g. allele-specific genotyping), phenotyping, etc.

The plants or plant material or plant parts may be watermelon plants or plant materials or plant parts, such as leaves, leaf parts, cells, fruits, fruit parts, ovaries, stem, hypocotyl, seed, parts of seeds, seed coat, embryo, etc.

For example, if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP-assay method.

Equally other genotyping assays can be used. For example, a TaqMan SNP genotyping assay, a High-Resolution Melting (HRM) assay. SNP-genotyping arrays (e.g. Fluidigm, Illumina, etc.) or DNA sequencing may equally be used.

In one aspect for example the SNP marker mWM23348454 at nucleotide 101 of SEQ ID NO: 5, or at nucleotide 101 of a sequence comprising at least 92%, 93%, 94%, 95%, 96%, 97%, 98%, 99% or more sequence identity to SEQ ID NO: 5, can be used to detect the presence or absence of a mutant Clhws allele encoding a mutant protein comprising a W204STOP mutation in watermelon. Based on the difference between the genomic sequence of the wild type allele and the mutant allele, the skilled person can easily develop markers which can be used to detect specific alleles.

Also provided herein is a method for identifying a watermelon plant (or plant part) comprising a mutant Clhws allele, the method comprising detecting in the plant (or plant part) the presence of a mutant Clhws allele, wherein the presence is detected by at least one marker within the Clhws allele or by detecting the protein encoded by the Clhws allele. The method for detecting the mutant Clhws allele is selected from the group consisting of PCR amplification, nucleic acid sequencing, nucleic acid hybridization and an antibody-based assay (e.g. immunoassay) for detecting the ClHWS protein encoded by the allele.

Also provided herein is a method for identifying a watermelon plant (or plant part) comprising a mutant Clhws allele comprising a mutation in a regulatory element, the method comprising detecting in the plant (or plant part) the reduced gene expression or absence of gene expression of the mutant Clhws allele, wherein the presence is detected by mRNA levels (cDNA) of the wild type ClHWS allele or by detecting the protein levels of the wild type ClHWS protein. The method for detecting the mutant Clhws allele is selected from the group consisting of PCR amplification (e.g. RT-PCR), nucleic acid sequencing, western blotting and an antibody-based assay (e.g. immunoassay) for detecting the ClHWS protein encoded by the allele.

Also provided is a method for determining, or detecting or assaying, whether a cell or tissue of a watermelon plant or plant part comprises a mutant allele of a gene named ClHWS encoding a protein of SEQ ID NO: 1, or a protein comprising at least 90%, 91%, 92%, 93%, 94%, 95%, 96%, 97%, 98% or 99% sequence identity to SEQ ID NO: 1, is provided herein. In one aspect the method comprises determining the expression of the allele, and/or determining the coding sequence of the allele and/or determining part of the coding sequence of the allele (e.g. a SNP genotype of the allele), and/or determining the amino acid sequence of the protein produced and/or the amount of protein produced.

Various method can be used to determine whether a plant or part thereof comprises a mutant Clhws allele of the invention. As mentioned, the mRNA (or cDNA) level of the wild type allele may be determined, or the wild type protein level may be determined, to see if there is a reduced expression or no expression of the wild type allele. Also, the coding sequence or part thereof may be analysed, for example if one already knows which mutant allele may be present, an assay can be developed to detect the mutation, e.g. a SNP genotyping assay can e.g. distinguish between the presence of the mutant allele and the wild type allele, e.g. genotyping for marker m WM23348454.

A method for selection of a plant or plant part comprising the steps of:

a) identifying a plant or plant part which has a mutation in an allele encoding a ClHWS protein, wherein the wild type allele of the gene encodes a ClHWS protein comprising at least 90%, 91%, 92%, 93%, 94%, 94%, 95%, 96%, 97%, 98% or 99% sequence identity to any one of the proteins selected from the group of: SEQ ID NO:1, and optionally b) determining whether the plant, or a progeny plant, produces a higher percentage of male flowers than a plant not having a mutant Clhws allele (being homozygous for the wild type Clhws allele) and/or flowers with fused petals or different male flower phenotype and/or leaves with different shape and optionally c) selecting a plant comprising at least on copy of the mutant allele of step a).

A method for production of a plant comprising the steps of:

a) introducing mutations in a population of plants.

b) selecting a plant producing a higher percentage of male flowers and/or flowers with fused petals and/or leaves and/or comprising a mutant Clhws allele.

c) optionally verifying if the plant selected under b) has a mutation in an allele encoding a ClHWS protein-encoding gene and selecting a plant comprising such a mutation, and optionally d) growing/cultivating the plants obtained under c), wherein the wild type allele of the gene encodes a ClHWS protein comprising at least 90%, 91%, 92%. 93%, 94%, 95%, 96%, 97%, 98% or 99% sequence identity to the protein of: SEQ ID NO:1.

A method for production of a plant comprising the steps of:

a) introduction of a foreign nucleic acid molecule into a plant, wherein the foreign nucleic acid molecule is chosen from the group consisting of i) DNA molecules, which code at least one antisense RNA, which effects a reduction in the expression of an endogenous gene encoding a ClHWS protein;

ii) DNA molecules, which by means of a co-suppression effect lead to the reduction in the expression of an endogenous gene encoding a ClHWS protein;

iii) DNA molecules, which code at least one ribozyme, which splits specific transcripts of an endogenous gene encoding a ClHWS protein;

iv) DNA molecules, which simultaneously code at least one antisense RNA and at least one sense RNA, wherein the said antisense RNA and the said sense RNA form a double-stranded RNA molecule, which effects a reduction in the expression of an endogenous gene encoding a ClHWS protein (RNAi technology);

v) nucleic acid molecules introduced by means of in vivo mutagenesis, which lead to a mutation, or an insertion of a heterologous sequence, in an endogenous gene encoding a ClHWS protein, wherein the mutation or insertion effects a reduction in the expression of a gene encoding a ClHWS protein or results in the synthesis of a loss-of-function or reduced function ClHWS protein;

vi) nucleic acid molecules, which code an antibody, wherein the antibody results in a reduction in the activity of an endogenous gene encoding a ClHWS protein due to the bonding of the antibody to an endogenous ClHWS protein;

vii) DNA molecules, which contain transposons, wherein the integration of these transposons leads to a mutation or an insertion in an endogenous gene encoding a ClHWS protein, which effects a reduction in the expression of an endogenous gene encoding a ClHWS protein, or results in the synthesis of an inactive protein;

viii) T-DNA molecules, which, due to insertion in an endogenous gene encoding a ClHWS protein, effect a reduction in the expression of an endogenous gene encoding a ClHWS protein, or result in the synthesis of a loss-of-function or reduced function ClHWS protein;

ix) nucleic acid molecules encoding rare-cleaving endonucleases or custom-tailored rare-cleaving endonucleases preferably a meganuclease, a TALENs or a CRISPR/Cas system b) selecting a plant or progeny of a plant, wherein the plant, or a progeny of the plant, produces a higher percentage of male flowers and/or flowers with fused petals or male flowers with a different phenotype and/or leaves, optionally c) verifying if the plant or progeny selected under b) has a decreased activity of a ClHWS protein compared to wild type plants into whose genome e.g. no foreign nucleic acid molecules had been integrated, optionally d) growing/cultivating the plants obtained under c).

A plant obtained by any of the methods above is encompassed herein.

In one aspect a genetically modified plant and plant part is provided, whereby the plant has reduced expression or no expression of the endogenous ClHWS gene, e.g. through silencing of the endogenous ClHWS gene. Such a plant may be any plant, in one aspect it is a watermelon. However, it can also be a cucumber, melon, pepper, maize, soybean, wheat, canola, tomato, cotton, etc.

In another aspect a watermelon plant and plant part is provided, comprising a mutation in the endogenous ClHWS gene, e.g. an induced mutation generated e.g. by targeted mutagenesis, whereby either the gene expression is reduced or abolished or the expressed gene encodes a reduced function or loss of function ClHWS protein compared to the wild type protein.

Also provided herein is a method for screening (e.g. genotyping) genomic DNA of watermelon plants, seeds or plant parts comprising the steps of:

a) providing a sample (or a plurality of samples) of genomic DNA of a watermelon plant or of a plurality of plants (e.g. a F2 population, inbred lines, a backcross population, a breeding population, hybrid plants, etc.).

b) providing a pair of PCR primers or an oligonucleotide probe, which primers or (oligonucleotide) probe comprise at least 10, 11, 12, 13, 14, 15, 16, 17, 18, 19, 20, 21, 22 or more consecutive nucleotides of the genomic allele of the Clhws gene and can hybridize to the genomic allele and/or amplify part of the genomic allele in a PCR assay, and c) carrying out a PCR assay using the primer pair or a hybridization assay using the probe of step b) on the sample(s) of step a), and optionally d) selecting a plant or plant part or seed comprising one or two copies of an allele (e.g. a wild type allele and/or a mutant allele) of the Clhws gene in the genome, wherein the wild type allele of the Clhws gene encodes the protein of SEQ ID NO: 1.

In step b) a PCR primer pair is at least one forward primer, complementary to one of the DNA strands of the Clhws allele and one reverse primer complementary to the other DNA strand of the Clhws allele, which primer pair hybridizes to the denatured genomic DNA and amplifies part of the Clhws allele in a PCR reaction. Primers can be designed to amplify the wild type or any mutant Clhws allele using primer design tools. In one aspect two forward primers are used, one designed to amplify the wild type allele and one designed to amplify a mutant allele of the Clhws gene, and one common reverse primer. These three primers can be used in a KASP-assay to genotype the samples of step a). Thus, in one aspect the assay in step c) is a KASP-assay, but also other genotyping assays can be used, such as those described in world wide web at biosearchtech.com/sectors/agrigenomics/agrigenomics-per-qper-technologies.

In one aspect the assay discriminates between a wild type and a mutant allele of the Clhws gene, e.g. between the wild type Clhws allele of SEQ ID NO: 4 and a mutant Clhws allele as described herein.

For analyzing the genomic DNA at least crude genomic DNA extraction may be necessary. The presence of a mutant allele or a wild type allele in the genomic DNA can be detected directly or indirectly. Directly may for example be by nucleic acid hybridization of e.g. oligonucleotide probes. Indirectly may for example be by nucleic acid amplification using e.g. PCR primers which comprise e.g. a tail sequence attached to the primer and during PCR the allele-specific primer binds to the template DNA and elongates, thereby attaching the tail sequence to the newly synthesized strand and in subsequent PCR rounds a FRET cassette (fluorescent resonant energy transfer cassette) binds to the tail and emits fluorescence. The fluorescent signal can then be detected. This is used e.g. in the KASP-assay.

The mutant allele may differ from the wild type allele in various aspects, e.g. in the promoter sequence or in the protein coding sequence or in the intron/exon splice sites. The mutant allele may have a reduced gene expression or no gene expression or it may result in the production of a protein comprising one or more amino acids deleted, replaced, or inserted compared to the wild type protein.

In one aspect the mutant allele is an allele encoding a protein comprising one or more amino acids inserted, replaced or deleted relative to the wild type protein as described herein, e.g. see alleles encoding mutant proteins in Table A or others described herein.

Also, methods of generating and/or selecting plants or plant parts comprising at least one mutant allele of the watermelon Clhws gene in their genome is provided.

In one aspect also a method for detecting the presence of a wild type allele and/or of a mutant allele of the watermelon Clhws gene in the genome is provided.

In one aspect a method for detecting whether a watermelon plant or plant part or seed comprises at least one copy of the wild type allele, encoding the protein of SEQ ID NO: 1 and/or comprises at least one copy of a mutant allele (as described herein) is provided and optionally selecting a plant, plant part or seed comprising at least one copy of a mutant allele.

Also, a KASP-assay (Kbioscience Kompetitive Allele specific PCR-genotyping Assay) is provided comprising two allele specific forward primers, e.g. a FAM primer and a VIC primer and a Common reverse primer. See also Examples. Allele specific primers can easily be developed to detect and/or discriminate between the wild type allele (encoding e.g. the protein of SEQ ID NO: 1) and a mutant allele comprising e.g. one or more amino acids replaced, duplicated, deleted or inserted with respect to the wild type protein.

Likewise, isolated sequences or molecules of the (wild type or mutant) genomic sequence, the cDNA or mRNA sequence, protein sequences, as well as oligonucleotide primers or probes for detecting a wild type or mutant allele of the watermelon Clhws gene are encompassed herein.

Also a method for generating a PCR amplification product and/or a oligonucleotide hybridization product of (a part of the) genomic DNA of watermelon plants, seeds or plant parts is provided comprising the steps of:

a) providing a sample (or a plurality of samples) of genomic DNA of a watermelon plant or of a plurality of plants (e.g. a F2 population, inbred lines, a backcross population, a breeding population, hybrid plants, etc.), b) providing at least a pair of PCR primers or at least one oligonucleotide probe, which primers or (oligonucleotide) probe comprise at least 10, 11, 12, 13, 14, 15, 16, 17, 18, 19, 20, 21, 22 or more consecutive nucleotides of the genomic allele of the Clhws gene and can hybridize to the genomic allele and/or amplify part of the genomic allele in a PCR assay, and c) carrying out a PCR assay using the primer pair or a hybridization assay using the probe of step b) on the sample(s) of step a) to generate a PCR amplification product and/or a oligonucleotide hybridization product, and optionally d) selecting a plant or plant part or seed comprising one or two copies of an allele (e.g. a wild type allele and/or a mutant allele) of the Clhws gene in the genome, wherein the wild type allele of the Clhws gene encodes the protein of SEQ ID NO: 1.

Further a method for amplifying and/or hybridizing (a part of the) genomic DNA of watermelon plants, seeds or plant parts is provided comprising the steps of:

a) providing a sample (or a plurality of samples) of genomic DNA of a watermelon plant or of a plurality of plants (e.g. a F2 population, inbred lines, a backcross population, a breeding population, hybrid plants, etc.), b) providing at least a pair of PCR primers or at least one oligonucleotide probe, which primers or (oligonucleotide) probe comprise at least 10, 11, 12, 13, 14, 15, 16, 17, 18, 19, 20, 21, 22 or more consecutive nucleotides of the genomic allele of the Clhws gene and can hybridize to the genomic allele and/or amplify part of the genomic allele in a PCR assay, and c) carrying out a PCR assay using the primer pair or a hybridization assay using the probe of step b) on the sample(s) of step a) to generate a PCR amplification product and/or a oligonucleotide hybridization product, and optionally d) selecting a plant or plant part or seed comprising one or two copies of an allele (e.g. a wild type allele and/or a mutant allele) of the Clhws gene in the genome.

wherein the wild type allele of the Clhws gene encodes the protein of SEQ ID NO: 1.

Also a genotyping kit comprising primers and/or probes and reaction components to amplify and/or hybridize part of the genomic DNA of the Clhws gene is provided.

Primers and probes are preferably labelled or modified by e.g. a tail sequence or label, to be able to detect the amplification or hybridization reaction products.

In one aspect a method is provided for detecting, and optionally selecting, a watermelon plant, seed or plant part comprising at least one copy of a wild type allele and/or of a mutant allele of a gene named Clhws (*Citrullus lanatus* hws), comprising the steps of:

a) providing one or more genomic DNA samples of one or more watermelon plants, seeds or plant parts, b) carrying out a genotyping assay, using the DNA samples of a) as template, that discriminates between the wild type Clhws allele and the mutant Clhws allele, wherein said genotyping assay is based on nucleic acid amplification making use of Clhws allele-specific oligonucleotide primers, and/or wherein said genotyping assay is based on nucleic acid hybridization making use of Clhws allele-specific oligonucleotide probes, and optionally c) selecting a plant, seed or plant part comprising one or two copies of the mutant allele.

wherein the wild type Clhws allele comprises the sequence of SEQ ID NO: 4 and the mutant Clhws allele comprises one or more nucleotides inserted, duplicated, deleted or replaced with respect to the sequence of SEQ ID NO: 4.

In the method above said Clhws allele-specific oligonucleotide primers or said Clhws allele-specific oligonucleotide probes may comprise at least 10 nucleotides of SEQ ID NO: 4 or of the complement strand of SEQ ID NO: 4.

In the above method the mutant allele may comprise at least one codon inserted or duplicated in the coding region of the allele, or at least one codon changed into another codon, or at least one codon deleted or changed into a STOP codon.

The mutant allele for example encodes a protein of Table A, or another protein comprising one or more amino acids inserted, deleted or replaced with respect of the wild type, functional Clhws protein, as described.

The oligonucleotide primers or oligonucleotide probes may comprise at least 15 nucleotides complementary to SEQ ID NO: 4 or to the complementary sequence of SEQ ID NO: 4.

The genotyping assay is in one aspect a KASP-assay, said KASP-assay comprises a first forward primer detecting the wild type allele of SEQ ID NO: 4 in the DNA sample, a second forward primer detecting the mutant allele comprising one or more nucleotides inserted, deleted or replaced with respect to SEQ ID NO: 4 in the DNA sample, and one common reverse primer.

Further provided is a synthesized nucleic acid primer or probe, wherein said primer or probe comprises at least 15 nucleotides of SEQ ID NO: 4, or of the complement sequence of SEQ ID NO: 4.

Also encompassed is a method for detecting, and optionally selecting, a watermelon plant, seed or plant part comprising at least one copy of a wild type Clhws allele and/or of a mutant Clhws allele of a gene named Clhws (*Citrullus lanatus* hws) comprising the steps of:

a) providing one or more genomic DNA samples of one or more watermelon plants, seeds or plant parts,
   b) carrying out a genotyping assay, using the DNA samples of a) as template, wherein said genotyping assay is based on nucleic acid amplification making use of Clhws allele-specific oligonucleotide primers, and/ or wherein said genotyping assay is based on nucleic acid hybridization making use of Clhws allele-specific oligonucleotide probes, and optionally
   c) selecting a plant, seed or plant part comprising one or two copies of the mutant allele.
   wherein the wild type Clhws allele encodes the protein of SEQ ID NO: 1 and the mutant Clhws allele comprises one or more amino acids inserted, deleted or replaced with respect to SEQ ID NO: 1.

In the above method said Clhws allele-specific oligonucleotide primers or said Clhws allele-specific oligonucleotide probes comprise at least 10 nucleotides of SEQ ID NO: 4 or of the complement strand of this sequence.

Also one aspect is a method for identifying or detecting a cultivated watermelon plant, plant part or seed (or DNA of any of these) comprising a mutant Clhws allele:

screening a watermelon plant, plant part or seed (or DNA of any of these) using a molecular marker assay which detects at least one of SNP marker which differentiates a mutant Clhws allele from a wild type Clhws allele; and
   identifying and/or selecting a plant, plant part or seed comprising the SNP nucleotide which is specific for the mutant Clhws allele.

In one aspect the method comprises selecting plants, plant parts or seeds comprising two copies of a mutant Clhws allele. In one aspect the method is used to separate seeds or plants comprising two copies of a mutant Clhws allele from other plants or seeds.

Sequence Description

SEQ ID NO 1: wild type ClHWS protein of watermelon
   SEQ ID NO: 2: mutant ClHWS protein of watermelon, comprising a W204STOP
   SEQ ID NO: 3: cDNA encoding the wild type ClHWS protein
   SEQ ID NO 4: genomic DNA encoding the wild type ClHWS protein: nucleotides 610, 611 and 612 are TGG (codon for W) in this wild type sequence. In the sequence encoding the W204STOP protein, nucleotide 611 is mutated to A, thus nucleotides 610, 611 and 612 are TAG (stop codon).
   SEQ ID NO 5: SNP marker m WM23348454 at nucleotide 101 (G/A) for detecting either the mutant Clhws allele or wild type ClHWS allele. In the wild type allele the codon TGG encodes W, W204 of SEQ ID NO: 1. In the mutant allele the G is changed to A (G→A), and the resulting mutated codon TAG is a STOP codon. Thus the SNP marker comprises an A at nucleotide 101 of SEQ ID NO: 5 or at the equivalent nucleotide of a sequence comprising at least 90%, 91%, 92%, 93%, 94%, 95%, 96%, 97%, 98%, 99% or more sequence identity to SEQ ID NO: 5, can be used to detect the mutant Clhws allele, while the SNP marker comprising a G at nucleotide 101 of SEQ ID NO: 5, or at the equivalent nucleotide of a sequence comprising at least 90%, 91%, 92%, 93%, 94%, 95%, 96%, 97%, 98%, 99% or more sequence identity to SEQ ID NO: 5, can be used to detect the wild type ClHWS allele.

SEQ ID NO 6: amino acid sequence of *Arabidopsis* At3g61590
   SEQ ID NO 7: protein named ClCG05G000990
   SEQ ID NO 8: genomic DNA described to encode the protein ClCG05G000990. Nucleotide 1188 to the end of the sequence (nucleotide 2405) correspond to SEQ ID NO: 4. Nucleotides 1188, 1189 and 1190 are the translation start codon of SEQ ID NO: 4. Nucleotide 1797, 1798 and 1799 correspond to nucleotides 610, 611 and 612 in SEQ ID NO: 4. Therefore, the change of nucleotide 1798 from G to A corresponds to the change of nucleotide 611 from G to A (TGG→TAG).
   SEQ ID NO 9: mutant multibranching protein comprising a duplication of 8 amino acids compared to the wild type multibranching protein
   SEQ ID NO 10: genomic DNA encoding the mutant multibranching protein of SEQ ID NO: 9
   SEQ ID NO 11: wild type multibranching protein
   SEQ ID NO 12: genomic DNA encoding the wild type multibranching protein of SEQ ID NO: 11

Any patent applications, patents and publications mentioned herein are herein incorporated by reference. Especially patent applications and patents mentioning the multibranching allele (or HMBN allele or DWARF14 allele), which causes multibranching (also referred to as multibranching growth type) when the mutant allele is in homozygous form. The multibranching gene is located on chromosome 8 of the watermelon genome, especially the gene is located in a region starting at base 28794281 and ending at base 28795173 of chromosome 8 of the Charleston Grey chromosome.

EXAMPLES

Example 1

A watermelon mutant population (developed via EMS treatment) was screened with a forward screening approach in Italy and one mutant with a modified leaf shape was found.

A single plant of the plant having the modified leaf shape was selected and used to make several F2 mapping populations in different genetic backgrounds.

The QTL was mapped to a 0.27 Mb/1.5 CM region on chromosome 5.

There were two mutations within this interval, one which was intergenic and one that introduced a premature stop codon in a gene encoding a protein.

In the cucurbitgenomics.org database of the Charleston Grey genome the gene was designated ClCG05G000990. However, further analysis of RNA data revealed that the gene was wrongly annotated in the database and that the protein containing the premature stop codon was shorter than the one in the database. The protein was found to be 405 amino acids long, while the protein indicated to be encoded by ClCG05G00090 was 446 amino acids long, due to the ATG start codon being 1187 nucleotides upstream of the ATG start codon of the identified gene, and there was also an intron in the upstream region, while the herein identified gene sequence did not contain an intron.

Blast analysis of the herein found gene identified the *Arabidopsis* gene At3g61590 as most similar protein (SEQ ID NO: 6). At3g61590 encodes a protein called HAWAIIAN SKIRT (AtHWS). The watermelon gene identified herein was, therefore, also named herein ClHWS.

The mutant ClHWS allele was found to be completely unique to this line when it was compared to 107 whole genome re-sequenced lines.

The phenotype of the plant homozygous for the mutant Clhws allele was that the leaf shape was different from the wild type (which was the phenotype first identified and mapped to find the gene), but also that the plant during its development did not produce female flowers. The male flowers that were produced frequently had fused petals and male flowers continued to develop during the growing season. An occasional female flower developed later in the growing cycle, but these did not develop fruits.

As the plant line produced male flowers, it was reproduced by using its pollen to pollinate the female flowers of a plant heterozygous for the mutant allele. Around 50% of the seeds that developed in the fruits of the cross were homozygous for the mutant Clhws allele and showed the phenotype of the original mutant line.

A marker was developed in order to detect the mutant allele encoding the W204STOP truncated protein in breeding. The marker was designed on the SNP at nucleotide 611 of SEQ ID NO: 4 (the genomic sequence), with SNP genotype AA indicating the mutant allele being present in homozygous form and GG indicating the wild type allele being present in homozygous form. The SNP marker, thus, differentiates between codon TGG and codon TAG, i.e. between W at amino acid 204 and a STOP codon.

```
marker m WM23348454 - SNP [A/G] at nucleotide 101 of SEQ ID NO: 5
tctgattata gtgcacttgc aat-
ttctgta aacagggttt cacacaacta tacaatctct        60
gttgtgaaat ccaagcaagt tcctggaaac ttctttcaat [A/G]ggatatatc aattcat-
att 120 tatgattcgg aaacgatgat gtgggttacc tctctgactg aagtcttgtc gggatg-
gaga        180 ggtggcgacg agagtgtgat t
```

The ClHWS gene is a single recessive gene and the phenotype co-segregated with the mutant Clhws allele in plants homozygous for the mutation (Clhws/Clhws) and homozygous for A at nucleotide 101 of SEQ ID NO: 5 (SNP genotype 'AA' for the SNP at nucleotide 101 of SEQ ID NO: 5).

The watermelon TILLING population was screened for further mutants in the ClHWS gene and identified a number of additional mutants in M2 lines.

TABLE B

| M2 line | SNP | Codon change | Change in protein of SEQ ID NO: 1 | Protein region affected | Phenotype observed in homozygous plants (Provean prediction for effect of amino acid substitution, see Example 3) |
|---|---|---|---|---|---|
| TP00026 | G/A | TGG (W) → TAG (STOP) | W204Stop | C-terminal beta sheets | Mainly male flowers, modified leaf shape and fused petals |
| TP02571-1 | G/A | GGG (G) → GAG (E) | G340E | C-terminal beta sheets | Not tested Provean prediction: neutral |
| TP04053-1 and/or TP03317-1 | G/A | GCT (A) → ACT (T) | A362T | C-terminal beta sheets | Not tested Provean prediction: neutral |
| TP04761-1 | G/A | TGG (W) → TGA (Stop) | W229Stop | C-terminal beta sheets | modified leaf shape (see Example 3) |
| TP05179-1 | G/A | GAG (E) → AAG (K) | E324K | C-terminal beta sheets | Not tested Provean prediction: neutral |
| TP05519-1 and/or TP05384-1 | C/T | TCT (S) → TTT (F) | S67F | F-box domain | Not tested Provean prediction: deleterious |

TABLE B-continued

| M2 line | SNP | Codon change | Change in protein of SEQ ID NO: 1 | Protein region affected | Phenotype observed in homozygous plants (Provean prediction for effect of amino acid substitution, see Example 3) |
|---------|-----|--------------|-----------------------------------|-------------------------|-----------------------------------------------------------------------------------------------------------------------|
| TP06018-1 | G/A | AGC (S) → AAC (N) | S348N | C-terminal beta sheets | Not tested Provean prediction: neutral |
| TP06205-1 | G/A | GGA (G) → GAA (E) | G228E | C-terminal beta sheets | Not tested Provean prediction: deleterious |
| TP07082-1 | C/T | CTT (L) → TTT (F) | L242F | C-terminal beta sheets | Not tested Provean neutral |
| TP03386-1 | G/A | AGA (R) → AAA (K) | R64K | F-box domain | Not tested Provean prediction: neutral |
| | G/A | GTT (V) → ATT (I) | V2191 | C-terminal beta sheets | Not tested Provean prediction: neutral |
| TP01284-1 | G/A | TGC(C) → TAC(Y) | C69Y | F-box domain | Not tested Provean prediction: deleterious |

ClHWS protein (SEQ ID NO: 1)
MEGQTSWIRHCYNDMSRDLEDLDSYLDFTNEGGKEAVAVSVESILPDDLLERILSYLPIASIFRAGSVC
KRWHDIVSSRRFLWNVSHILSQKPWYFMFTSSDEPIGYAYDPVLRKWYAINLPCIDKSNCFIASSCGLV
CEMDNDSRSELHVCNPITKCSMKLPEPTGSKFSDYSALAISVNRVSHNYTISVVKSKQVPGNFFQWDIS
IHIYDSETMMWVTSLTEVLSGWRGGDESVICDGVLYLLIYSTGGGAPDNRHGLVTYNISNHSSHGLLIR
SFIPAPCSLTCGRLMNLKQKLVMVGGIGKQDRPDIIKGIGIWILCGKEWREIARMPHKFFQGFGEFDDV
FASCGTDDLIYIQSYGAPALLTFDMNLRQWRWSQKCPVTKRFPLQLFTGFCFEPRLEINP Genomic sequence encoding the ClHWS protein (SEQ ID NO: 4)
with SNP [A/G] at nucleotide 611 in
bold (mWM23348454 is underlined)
ATGGAGGGACAAACGTCGTGGATAAGGCATTGCTACAATGACATGTCAAGAGATCTTGAAGATCTCGAT
TCTTACTTGGATTTCACAAATGAAGGAGGCAAAGAGGCTGTAGCAGTTTCTGTGGAGTCAATCCTGCCT
GATGACTTGTTGGAACGAATTCTGTCCTATCTACCGATAGCAAGCATTTTCAGAGCTGGTTCTGTGTGC
AAAAGATGGCATGATATAGTTAGTTCGAGGAGGTTTTTGTGGAATGTCTCACACATCCTATCACAAAAA
CCTTGGTATTTCATGTTTACAAGCTCTGATGAGCCTATTGGTTATGCCTATGATCCGGTTCTTAGAAAG
TGGTATGCTATTAATCTCCCGTGCATCGACAAGTCAAATTGCTTTATTGCCTCGTCATGTGGCTTGGTT
TGTTTCATGGACAATGACAGTCGAAGTGAGTTACATGTCTGCAACCCTATAACCAAATGCTCAATGAAA
TTACCAGAGCCCACGGGATCGAAGTTCTCTGATTATAGTGCACTTGCAATTTCTGTAAACAGGGTTTCA
CACAACTATACAATCTCTGTTGTGAAATCCAAGCAAGTTCCTGGAAACTTCTTTCAAT[A/G]GGATAT
ATCAATTCATATTTATGATTCGGAAACGATGATGTGGGTTACCTCTCTGACTGAAGTCTTGTCGGGATG
GAGAGGTGGCGACGAGAGTGTGATTTGTGATGGAGTTCTTTACCTCTTAATCTATTCAACTGGGGGTGG
AGCACCTGATAACCGCCACGGTCTTGTTACTTATAATATCTCTAACCATTCTTCTCATGGTCTGTTGAT
AAGAAGCTTCATTCCTGCTCCCTGTTCTCTCACATGCGGTCGATTGATGAATCTTAAGCAGAAGCTGGT
CATGGTTGGGGGAATTGGTAAACAGGATAGGCCTGACATCATTAAGGGGATTGGAATTTGGATTCTTTG
CGGGAAGGAGTGGCGAGAAATTGCACGCATGCCCCATAAGTTCTTCCAGGGATTTGGGGAGTTCGACGA
TGTTTTTGCCAGCTGCGGCACTGATGACCTTATTTACATCCAGAGCTATGGAGCTCCAGCTTTACTTAC
GTTTGACATGAATCTAAGACAATGGAGATGGTCGCAGAAGTGCCCAGTGACAAAGAGATTCCCTCTCCA
GCTTTTCACTGGCTTTTGCTTCGAACCAAGGCTTGAGATCAATCCCTGA

Example 2

The line containing the W204* mutant was crossed with a line having a different genetic background and F3 lines were generated containing the mutant allele in homozygous form. The new elite background is a line comprising the recessive multibranching gene (also referred to as Dwarf14 gene or HMBN allele as described in U.S. Pat. No. 7,314, 979B2) in homozygous form. The multibranching phenotype is caused by a mutant allele, which encodes a protein comprising a duplication of 8 amino acids (see below SEQ ID NO 9, wherein these 8 amino acids are duplicated: VGHSVSAM). When the mutant allele is in homozygous form, many more secondary branches are produced. Instead of about 20 secondary branches being formed (average number of secondary branches at 90 cm from crown), the plant homozygous for the mutant multibranching allele produces 45 or more secondary branches (average number of secondary branches at 90 cm from crown).

In variety Sidekick, the mutant multibranching allele is present in homozygous form. Sidekick is a commercial pollinator produced by HM Clause, see world wide web at //hmclause.com/wp-content/uploads/2021/11/USACAN-ADA_Watermelon_Sidekick_Techsheet_2014_ENG.pdf or world wide web at //hmclause.com/our-product-range/ (United States).

Mutant multibranching protein/Dwarf14 protein (SEQ ID NO: 9)

```
MVNNALLEAL NVRVLGTGDR SLVLAHGFGT DQSAWQLIYP SFTPYYRVIL YDLVCAGSVN   60

PDFFDFSRYT TLDAFVDDLI SILDSLHVHR CAFVGHSVSA MVGHSVSAMV GILASIRRPE  120

LFSKLILIGA SPRFLNDGDY HGGFEQSEID RVFAAMKANY QSWVNGFAPL AVGADVPAAV  180

QEFSRTLFNM RPDISLFVSK VIFSSDLRGV LGLVKVPCCI IQTAQDVSVP ASVAIYLRDH  240

LGGRNTVEML DTEGHLPHLS APQLLVRKLR RALSR                             275
```

Genomic DNA encoding mutant multibranching protein/
Dwarf14 protein (SEQ ID NO: 10)

```
atggttaaca acgcccttct tgaagccctt aatgtccgtg tcctcggcac cggcgaccgt   60
tctctggtcc tggcccatgg cttcggcacc gaccagtccg cttggcaact catttaccct  120
tcctttactc cttactaccg cgtcatcctt tacgaccttg tctgcgccgg tagcgtcaac  180
cccgacttct tcgatttctc ccgctacacc actctcgacg ccttcgtcga cgatctcatc  240
tccatcctag actctctcca cgtccaccgc tgcgcctttg tcggccactc cgtctccgcc  300
atggtcggcc actccgtctc cgccatggtc ggcatcctcg cctccatccg ccgtcccgaa  360
ctcttctcta agctcatctt aatcggcgcc tccccaaggt cctttccact tccacactct  420
gtttttctaa ctactctgtt tttttcccct gtttttataa aattcttttt attttttattt  480 ttttcaggtt cctcaacgac ggcgactacc acggtgggtt cgaacagagc gagattgaca  540
gggtcttcgc tgcaatgaag gctaattacc aatcctgggt caacggcttt gccctcttg  600 ctgtcggtgc cgatgttccc gctgccgttc aggaattcag ccggactctc ttcaatatga  660
gacccgacat ttccctcttc gtctctaagg tcatcttcag cagcgatctc cggggagtcc  720
tcggtctcgt caaagtcccc tgttgcataa ttcaaaccgc ccaagacgtc tctgttccgg  780
cctccgtcgc tatctacctc cgagaccacc tcggcggccg gaacaccgtg gagatgctcg  840
acaccgaagg ccacctaccc catctgagtg cccctcagct actcgtacgg aaactccgcc  900
gtgctctttc ccggtga                                                 917
```

Wild type multibranching protein/Dwarf14 protein (SEQ ID NO: 11)

```
MVNNALLEAL NVRVLGTGDR SLVLAHGFGT DQSAWQLIYP SFTPYYRVIL YDLVCAGSVN   60

PDFFDFSRYT TLDAFVDDLI SILDSLHVHR CAFVGHSVSA MVGILASIRR PELFSKLILI  120

GASPRFLNDG DYHGGFEQSE IDRVFAAMKA NYQSWVNGFA PLAVGADVPA AVQEFSRTLF  180

NMRPDISLFV SKVIFSSDLR GVLGLVKVPC CIIQTAQDVS VPASVAIYLR DHLGGRNTVE  240

MLDTEGHLPH LSAPQLLVRK LRRALSR                                      267
```

Genomic DNA encoding the wild type multibranching protein/
Dwarf14 protein (SEQ ID NO: 12)

```
atggttaaca acgcccttct tgaagccctt aatgtccgtg tcctcggcac cggcgaccgt   60
tctctggtcc tggcccatgg cttcggcacc gaccagtccg cttggcaact catttaccct  120
tcctttactc cttactaccg cgtcatcctt tacgaccttg tctgcgccgg tagcgtcaac  180
cccgacttct tcgatttctc ccgctacacc actctcgacg ccttcgtcga cgatctcatc  240
tccatcctag actctctcca cgtccaccgc tgcgcctttg tcggccactc cgtctccgcc  300
atggtcggca tcctcgcctc catccgccgt cccgaactct ctctaagct catcttaatc  360 ggcgcctccc aaggtccttt ccacttccac actctgtttt tctaactac tctgtttttt  420 tcccctgttt ttataaaatt ctttttattt ttattttttt caggttcctc aacgacggcg  480
actaccacgg tgggttcgaa cagagcgaga ttgacagggt cttcgctgca atgaaggcta  540
attaccaatc ctgggtcaac ggctttgccc tcttgctgt cggtgccgat gttcccgctg  600
```

-continued

```
ccgttcagga attcagccgg actctcttca atatgagacc cgacatttcc ctcttcgtct 660
ctaaggtcat cttcagcagc gatctccggg gagtcctcgg tctcgtcaaa gtcccctgtt 720
gcataattca aaccgcccaa gacgtctctg ttccggcctc cgtcgctatc tacctccgag 780
accacctcgg cggccggaac accgtggaga tgctcgacac cgaaggccac ctaccccatc 840
tgagtgcccc tcagctactc gtacggaaac tccgccgtgc tctttcccgg tga        893
```

A field trial was carried out with the mutant W204* in the original background line (indicated as TP00026-1 line) and in the multibranching genetic background (indicated as F3 line). The genetic control plants, lacking the mutant allele, were included in the trial.

Flowers were counted started at 8 weeks after transplant into the field. Once per week, for three weeks in a row, the new open male and female flowers were counted and labelled with a tag to avoid counting them double. The male and female flowers were counted on two plants for each of the four genotypes. For each plant the male and female flowers were counted on three of the branches of the plant. The average number over the three-week period is shown in the Table below.

| Background line | Growth phenotype | ClWHS allele (homo-zygous) | Average number of male flowers (percentage of total flowers) | Average number of female flowers (percentage of total flowers) | Ratio male flowers to female flowers | Ratio male flowers to female flowers |
|---|---|---|---|---|---|---|
| TP00026-1 line | Normal branching | Wild type | 4.25 (74%) | 1.5 (26%) | 74%:26% | 3:1 |
| TP00026-1 line | Normal branching | Mutant | 5.3 (91.4%) | 0.5 (8.6%) | 91.4%:8.6% | 11:1 |
| F3 line | multi-branching | Wild type | 5.0 (75.75%) | 1.6 (24.25%) | 75.75%:24.25 | 3:1 |
| F3 line | multi-branching | Mutant | 13.3 (100%) | 0 (0%) | 100%:0% | 13:0 |

The mutant Clhws allele (W204*) increased the average number of male flowers by 17% in the original elite line compared to the control and by 24% in the multibranching line compared to the control.

The combination of the mutant Clhws allele (in homozygous form) with the mutant multibranching allele (in homozygous form), therefore, increases the percentage of male flowers even more, maybe due to the increased number of secondary branches developing due to the multibranching gene. In U.S. Pat. No. 7,314,979B2 it is described that the multibranching mutant allele (in homozygous form) not only increases secondary branching but also the number of male flowers and female flowers. However, the F3 line with multibranching in homozygous form did not have significantly more male and female flowers than the normal branching TP00026-1 line. And in the line having the combination of multibranching mutant and Clhws mutant, female flowers were reduced to zero and male flowers were significantly increased.

As very few or no female flowers develop, also very few or no fruits develop on the plants. Even if occasional female flowers do develop, these generally do not lead to fruit set. This is a further advantage when using the plants as pollenizers in fields of triploid plants, as harvest of triploid fruits is not 'contaminated' with diploid fruits of the pollenizer plant. Also, as significantly more male flowers develop on each plant, fewer pollenizer plants are needed in a growing area in order to provide sufficient pollen.

Fotos of leaves and male flowers of the F3 line (multibranching background) are shown in FIG. 7 and FIG. 8.

FIG. 7, left side, shows the broader lobed leaf shape of the mutant is also seen in the multibranching background. FIG. 7, right side shows the wild type leaf shape of this multibranching line.

FIG. 8 (left side) shows that also the male flowers look different in the multibranching line than the wild type flowers of the multibranching line (right side).

Example 3

Two of the mutants of Example 1 were backcrossed to the recurrent parent and plants homozygous or heterozygous for the mutant allele were phenotyped when the first true leaves developed.

| Line backcrossed to recurrent parent | Change in protein of SEQ ID NO: 1 | Protein region affected | Phenotype observed in heterozygous plants | Phenotype observed in homozygous plants |
|---|---|---|---|---|
| TP04761-1 | W229Stop | C-terminal beta sheets | Wild type leaf shape | Broadly lobed leaf shape |
| TP03386-1 | R64K | F-box domain | Wild type leaf shape | Wild type leaf shape |

This example shows that the W229Stop mutant has the same modified leaf shape as the W204Stop mutant. Likely the percentage of male flowers will also be significantly increased in the plant.

As these two mutants lack 202 and 177 amino acids of the C-terminal end of the wild type protein, it is concluded that the truncated protein is non-functional. Therefore, it is also very likely that at least any other mutant allele that leads to a knock-out of gene expression or that results in a non-functional Clhws protein being made will (in homozygous form) result in a higher percentage of male flowers (or higher ratio of male to female flowers) than seen in plants which are homozygous for the wild type Clhws allele. However, also other mutant Clhws alleles, e.g. alleles which result in a reduced gene expression or a reduced protein function compared to the wild type allele, may also result in a higher percentage of male flowers developing. The skilled person can easily generate such mutant alleles and determine their phenotype when the allele is in homozygous form. The R64K mutant is an example of a mutant that does not result in a modified leaf shape and likely also not in a higher percentage of male flowers developing. This particular amino acid change is predicted by Provean prediction analysis to be 'neutral', i.e. it is predicted to not change protein function.

For the amino acid substitution mutants in Table B above, the predicted effect of the amino acid substitution on protein function was analyzed by Provean analysis, using the tool Provean Protein on the world wide web at http://provean.jcvi.org/index.php.

Out of all amino acid substitutions, only the S67F, C69Y and the G228E substitutions were predicted to be 'deleterious', i.e. to reduce or abolish protein function in vivo. Such predictions always have to be verified in vivo, as they are based on assumptions and computational analysis. The effect of S67F, C69Y and G228E will be analyzed by growing the homozygous plants and determining the phenotype (in comparison to plants having the wild type Clhws allele, e.g. the recurrent parent line). Vice versa, a amino acid substitution which is predicted to have a 'neutral' effect on protein function can also be wrong, i.e. the amino acid substitution may very well have an effect in vivo, as only about 78% of the Provean predictions are confirmed to be true in vivo.

The invention claimed is:

1. A watermelon plant or plant part comprising at least one copy of a mutant allele of a gene named ClHWS (*Citrullus lanatus* HAWAIIAN SKIRT), wherein said mutant allele encodes a mutant protein comprising one or more amino acids replaced, inserted or deleted in the C-terminal region starting at amino acid 93 and ending at amino acid 380 compared to the wild type protein, wherein said mutant allele confers an increase in the percentage of male flowers developing when the mutant allele is in homozygous form, and wherein the wild type watermelon allele comprises SEQ ID NO: 4.

2. The plant or plant part according to claim 1, wherein said mutant protein comprises truncations or deletions of all or part of the C-terminal region starting at amino acid 93 and ending at amino acid 380.

3. The plant or plant part according to claim 1, wherein plant further comprises at least one copy of a mutant multibranching allele, which mutant allele encodes the protein of SEQ ID NO: 9.

4. The plant or plant part according to claim 1, wherein said mutant allele comprises a mutation in the codon encoding amino acid number W204 or W229 of SEQ ID NO: 1.

5. The plant or plant part according to claim 4, wherein the codon for amino acid W204 or for amino acid W229 of SEQ ID NO: 1 is changed into a STOP codon.

6. The plant or plant part according to claim 1, wherein said mutant allele encodes a mutant protein comprising a G228E, L242F, E324K, G340E, or A362T substitution in SEQ ID NO: 1.

7. The plant or plant part according to claim 1, wherein the mutant allele is produced by random mutagenesis or targeted mutagenesis.

8. The plant or plant part according to claim 1, wherein said plant or plant part is diploid and is homozygous for the mutant ClHWS allele and is optionally further homozygous for the mutant multibranching allele, which mutant allele encodes the protein of SEQ ID NO: 9.

9. A seed from which a plant or plant part according to claim 1 can be grown.

10. Pollen produced by a plant according to claim 1 and comprising at least one copy of said mutant allele.

11. The plant part according to claim 1 comprising at least one copy of said mutant allele, wherein the plant part is a cell, a flower, a leaf, a stem, a cutting, pollen, a root, a rootstock, a scion, a protoplast, a microspore or an anther.

12. A vegetatively propagated plant propagated from a plant part according to claim 11.

13. A method of producing seedless watermelon fruits, said method comprising growing a diploid watermelon plant according to claim 8 in the vicinity of a triploid watermelon plant, allowing pollination of female flowers of said triploid watermelon plant with pollen produced by the watermelon plant according to claim 8.

14. The method according to claim 13, wherein said method further comprises harvesting the fruits that develop from said female flowers.

15. A method for screening watermelon plants, watermelon seeds, watermelon plant parts or DNA therefrom for the presence of a mutant allele of a gene named ClHWS, or for selecting a watermelon plant, seed or plant part comprising a mutant allele of a gene named ClHWS, or for generating a watermelon plant, seed or plant part comprising a mutant allele of a gene named ClHWS, wherein said mutant allele either comprises one or more mutations in a regulatory element, resulting in no expression or reduced expression of the allele compared to the wild type allele, and/or encodes a mutant protein comprising one or more amino acids replaced, inserted or deleted in the C-terminal region starting at amino acid 93 and ending at amino acid 380 compared to the wild type protein, wherein the wild type watermelon allele comprises SEQ ID NO: 4, said method comprises the steps of a) introducing mutations by random mutagenesis techniques or targeted mutagenesis techniques into said ClHWS gene in watermelon plants or seeds or plant parts, b) providing one or more genomic DNA samples of one or more watermelon plants, seeds or plant parts from a), c) carrying out a genotyping assay, using the DNA samples of b) as template, that discriminates between the wild type Clhws allele and the mutant Clhws allele, wherein said genotyping assay is based on nucleic acid amplification making use of Clhws allele-specific oligonucleotide primers, and/or wherein said genotyping assay is based on nucleic acid hybridization making use of Clhws allele-specific oligonucleotide probes, and optionally d) selecting a plant, seed or plant part comprising one or two copies of the mutant allele.

16. The plant or plant part according to claim 1, wherein the mutant allele is produced by CRISPR based methods.

17. A method for generating watermelon plants comprising mutant Clhws alleles comprising the steps of:

a) introducing mutations in a population of watermelon plants, plant parts or seeds or providing a population of mutated plants, or progeny thereof;

b) selecting a plant comprising a mutant Clhws allele, and optionally c) determining if the plant selected produces a higher percentage of male flowers than the wild type, non-mutated plant line, or a higher ratio of male to female flowers, wherein the wild type watermelon Clhws allele comprises SEQ ID NO: 4; and wherein said mutant allele encodes a mutant protein comprising one or more amino acids replaced, inserted or deleted in the C-terminal region starting at amino acid 93 and ending at amino acid 380 compared to the wild type protein.

18. A method for amplifying and/or hybridizing a part of the genomic DNA of watermelon plants, seeds or plant parts is provided comprising the steps of:

a) providing a sample or a plurality of samples of genomic DNA of a watermelon plant or of a plurality of plants, b) providing at least a pair of PCR primers or at least one oligonucleotide probe, which primers or oligonucleotide probe comprise at least 10, 11, 12, 13, 14, 15, 16, 17, 18, 19, 20, 21, 22 or more consecutive nucleotides of the genomic allele of the Clhws gene and can hybridize to the genomic allele and/or amplify part of the genomic allele in a PCR assay, and c) carrying out a PCR assay using the primer pair or a hybridization assay using the probe of step b) on the sample(s) of step a) to generate a PCR amplification product and/or a oligonucleotide hybridization product, and optionally d) selecting a plant or plant part or seed comprising one or two copies of a a mutant allele of the Clhws gene in the genome, wherein the wild type allele of the Clhws gene comprises SEQ ID NO: 4; and wherein said mutant allele encodes a mutant protein comprising one or more amino acids replaced, inserted or deleted in the C-terminal region starting at amino acid 93 and ending at amino acid 380 compared to the wild type protein.

19. A watermelon plant or plant part comprising at least one copy of a mutant allele of a gene named ClHWS (*Citrullus lanatus* HAWAIIAN SKIRT), wherein said mutant allele encodes a mutant protein comprising a S67F substitution in SEQ ID NO: 1, wherein said mutant allele confers an increase in the percentage of male flowers developing when the mutant allele is in homozygous form, and wherein the wild type watermelon allele comprises SEQ ID NO: 4.

* * * * *

SEQUENCE LISTING

```
<160> NUMBER OF SEQ ID NOS: 12

<210> SEQ ID NO 1
<211> LENGTH: 405
<212> TYPE: PRT
<213> ORGANISM: Citrullus lanatus
<220> FEATURE:
<221> NAME/KEY: F-box-domain
<222> LOCATION: (45)..(83)

<400> SEQUENCE: 1

Met Glu Gly Gln Thr Ser Trp Ile Arg His Cys Tyr Asn Asp Met Ser
1               5                   10                  15

Arg Asp Leu Glu Asp Leu Asp Ser Tyr Leu Asp Phe Thr Asn Glu Gly
            20                  25                  30

Gly Lys Glu Ala Val Ala Val Ser Val Glu Ser Ile Leu Pro Asp Asp
        35                  40                  45

Leu Leu Glu Arg Ile Leu Ser Tyr Leu Pro Ile Ala Ser Ile Phe Arg
    50                  55                  60

Ala Gly Ser Val Cys Lys Arg Trp His Asp Ile Val Ser Ser Arg Arg
65                  70                  75                  80

Phe Leu Trp Asn Val Ser His Ile Leu Ser Gln Lys Pro Trp Tyr Phe
                85                  90                  95

Met Phe Thr Ser Ser Asp Glu Pro Ile Gly Tyr Ala Tyr Asp Pro Val
            100                 105                 110

Leu Arg Lys Trp Tyr Ala Ile Asn Leu Pro Cys Ile Asp Lys Ser Asn
        115                 120                 125

Cys Phe Ile Ala Ser Ser Cys Gly Leu Val Cys Phe Met Asp Asn Asp
    130                 135                 140

Ser Arg Ser Glu Leu His Val Cys Asn Pro Ile Thr Lys Cys Ser Met
145                 150                 155                 160

Lys Leu Pro Glu Pro Thr Gly Ser Lys Phe Ser Asp Tyr Ser Ala Leu
                165                 170                 175

Ala Ile Ser Val Asn Arg Val Ser His Asn Tyr Thr Ile Ser Val Val
            180                 185                 190

Lys Ser Lys Gln Val Pro Gly Asn Phe Phe Gln Trp Asp Ile Ser Ile
        195                 200                 205

His Ile Tyr Asp Ser Glu Thr Met Met Trp Val Thr Ser Leu Thr Glu
    210                 215                 220

Val Leu Ser Gly Trp Arg Gly Gly Asp Glu Ser Val Ile Cys Asp Gly
225                 230                 235                 240
```

```
Val Leu Tyr Leu Leu Ile Tyr Ser Thr Gly Gly Gly Ala Pro Asp Asn
            245                 250                 255

Arg His Gly Leu Val Thr Tyr Asn Ile Ser Asn His Ser Ser His Gly
            260                 265                 270

Leu Leu Ile Arg Ser Phe Ile Pro Ala Pro Cys Ser Leu Thr Cys Gly
            275                 280                 285

Arg Leu Met Asn Leu Lys Gln Lys Leu Val Met Val Gly Gly Ile Gly
            290                 295                 300

Lys Gln Asp Arg Pro Asp Ile Ile Lys Gly Ile Gly Ile Trp Ile Leu
305                 310                 315                 320

Cys Gly Lys Glu Trp Arg Glu Ile Ala Arg Met Pro His Lys Phe Phe
            325                 330                 335

Gln Gly Phe Gly Glu Phe Asp Asp Val Phe Ala Ser Cys Gly Thr Asp
            340                 345                 350

Asp Leu Ile Tyr Ile Gln Ser Tyr Gly Ala Pro Ala Leu Leu Thr Phe
            355                 360                 365

Asp Met Asn Leu Arg Gln Trp Arg Trp Ser Gln Lys Cys Pro Val Thr
            370                 375                 380

Lys Arg Phe Pro Leu Gln Leu Phe Thr Gly Phe Cys Phe Glu Pro Arg
385                 390                 395                 400

Leu Glu Ile Asn Pro
                405

<210> SEQ ID NO 2
<211> LENGTH: 203
<212> TYPE: PRT
<213> ORGANISM: Citrullus lanatus

<400> SEQUENCE: 2

Met Glu Gly Gln Thr Ser Trp Ile Arg His Cys Tyr Asn Asp Met Ser
1               5                   10                  15

Arg Asp Leu Glu Asp Leu Asp Ser Tyr Leu Asp Phe Thr Asn Glu Gly
            20                  25                  30

Gly Lys Glu Ala Val Ala Val Ser Val Glu Ser Ile Leu Pro Asp Asp
            35                  40                  45

Leu Leu Glu Arg Ile Leu Ser Tyr Leu Pro Ile Ala Ser Ile Phe Arg
        50                  55                  60

Ala Gly Ser Val Cys Lys Arg Trp His Asp Ile Val Ser Ser Arg Arg
65                  70                  75                  80

Phe Leu Trp Asn Val Ser His Ile Leu Ser Gln Lys Pro Trp Tyr Phe
                85                  90                  95

Met Phe Thr Ser Ser Asp Glu Pro Ile Gly Tyr Ala Tyr Asp Pro Val
            100                 105                 110

Leu Arg Lys Trp Tyr Ala Ile Asn Leu Pro Cys Ile Asp Lys Ser Asn
            115                 120                 125

Cys Phe Ile Ala Ser Ser Cys Gly Leu Val Cys Phe Met Asp Asn Asp
            130                 135                 140

Ser Arg Ser Glu Leu His Val Cys Asn Pro Ile Thr Lys Cys Ser Met
145                 150                 155                 160

Lys Leu Pro Glu Pro Thr Gly Ser Lys Phe Ser Asp Tyr Ser Ala Leu
            165                 170                 175

Ala Ile Ser Val Asn Arg Val Ser His Asn Tyr Thr Ile Ser Val Val
            180                 185                 190

Lys Ser Lys Gln Val Pro Gly Asn Phe Phe Gln
```

```
              195                    200
```

<210> SEQ ID NO 3
<211> LENGTH: 1218
<212> TYPE: DNA
<213> ORGANISM: Citrullus lanatus

<400> SEQUENCE: 3

```
atggagggac aaacgtcgtg gataaggcat tgctacaatg acatgtcaag agatcttgaa       60
gatctcgatt cttacttgga tttcacaaat gaaggaggca aagaggctgt agcagtttct      120
gtggagtcaa tcctgcctga tgacttgttg gaacgaattc tgtcctatct accgatagca      180
agcattttca gagctggttc tgtgtgcaaa agatggcatg atatagttag ttcgaggagg      240
tttttgtgga atgtctcaca catcctatca caaaaacctt ggtatttcat gtttacaagc      300
tctgatgagc ctattggtta tgcctatgat ccggttctta gaaagtggta tgctattaat      360
ctcccgtgca tcgacaagtc aaattgcttt attgcctcgt catgtggctt ggtttgtttc      420
atggacaatg acagtcgaag tgagttacat gtctgcaacc ctataaccaa atgctcaatg      480
aaattaccag agcccacggg atcgaagttc tctgattata gtgcacttgc aatttctgta      540
aacagggttt cacacaacta tacaatctct gttgtgaaat ccaagcaagt tcctggaaac      600
ttctttcaat gggatatatc aattcatatt tatgattcgg aaacgatgat gtgggttacc      660
tctctgactg aagtcttgtc gggatggaga ggtggcgacg agagtgtgat ttgtgatgga      720
gttctttacc tcttaatcta ttcaactggg ggtggagcac ctgataaccg ccacggtctt      780
gttacttata atatctctaa ccattcttct catggtctgt tgataagaag cttcattcct      840
gctccctgtt ctctcacatg cggtcgattg atgaatctta agcagaagct ggtcatggtt      900
gggggaattg gtaaacagga taggcctgac atcattaagg ggattggaat ttggattctt      960
tgcgggaagg agtggcgaga aattgcacgc atgccccata agttcttcca gggatttggg     1020
gagttcgacg atgtttttgc cagctgcggc actgatgacc ttatttacat ccagagctat     1080
ggagctccag ctttacttac gtttgacatg aatctaagac aatggagatg gtcgcagaag     1140
tgcccagtga caaagagatt ccctctccag cttttcactg cttttgctt cgaaccaagg     1200 cttgagatca atccctga                                                    1218
```

<210> SEQ ID NO 4
<211> LENGTH: 1218
<212> TYPE: DNA
<213> ORGANISM: Citrullus lanatus

<400> SEQUENCE: 4

```
atggagggac aaacgtcgtg gataaggcat tgctacaatg acatgtcaag agatcttgaa       60
gatctcgatt cttacttgga tttcacaaat gaaggaggca aagaggctgt agcagtttct      120
gtggagtcaa tcctgcctga tgacttgttg gaacgaattc tgtcctatct accgatagca      180
agcattttca gagctggttc tgtgtgcaaa agatggcatg atatagttag ttcgaggagg      240
tttttgtgga atgtctcaca catcctatca caaaaacctt ggtatttcat gtttacaagc      300
tctgatgagc ctattggtta tgcctatgat ccggttctta gaaagtggta tgctattaat      360
ctcccgtgca tcgacaagtc aaattgcttt attgcctcgt catgtggctt ggtttgtttc      420
atggacaatg acagtcgaag tgagttacat gtctgcaacc ctataaccaa atgctcaatg      480
aaattaccag agcccacggg atcgaagttc tctgattata gtgcacttgc aatttctgta      540
aacagggttt cacacaacta tacaatctct gttgtgaaat ccaagcaagt tcctggaaac      600
```

-continued

```
ttctttcaat gggatatatc aattcatatt tatgattcgg aaacgatgat gtgggttacc      660
tctctgactg aagtcttgtc gggatggaga ggtggcgacg agagtgtgat ttgtgatgga      720
gttctttacc tcttaatcta ttcaactggg ggtggagcac ctgataaccg ccacggtctt      780
gttacttata atatctctaa ccattcttct catggtctgt tgataagaag cttcattcct      840
gctccctgtt ctctcacatg cggtcgattg atgaatctta agcagaagct ggtcatggtt      900
gggggaattg gtaaacagga taggcctgac atcattaagg ggattggaat ttggattctt      960
tgcgggaagg agtggcgaga aattgcacgc atgccccata agttcttcca gggatttggg     1020
gagttcgacg atgtttttgc cagctgcggc actgatgacc ttatttacat ccagagctat     1080
ggagctccag ctttacttac gtttgacatg aatctaagac aatggagatg gtcgcagaag     1140
tgcccagtga caaagagatt ccctctccag cttttcactg cttttgctt cgaaccaagg      1200 cttgagatca atccctga                                                    1218
```

```
<210> SEQ ID NO 5
<211> LENGTH: 201
<212> TYPE: DNA
<213> ORGANISM: artificial
<220> FEATURE:
<223> OTHER INFORMATION: marker mWM23348454
<220> FEATURE:
<221> NAME/KEY: SNP
<222> LOCATION: (101)..(101)

<400> SEQUENCE: 5
```

```
tctgattata gtgcacttgc aatttctgta aacagggttt cacacaacta tacaatctct       60
gttgtgaaat ccaagcaagt tcctggaaac ttctttcaat aggatatatc aattcatatt      120
tatgattcgg aaacgatgat gtgggttacc tctctgactg aagtcttgtc gggatggaga      180
ggtggcgacg agagtgtgat t                                                 201
```

```
<210> SEQ ID NO 6
<211> LENGTH: 411
<212> TYPE: PRT
<213> ORGANISM: Arabidopsis thaliana

<400> SEQUENCE: 6
```

```
Met Glu Ala Glu Thr Ser Trp Thr Asn Tyr Pro Tyr Ser Tyr Ile Thr
1               5                   10                  15

Tyr Val Pro Glu Ala Glu Ser Tyr Arg Glu Gln Ser Asp Asp Glu Ala
                20                  25                  30

Lys Val Glu Thr Phe Ser Met Asp Ser Leu Leu Pro Asp Asp Leu Leu
            35                  40                  45

Glu Arg Ile Leu Ser Phe Leu Pro Ile Ala Ser Ile Phe Arg Ala Gly
        50                  55                  60

Thr Val Cys Lys Arg Trp Asn Glu Ile Val Ser Ser Arg Arg Phe Leu
65                  70                  75                  80

Cys Asn Phe Ser Asn Asn Ser Val Ser Gln Arg Pro Trp Tyr Phe Met
                85                  90                  95

Phe Thr Thr Thr Asp Asp Pro Ser Gly Tyr Ala Tyr Asp Pro Ile Ile
            100                 105                 110

Arg Lys Trp Tyr Ser Phe Asp Leu Pro Cys Ile Glu Thr Ser Asn Trp
        115                 120                 125

Phe Val Ala Ser Ser Cys Gly Leu Val Cys Phe Met Asp Asn Asp Cys
    130                 135                 140
```

-continued

```
Arg Asn Lys Ile Tyr Val Ser Asn Pro Ile Thr Lys Gln Trp Arg Thr
145                 150                 155                 160

Leu Ile Glu Pro Pro Gly His Lys Ser Thr Asp Tyr Thr Ala Met Ser
                165                 170                 175

Thr Ser Val Asn Arg Ala Asn Gln Ala Val Asn Arg Ala Asn Arg Ser
                180                 185                 190

Tyr Ser Val Ser Ile Val Lys Ser Lys Gln Val Pro Gly Asn Phe Phe
                195                 200                 205

Gln Trp Asp Leu Ser Ile His Leu Tyr Ser Ser Glu Thr Met Thr Trp
    210                 215                 220

Thr Thr Leu Val Asn Asp Val Leu Ser Gly Trp Arg Gly Gly Asn Glu
225                 230                 235                 240

Ser Val Ile Cys Asn Asn Val Leu Tyr Phe Met Ile Tyr Ser Thr Gly
                245                 250                 255

Gly Ser Asp His Arg His Gly Leu Ile Ala Ser Asn Leu Ser Ser Ile
                260                 265                 270

Gly Ser Pro Ser Ser Gly Ile Leu Met Arg Ser Phe Ile Pro Met Pro
                275                 280                 285

Cys Ser Leu Thr Cys Gly Arg Leu Met Asn Leu Arg Glu Arg Leu Val
    290                 295                 300

Ile Val Gly Gly Ile Gly Lys His Asp Arg Pro Glu Val Ile Lys Gly
305                 310                 315                 320

Ile Gly Ile Trp Val Leu Lys Gly Lys Glu Trp Val Glu Met Ala Lys
                325                 330                 335

Met Pro Gln Arg Phe Phe Gln Gly Phe Gly Glu Phe Asp Glu Val Phe
                340                 345                 350

Ala Ser Ser Gly Thr Asp Asp Leu Val Tyr Ile Gln Ser Tyr Gly Ser
                355                 360                 365

Pro Ala Leu Leu Thr Phe Asp Met Asn Leu Lys Tyr Trp Arg Trp Ser
    370                 375                 380

Gln Lys Cys Pro Val Thr Lys Lys Phe Pro Leu Gln Leu Phe Thr Gly
385                 390                 395                 400

Phe Cys Phe Glu Pro Arg Leu Glu Ile Ala Pro
                405                 410
```

<210> SEQ ID NO 7
<211> LENGTH: 446
<212> TYPE: PRT
<213> ORGANISM: Citrullus lanatus

<400> SEQUENCE: 7

```
Met Ile Lys Trp Leu Leu Cys Phe Ser Phe Leu Ser Phe Ser Phe Ala
1                   5                   10                  15

Ile Pro Pro Ala Ser Glu Val Ser Ser Ser Asn Leu Ala Val Pro His
                20                  25                  30

Phe Gln Val Ala Ala Glu Glu Ala Phe Tyr Lys Gly Gln Thr Ser Trp
                35                  40                  45

Ile Arg His Cys Tyr Asn Asp Met Ser Arg Asp Leu Glu Asp Leu Asp
    50                  55                  60

Ser Tyr Leu Asp Phe Thr Asn Glu Gly Gly Lys Glu Ala Val Ala Val
65                  70                  75                  80

Ser Val Glu Ser Ile Leu Pro Asp Asp Leu Leu Glu Arg Ile Leu Ser
                85                  90                  95

Tyr Leu Pro Ile Ala Ser Ile Phe Arg Ala Gly Ser Val Cys Lys Arg
                100                 105                 110
```

-continued

```
Trp His Asp Ile Val Ser Ser Arg Arg Phe Leu Trp Asn Val Ser His
        115                 120                 125

Ile Leu Ser Gln Lys Pro Trp Tyr Phe Met Phe Thr Ser Ser Asp Glu
        130                 135                 140

Pro Ile Gly Tyr Ala Tyr Asp Pro Val Leu Arg Lys Trp Tyr Ala Ile
145                 150                 155                 160

Asn Leu Pro Cys Ile Asp Lys Ser Asn Cys Phe Ile Ala Ser Ser Cys
                165                 170                 175

Gly Leu Val Cys Phe Met Asp Asn Asp Ser Arg Ser Glu Leu His Val
                180                 185                 190

Cys Asn Pro Ile Thr Lys Cys Ser Met Lys Leu Pro Glu Pro Thr Gly
                195                 200                 205

Ser Lys Phe Ser Asp Tyr Ser Ala Leu Ala Ile Ser Val Asn Arg Val
        210                 215                 220

Ser His Asn Tyr Thr Ile Ser Val Val Lys Ser Lys Gln Val Pro Gly
225                 230                 235                 240

Asn Phe Phe Gln Trp Asp Ile Ser Ile His Ile Tyr Asp Ser Glu Thr
                245                 250                 255

Met Met Trp Val Thr Ser Leu Thr Glu Val Leu Ser Gly Trp Arg Gly
                260                 265                 270

Gly Asp Glu Ser Val Ile Cys Asp Gly Val Leu Tyr Leu Leu Ile Tyr
        275                 280                 285

Ser Thr Gly Gly Gly Ala Pro Asp Asn Arg His Gly Leu Val Thr Tyr
        290                 295                 300

Asn Ile Ser Asn His Ser Ser His Gly Leu Leu Ile Arg Ser Phe Ile
305                 310                 315                 320

Pro Ala Pro Cys Ser Leu Thr Cys Gly Arg Leu Met Asn Leu Lys Gln
                325                 330                 335

Lys Leu Val Met Val Gly Gly Ile Gly Lys Gln Asp Arg Pro Asp Ile
                340                 345                 350

Ile Lys Gly Ile Gly Ile Trp Ile Leu Cys Gly Lys Glu Trp Arg Glu
        355                 360                 365

Ile Ala Arg Met Pro His Lys Phe Phe Gln Gly Phe Gly Glu Phe Asp
        370                 375                 380

Asp Val Phe Ala Ser Cys Gly Thr Asp Asp Leu Ile Tyr Ile Gln Ser
385                 390                 395                 400

Tyr Gly Ala Pro Ala Leu Leu Thr Phe Asp Met Asn Leu Arg Gln Trp
                405                 410                 415

Arg Trp Ser Gln Lys Cys Pro Val Thr Lys Arg Phe Pro Leu Gln Leu
        420                 425                 430

Phe Thr Gly Phe Cys Phe Glu Pro Arg Leu Glu Ile Asn Pro
        435                 440                 445
```

<210> SEQ ID NO 8
<211> LENGTH: 2405
<212> TYPE: DNA
<213> ORGANISM: citrullus lanatus

<400> SEQUENCE: 8

```
atgataaagt ggttgctctg tttctcattt cttttccttct cctttgctat tccacctgca        60
tctgaggttt cttcatcgaa tctagcggta ccccatttttc aggtggctgc tgaggaggcc       120
ttttataagg tttgttcatc gtgggttgtt accatcagga cctaattttc atttttttgta       180 atcgttttttt ttttttttttt ctttcttgat ctgggtttttg tttttaatcc ctgtatttgc      240
```

```
tcatttgctg atggatatgg atttggctgt cttttaacgc gacgttttca tctttgattg      300
atccgtaact cttgtgtgtt tcactctcta ctcaccattt gttttctggt ctaatttgca      360
attctctgtt ggggttgagg tttaacagat gagatgcgtt ttatttattt ataattttac      420
ctttccgttt ggagaaggca taaatttatg ttgaattaat gtggactgga acttcttttg      480
gaaagcttct tttaaattg gtttccattg ctcatacttt tacccctttgc acggatgatt      540 aggagattta catttcttaa atctgttgtg gcagttattt tccctctttg gaatctggtc      600
tcggagatat ttaaatgctt atacatatct atatcttttg aaagaatatt gtactcatga      660
acagtgtctt tcttttgttg ctatctgcta ctctgtctgc catgctttcc tgtgggtttg      720
tgtataatgt cgtttgtttg ggttcaggtt ttatccacct ttaccctaaa tgtatggttt      780
tataacacct ttgtttcttg tgtatggtcg ctagttgtcc tttaaagtag tctactaatg      840
tctgtaattt ttccacttat taacccacat aggattctgg aagacatgat atgatttggg      900 ggtgatgtt ttacgccaaa ggttgtggct tctgttaatg ttattgtaac tgtaatgatt      960
agcaatgtta tgtagcagtc tctatgtttt agtcttgaac ctcccttctg ttgtcatttg     1020
tattaagttg aaatgtacct tttcctcctg acattttcta ttggaagaat gcgttttatg     1080
acgtgtggtt gtttcaattc agaagagttg gatcggttca ttccagctgc atcttcttgt     1140
agtttgacta ctgtatcagc tcttctttat ttcgatcatt cttcttaatg gagggacaaa     1200
cgtcgtggat aaggcattgc tacaatgaca tgtcaagaga tcttgaagat ctcgattctt     1260
acttggattt cacaaatgaa ggaggcaaag aggctgtagc agtttctgtg gagtcaatcc     1320
tgcctgatga cttgttggaa cgaattctgt cctatctacc gatagcaagc attttcagag     1380
ctggttctgt gtgcaaaaga tggcatgata tagttagttc gaggaggttt ttgtggaatg     1440
tctcacacat cctatcacaa aaaccttggt atttcatgtt tacaagctct gatgagccta     1500
ttggttatgc ctatgatccg gttcttagaa agtggtatgc tattaatctc ccgtgcatcg     1560
acaagtcaaa ttgctttatt gcctcgtcat gtggcttggt ttgtttcatg gacaatgaca     1620
gtcgaagtga gttacatgtc tgcaacccta taaccaaatg ctcaatgaaa ttaccagagc     1680
ccacgggatc gaagttctct gattatagtg cacttgcaat ttctgtaaac agggtttcac     1740
acaactatac aatctctgtt gtgaaatcca agcaagttcc tggaaacttc tttcaatggg     1800
atatatcaat tcatatttat gattcggaaa cgatgatgtg ggttacctct ctgactgaag     1860
tcttgtcggg atggagaggt ggcgacgaga gtgtgatttg tgatggagtt ctttacctct     1920
taatctattc aactgggggt ggagcacctg ataaccgcca cggtcttgtt acttataata     1980
tctctaacca ttcttctcat ggtctgttga taagaagctt cattcctgct ccctgttctc     2040
tcacatgcgg tcgattgatg aatcttaagc agaagctggt catggttggg ggaattggta     2100
aacaggatag gcctgacatc attaagggga ttggaatttg gattctttgc gggaaggagt     2160
ggcgagaaat tgcacgcatg ccccataagt tcttccaggg atttggggag ttcgacgatg     2220
tttttgccag ctgcggcact gatgacctta tttacatcca gagctatgga gctccagctt     2280
tacttacgtt tgacatgaat ctaagacaat ggagatggtc gcagaagtgc ccagtgacaa     2340
agagattccc tctccagctt ttcactggct tttgcttcga accaaggctt gagatcaatc     2400
cctga                                                                  2405
```

<210> SEQ ID NO 9
<211> LENGTH: 275
<212> TYPE: PRT

<213> ORGANISM: Citrullus lanatus

<400> SEQUENCE: 9

```
Met Val Asn Asn Ala Leu Leu Glu Ala Leu Asn Val Arg Val Leu Gly
1               5                   10                  15

Thr Gly Asp Arg Ser Leu Val Leu Ala His Gly Phe Gly Thr Asp Gln
            20                  25                  30

Ser Ala Trp Gln Leu Ile Tyr Pro Ser Phe Thr Pro Tyr Tyr Arg Val
        35                  40                  45

Ile Leu Tyr Asp Leu Val Cys Ala Gly Ser Val Asn Pro Asp Phe Phe
    50                  55                  60

Asp Phe Ser Arg Tyr Thr Thr Leu Asp Ala Phe Val Asp Asp Leu Ile
65                  70                  75                  80

Ser Ile Leu Asp Ser Leu His Val His Arg Cys Ala Phe Val Gly His
                85                  90                  95

Ser Val Ser Ala Met Val Gly His Ser Val Ser Ala Met Val Gly Ile
            100                 105                 110

Leu Ala Ser Ile Arg Arg Pro Glu Leu Phe Ser Lys Leu Ile Leu Ile
        115                 120                 125

Gly Ala Ser Pro Arg Phe Leu Asn Asp Gly Asp Tyr His Gly Gly Phe
    130                 135                 140

Glu Gln Ser Glu Ile Asp Arg Val Phe Ala Ala Met Lys Ala Asn Tyr
145                 150                 155                 160

Gln Ser Trp Val Asn Gly Phe Ala Pro Leu Ala Val Gly Ala Asp Val
                165                 170                 175

Pro Ala Ala Val Gln Glu Phe Ser Arg Thr Leu Phe Asn Met Arg Pro
            180                 185                 190

Asp Ile Ser Leu Phe Val Ser Lys Val Ile Phe Ser Ser Asp Leu Arg
        195                 200                 205

Gly Val Leu Gly Leu Val Lys Val Pro Cys Cys Ile Ile Gln Thr Ala
    210                 215                 220

Gln Asp Val Ser Val Pro Ala Ser Val Ala Ile Tyr Leu Arg Asp His
225                 230                 235                 240

Leu Gly Gly Arg Asn Thr Val Glu Met Leu Asp Thr Glu Gly His Leu
                245                 250                 255

Pro His Leu Ser Ala Pro Gln Leu Leu Val Arg Lys Leu Arg Arg Ala
            260                 265                 270

Leu Ser Arg
        275
```

<210> SEQ ID NO 10
<211> LENGTH: 917
<212> TYPE: DNA
<213> ORGANISM: Citrullus lanatus

<400> SEQUENCE: 10

```
atggttaaca acgcccttct tgaagccctt aatgtccgtg tcctcggcac cggcgaccgt      60
tctctggtcc tggcccatgg cttcggcacc gaccagtccg cttggcaact catttaccct     120
tcctttactc cttactaccg cgtcatcctt tacgaccttg tctgcgccgg tagcgtcaac     180
cccgacttct tcgatttctc ccgctacacc actctcgacg ccttcgtcga cgatctcatc     240
tccatcctag actctctcca cgtccaccgc tgcgcctttg tcggccactc cgtctccgcc     300
atggtcggcc actccgtctc cgccatggtc ggcatcctcg cctccatccg ccgtcccgaa     360
ctcttctcta agctcatctt aatcggcgcc tccccaaggt cctttccact ccacactct     420
```

```
gttttctaa ctactctgtt tttttcccct gtttttataa aattcttttt attttattt        480 ttttcaggtt cctcaacgac ggcgactacc acggtgggtt cgaacagagc gagattgaca      540
gggtcttcgc tgcaatgaag gctaattacc aatcctgggt caacggcttt gccctcttg      600 ctgtcggtgc cgatgttccc gctgccgttc aggaattcag ccggactctc ttcaatatga      660
gacccgacat ttccctcttc gtctctaagg tcatcttcag cagcgatctc cggggagtcc      720
tcggtctcgt caaagtcccc tgttgcataa ttcaaaccgc ccaagacgtc tctgttccgg      780
cctccgtcgc tatctacctc cgagaccacc tcggcggccg gaacaccgtg gagatgctcg      840
acaccgaagg ccacctaccc catctgagtg cccctcagct actcgtacgg aaactccgcc      900
gtgctctttc ccggtga                                                    917
```

<210> SEQ ID NO 11
<211> LENGTH: 267
<212> TYPE: PRT
<213> ORGANISM: Citrullus lanatus

<400> SEQUENCE: 11

```
Met Val Asn Asn Ala Leu Leu Glu Ala Leu Asn Val Arg Val Leu Gly
1               5                   10                  15

Thr Gly Asp Arg Ser Leu Val Leu Ala His Gly Phe Gly Thr Asp Gln
            20                  25                  30

Ser Ala Trp Gln Leu Ile Tyr Pro Ser Phe Thr Pro Tyr Tyr Arg Val
        35                  40                  45

Ile Leu Tyr Asp Leu Val Cys Ala Gly Ser Val Asn Pro Asp Phe Phe
    50                  55                  60

Asp Phe Ser Arg Tyr Thr Thr Leu Asp Ala Phe Val Asp Asp Leu Ile
65                  70                  75                  80

Ser Ile Leu Asp Ser Leu His Val His Arg Cys Ala Phe Val Gly His
                85                  90                  95

Ser Val Ser Ala Met Val Gly Ile Leu Ala Ser Ile Arg Arg Pro Glu
            100                 105                 110

Leu Phe Ser Lys Leu Ile Leu Ile Gly Ala Ser Pro Arg Phe Leu Asn
        115                 120                 125

Asp Gly Asp Tyr His Gly Gly Phe Glu Gln Ser Glu Ile Asp Arg Val
        130                 135                 140

Phe Ala Ala Met Lys Ala Asn Tyr Gln Ser Trp Val Asn Gly Phe Ala
145                 150                 155                 160

Pro Leu Ala Val Gly Ala Asp Val Pro Ala Ala Val Gln Glu Phe Ser
                165                 170                 175

Arg Thr Leu Phe Asn Met Arg Pro Asp Ile Ser Leu Phe Val Ser Lys
            180                 185                 190

Val Ile Phe Ser Ser Asp Leu Arg Gly Val Leu Gly Leu Val Lys Val
            195                 200                 205

Pro Cys Cys Ile Ile Gln Thr Ala Gln Asp Val Ser Val Pro Ala Ser
        210                 215                 220

Val Ala Ile Tyr Leu Arg Asp His Leu Gly Gly Arg Asn Thr Val Glu
225                 230                 235                 240

Met Leu Asp Thr Glu Gly His Leu Pro His Leu Ser Ala Pro Gln Leu
                245                 250                 255

Leu Val Arg Lys Leu Arg Arg Ala Leu Ser Arg
            260                 265
```

-continued

```
<210> SEQ ID NO 12
<211> LENGTH: 893
<212> TYPE: DNA
<213> ORGANISM: Citrullus lanatus

<400> SEQUENCE: 12
atggttaaca acgcccttct tgaagccctt aatgtccgtg tcctcggcac cggcgaccgt      60
tctctggtcc tggcccatgg cttcggcacc gaccagtccg cttggcaact catttaccct     120
tcctttactc cttactaccg cgtcatcctt tacgaccttg tctgcgccgg tagcgtcaac     180
cccgacttct tcgatttctc ccgctacacc actctcgacg ccttcgtcga cgatctcatc     240
tccatcctag actctctcca cgtccaccgc tgcgcctttg tcggccactc cgtctccgcc     300
atggtcggca tcctcgcctc catccgccgt cccgaactct tctctaagct catcttaatc     360
ggcgcctccc caaggtcctt tccacttcca cactctgttt ttctaactac tctgttttt     420 tcccctgttt ttataaaatt ctttttattt ttatttttt caggttcctc aacgacggcg     480
actaccacgg tgggttcgaa cagagcgaga ttgacagggt cttcgctgca atgaaggcta     540
attaccaatc ctgggtcaac ggctttgccc ctcttgctgt cggtgccgat gttcccgctg     600
ccgttcagga attcagccgg actctcttca atatgagacc cgacatttcc ctcttcgtct     660
ctaaggtcat cttcagcagc gatctccggg gagtcctcgg tctcgtcaaa gtcccctgtt     720
gcataattca aaccgcccaa gacgtctctg ttccggcctc cgtcgctatc tacctccgag     780
accacctcgg cggccggaac accgtggaga tgctcgacac cgaaggccac ctaccccatc     840
tgagtgcccc tcagctactc gtacggaaac tccgccgtgc tctttcccgg tga           893
```